(12) United States Patent
Kuiper et al.

(10) Patent No.: US 10,893,949 B2
(45) Date of Patent: Jan. 19, 2021

(54) CROSSBAR SPINAL PROSTHESIS HAVING A MODULAR DESIGN AND SYSTEMS FOR TREATING SPINAL PATHOLOGIES

(71) Applicant: GLOBUS MEDICAL, INC., Audubon, PA (US)

(72) Inventors: Mark Kuiper, Seattle, WA (US); David Yager, Carnation, WA (US); Leonard Tokish, Issaquah, WA (US); David Michael Rosler, Seattle, WA (US); Mark Reiley, San Jose, CA (US); Michael J. Funk, North Bend, WA (US); Jorge A. Ochoa, Redmond, WA (US); Susan Rogers, Kirkland, WA (US); Christopher Ralph, Woodinville, WA (US); Mark Charbonneau, Bellevue, WA (US); Richard J. Broman, Kirkland, WA (US); Thomas McLeer, Redmond, WA (US)

(73) Assignee: Globus Medical Inc., Audubon, PA (US)

(*) Notice: Subject to any disclaimer, the term of this patent is extended or adjusted under 35 U.S.C. 154(b) by 0 days.

(21) Appl. No.: 15/902,388

(22) Filed: Feb. 22, 2018

(65) Prior Publication Data
US 2018/0243103 A1 Aug. 30, 2018

Related U.S. Application Data

(63) Continuation of application No. 15/350,889, filed on Nov. 14, 2016, now Pat. No. 10,010,426, which is a
(Continued)

(51) Int. Cl.
*A61B 17/70* (2006.01)
*A61F 2/44* (2006.01)
(Continued)

(52) U.S. Cl.
CPC ............ *A61F 2/4405* (2013.01); *A61B 17/15* (2013.01); *A61B 17/7064* (2013.01);
(Continued)

(58) Field of Classification Search
CPC ............................................ A61B 17/70–7046
See application file for complete search history.

(56) References Cited

U.S. PATENT DOCUMENTS 5,470,333 A * 11/1995 Ray .................... A61B 17/7055
606/261
5,688,272 A * 11/1997 Montague ............ A61B 17/705
606/250
(Continued)

*Primary Examiner* — Nicholas J Plionis
*Assistant Examiner* — Steven J Cotroneo

(57) ABSTRACT

An adaptable spinal facet joint prosthesis may include a pedicle fixation element; a laminar fixation element; and a facet joint bearing surface having a location adaptable with respect at least one of the pedicle fixation element and the laminar fixation element. Methods of implanting an adaptable spinal facet joint prosthesis may include determining a desired position for a facet joint bearing surface; and attaching a prosthesis comprising a facet joint bearing surface to a pedicle portion of a vertebra and a lamina portion of a vertebra to place the facet joint bearing surface in the desired position. A facet joint prosthesis implant tool may include a tool guide adapted to guide a vertebra cutting tool; and first and second fixation hole alignment elements extending from the saw guide. Systems for treating spinal pathologies may include intervertebral discs in combination with spinal and facet joint prostheses.

19 Claims, 32 Drawing Sheets

Related U.S. Application Data continuation-in-part of application No. 14/633,722, filed on Feb. 27, 2015, now Pat. No. 9,504,502, and a continuation-in-part of application No. 14/619,574, filed on Feb. 11, 2015, now Pat. No. 9,526,530, said application No. 14/633,722 is a continuation of application No. 13/847,746, filed on Mar. 20, 2013, now Pat. No. 8,992,574, said application No. 14/619,574 is a continuation of application No. 13/033,082, filed on Feb. 23, 2011, now Pat. No. 8,979,907, said application No. 13/847,746 is a continuation of application No. 11/948,994, filed on Nov. 30, 2007, now Pat. No. 8,425,557, said application No. 15/350,889 is a continuation of application No. 11/577,964, filed on Apr. 25, 2007, now abandoned, said application No. 13/033,082 is a continuation of application No. 11/642,417, filed on Dec. 20, 2006, now Pat. No. 7,914,556, said application No. 11/577,964 is a continuation of application No. PCT/US2005/038335, filed on Oct. 24, 2005, said application No. 11/642,417 is a continuation-in-part of application No. 11/206,676, filed on Aug. 17, 2005, now abandoned, which is a continuation-in-part of application No. 11/071,541, filed on Mar. 2, 2005, now Pat. No. 7,674,293, said application No. 11/948,994 is a continuation of application No. 10/973,939, filed on Oct. 25, 2004, now abandoned, said application No. 11/071,541 is a continuation-in-part of application No. 10/831,657, filed on Apr. 22, 2004, now Pat. No. 8,187,303, said application No. 10/973,939 is a continuation of application No. 10/831,657, filed on Apr. 22, 2004, now Pat. No. 8,187,303.

(51) Int. Cl.

| | |
|---|---|
| A61B 90/00 | (2016.01) |
| A61B 17/15 | (2006.01) |
| A61F 2/30 | (2006.01) |
| A61F 2/46 | (2006.01) |

(52) U.S. Cl.
CPC .......... *A61B 90/39* (2016.02); *A61F 2/30742* (2013.01); *A61F 2/442* (2013.01); *A61F 2/4455* (2013.01); *A61F 2002/3008* (2013.01); *A61F 2002/3055* (2013.01); *A61F 2002/3069* (2013.01); *A61F 2002/3085* (2013.01); *A61F 2002/30331* (2013.01); *A61F 2002/30405* (2013.01); *A61F 2002/30462* (2013.01); *A61F 2002/30507* (2013.01); *A61F 2002/30537* (2013.01); *A61F 2002/30538* (2013.01); *A61F 2002/30563* (2013.01); *A61F 2002/30566* (2013.01); *A61F 2002/30601* (2013.01); *A61F 2002/30604* (2013.01); *A61F 2002/30607* (2013.01); *A61F 2002/30616* (2013.01); *A61F 2002/30617* (2013.01); *A61F 2002/30682* (2013.01); *A61F 2002/30841* (2013.01); *A61F 2002/30878* (2013.01); *A61F 2002/30884* (2013.01); *A61F 2002/4631* (2013.01); *A61F 2220/0025* (2013.01); *A61F 2220/0033* (2013.01); *A61F 2220/0075* (2013.01); *A61F 2250/0004* (2013.01); *A61F 2250/0006* (2013.01); *A61F 2250/0007* (2013.01); *A61F 2250/0062* (2013.01); *A61F 2250/0097* (2013.01)

(56) References Cited

U.S. PATENT DOCUMENTS

| | | | |
|---|---|---|---|
| 2002/0123806 A1* | 9/2002 | Reiley | A61B 17/86 623/17.11 |
| 2003/0028250 A1* | 2/2003 | Reiley | A61F 2/4405 623/17.11 |
| 2003/0144665 A1* | 7/2003 | Munting | A61B 17/7043 606/278 |
| 2005/0027359 A1* | 2/2005 | Mashburn | A61F 2/4465 623/17.11 |

* cited by examiner

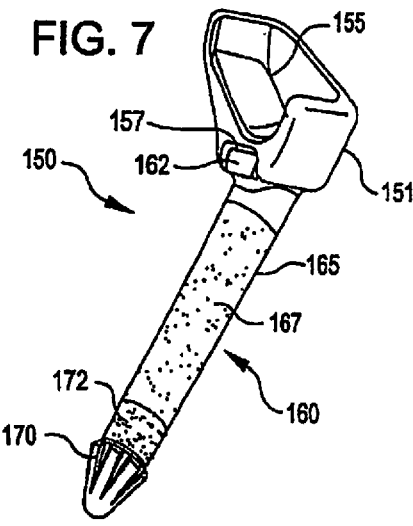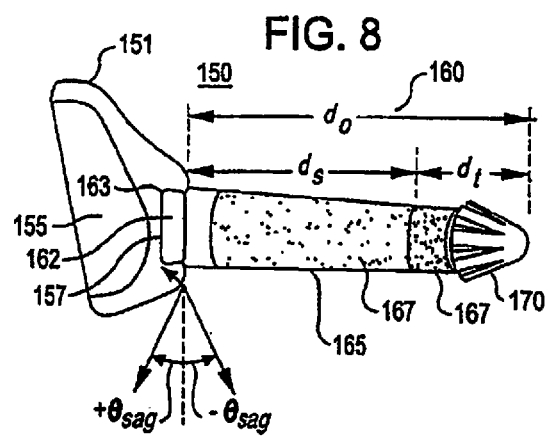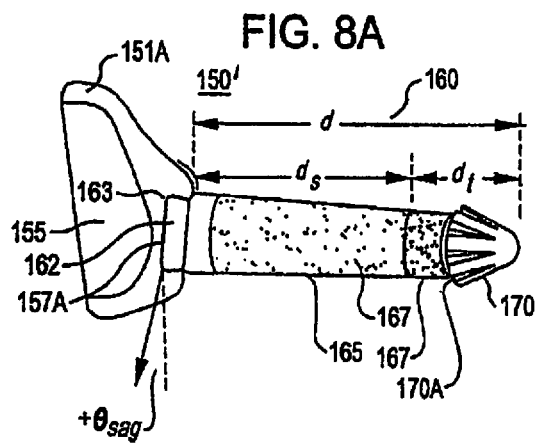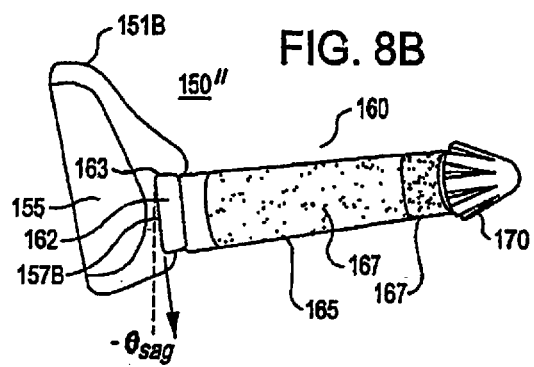

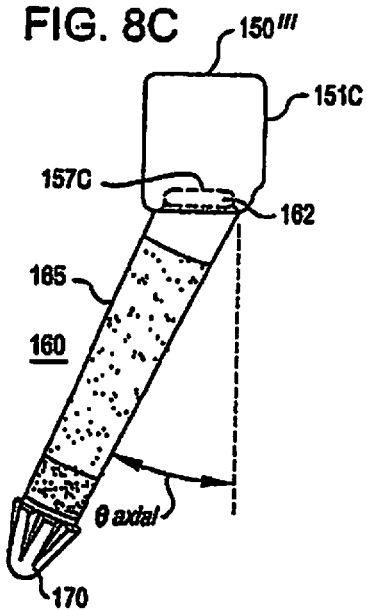
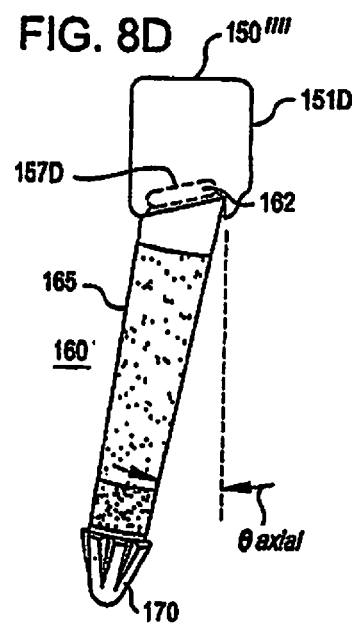
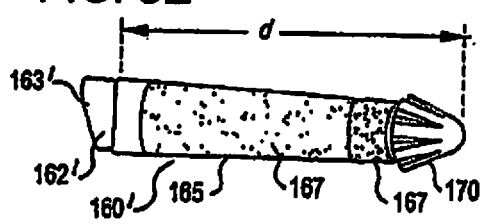
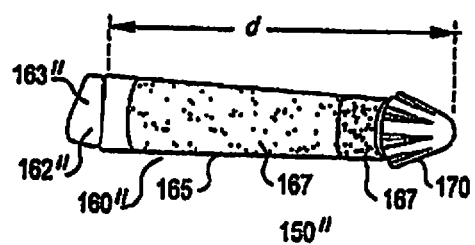
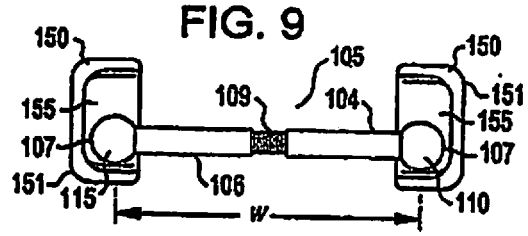
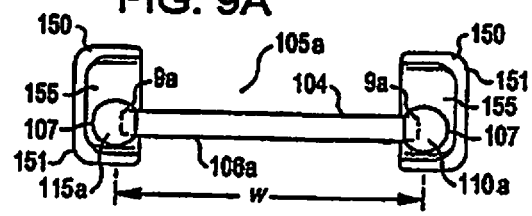

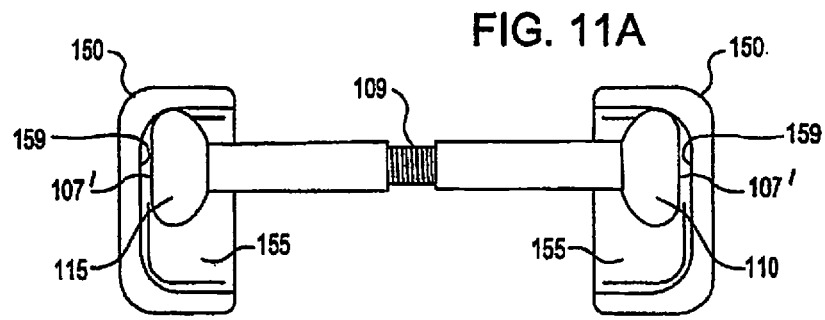
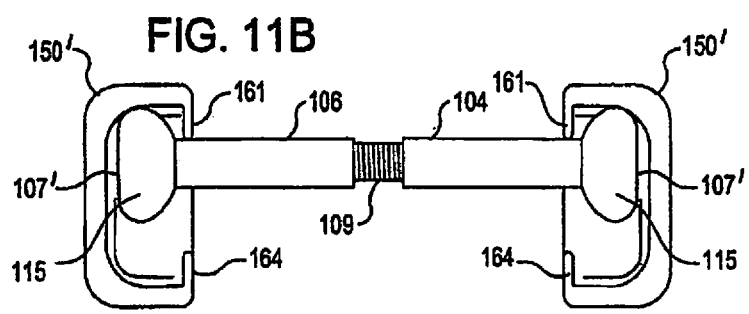
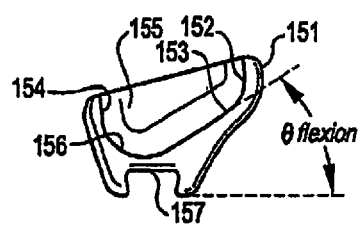 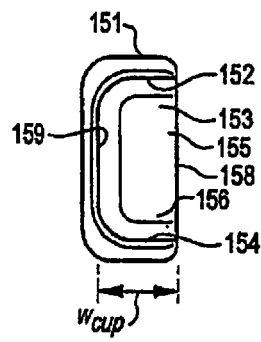
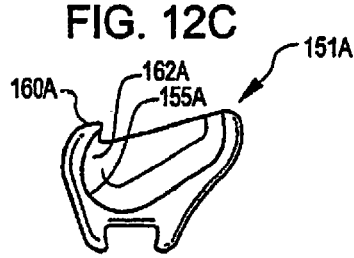 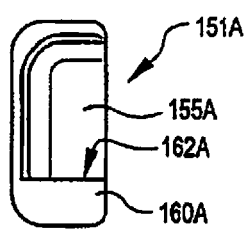

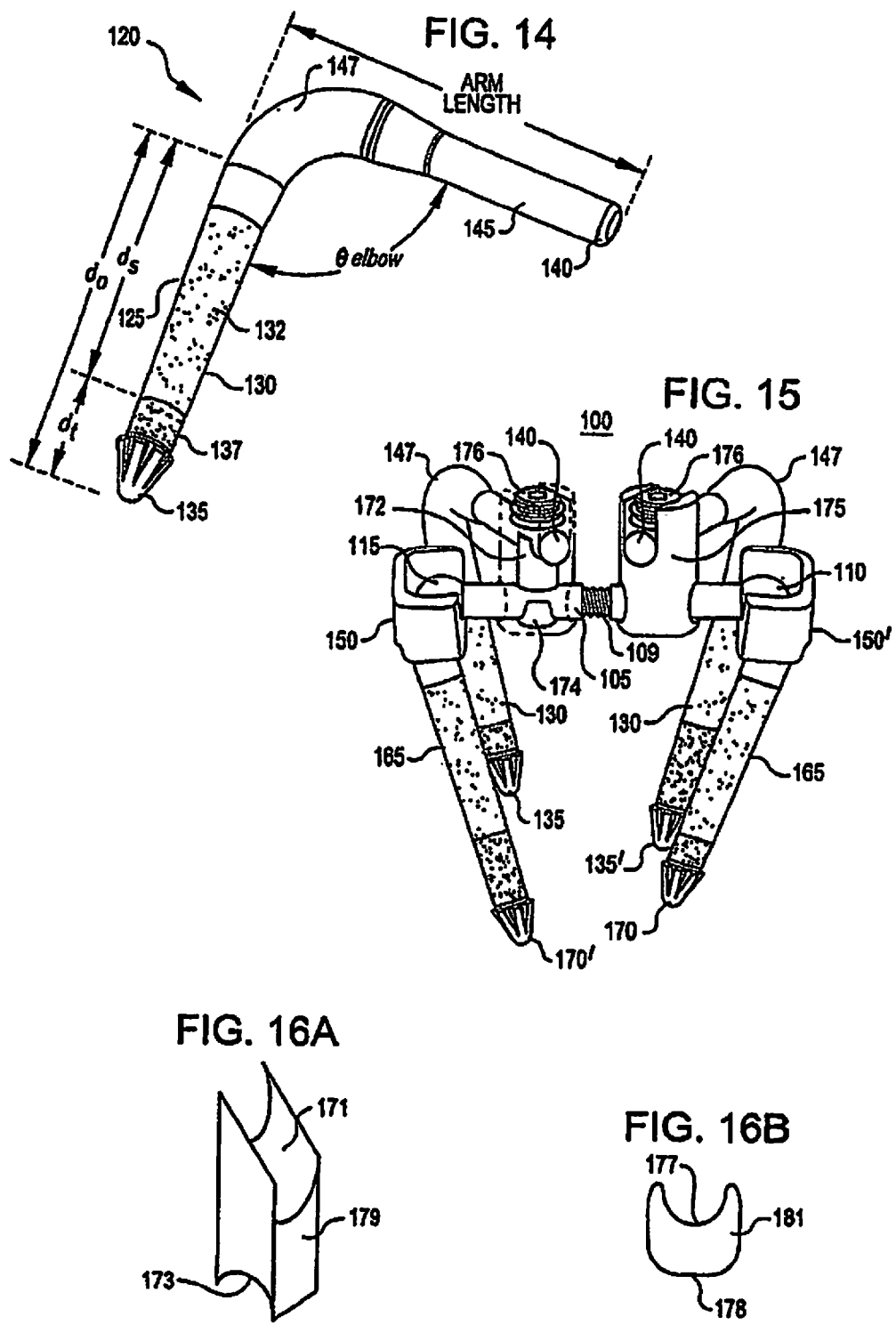

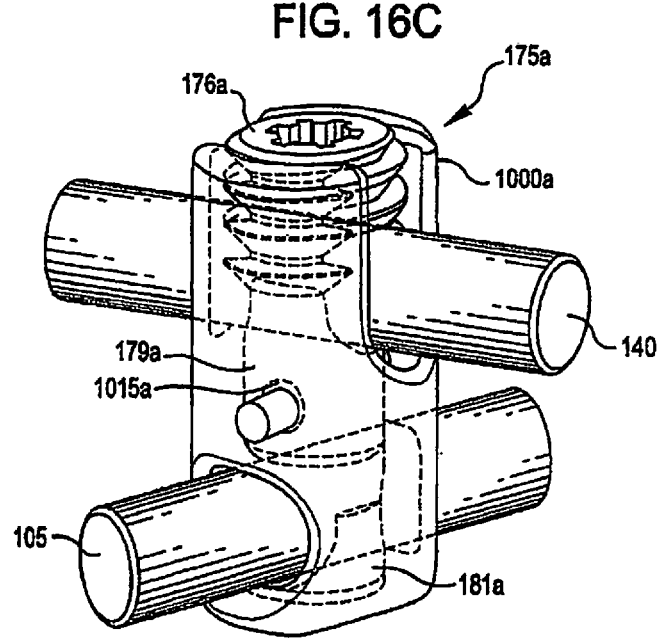
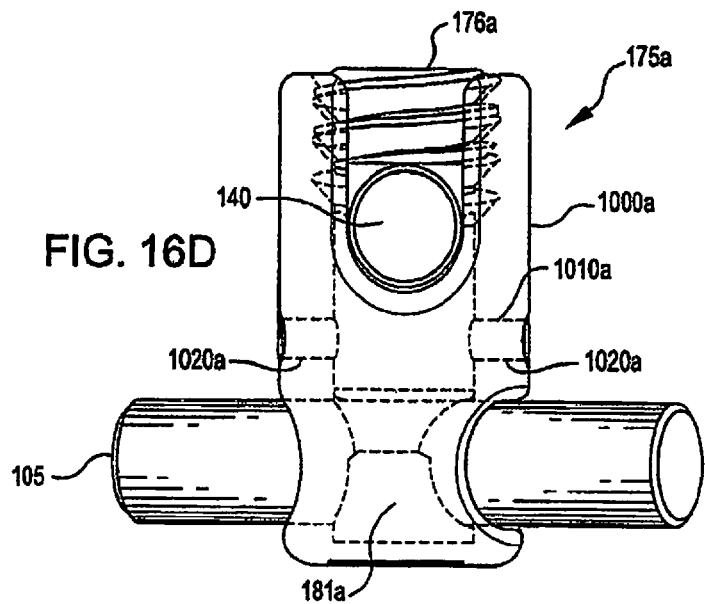

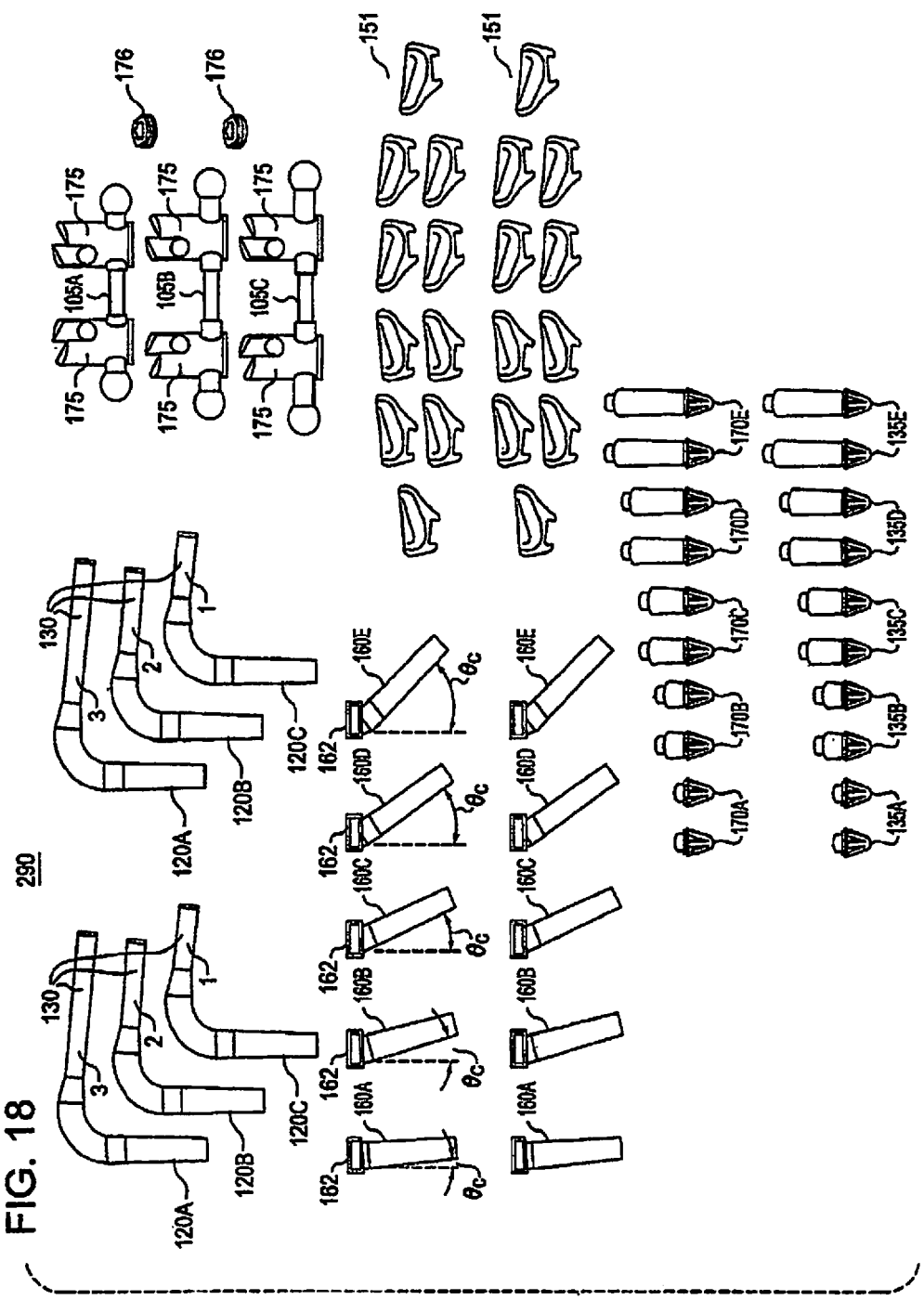

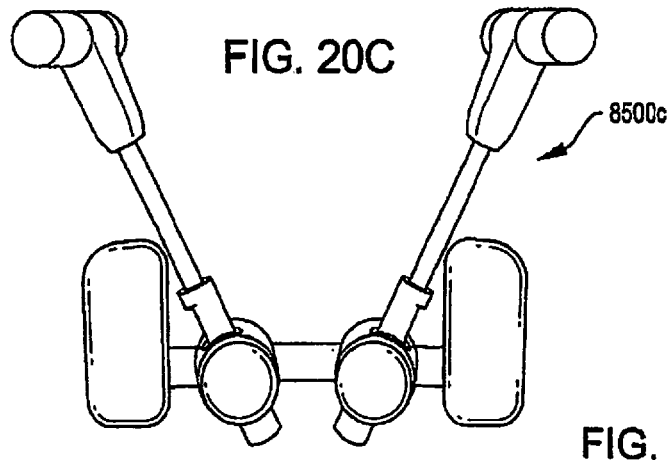
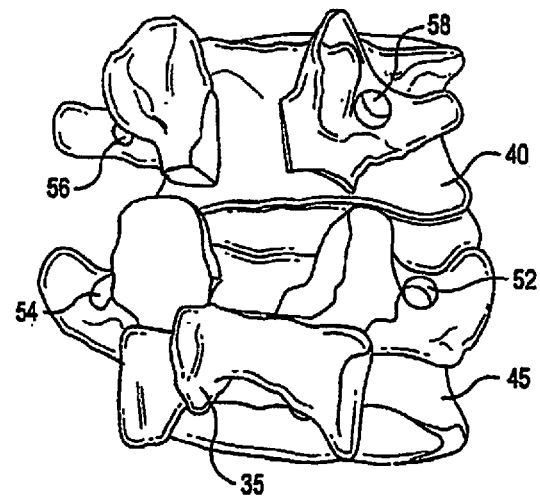
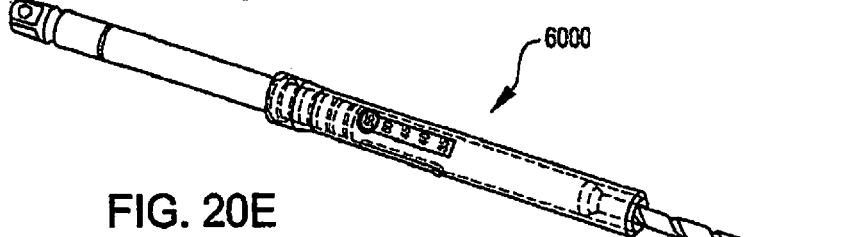
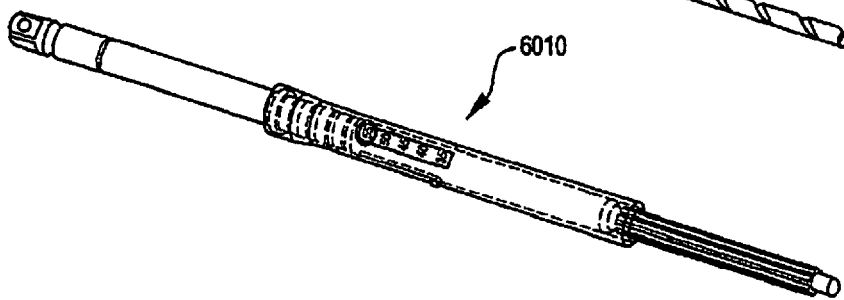

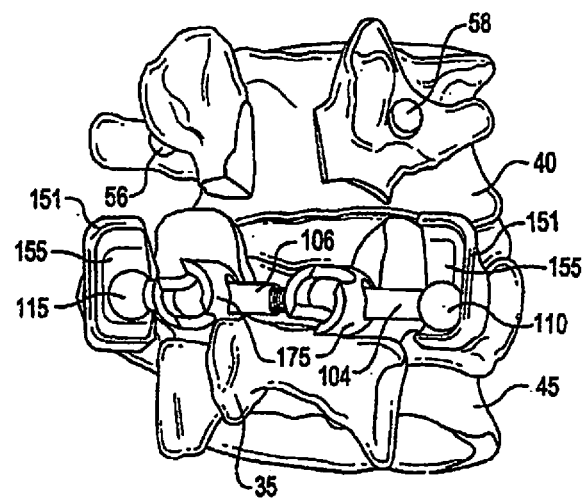
FIG. 23
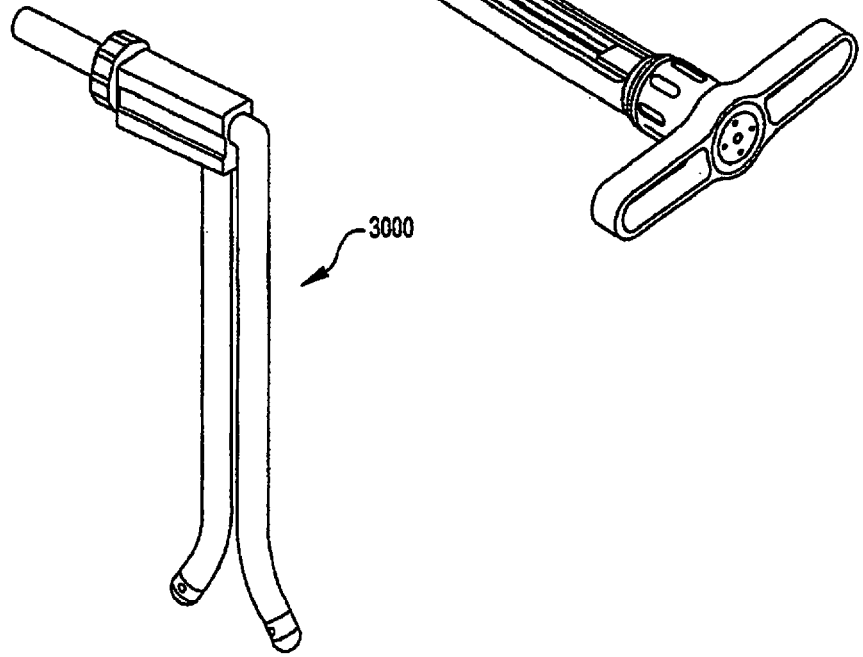
FIG. 23A
FIG. 23B

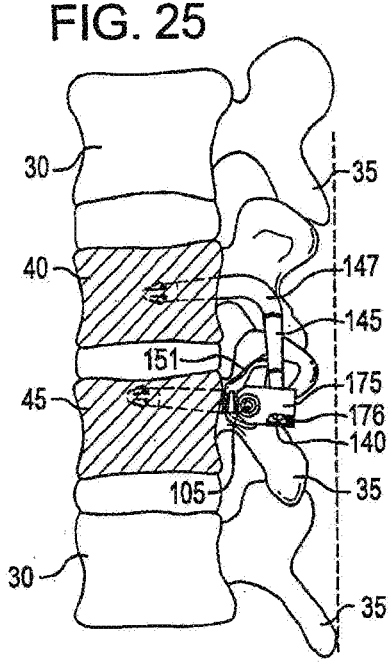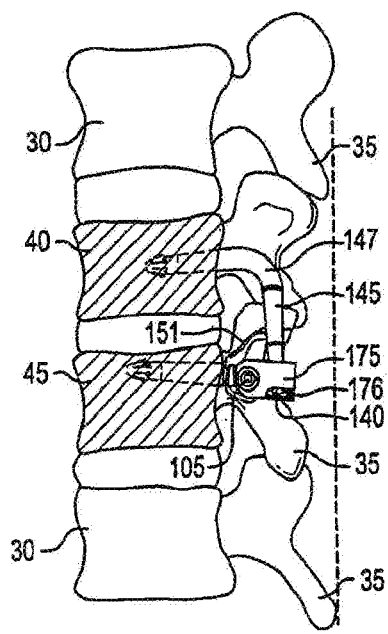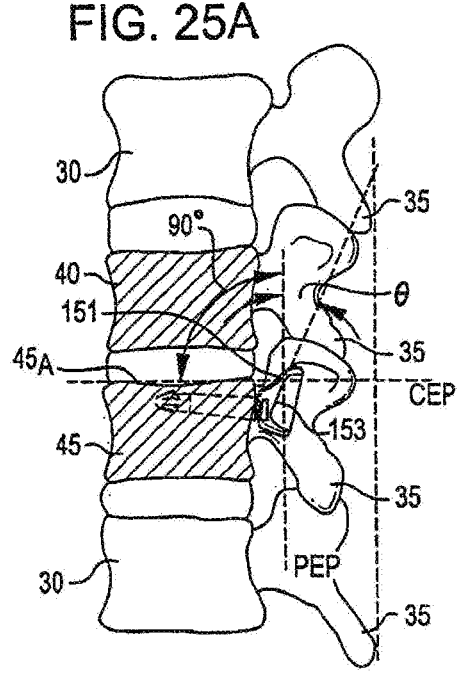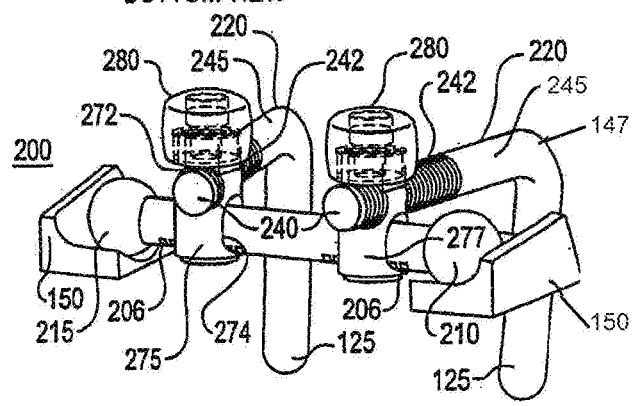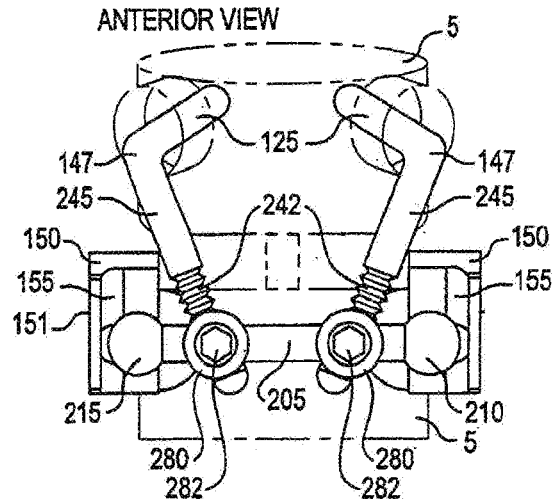

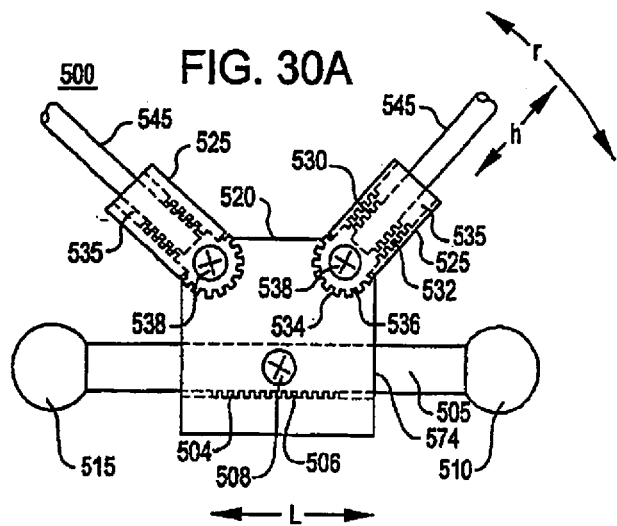
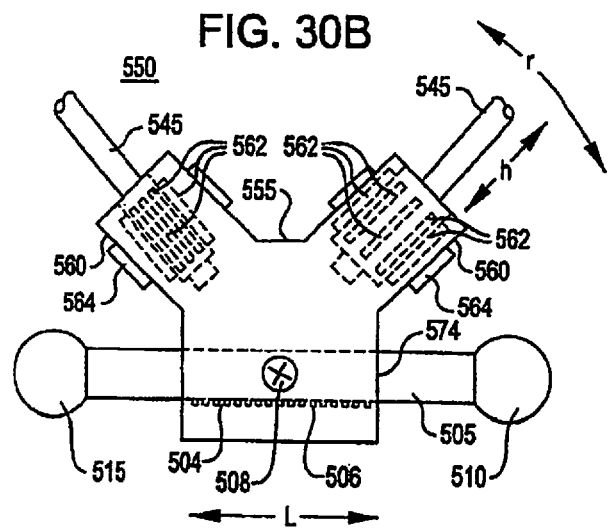
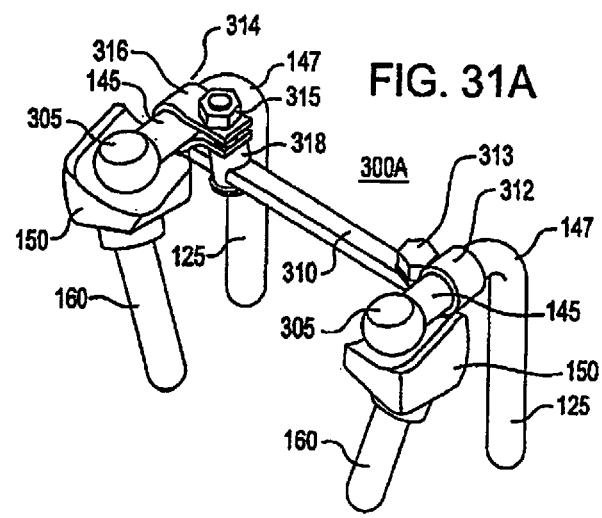

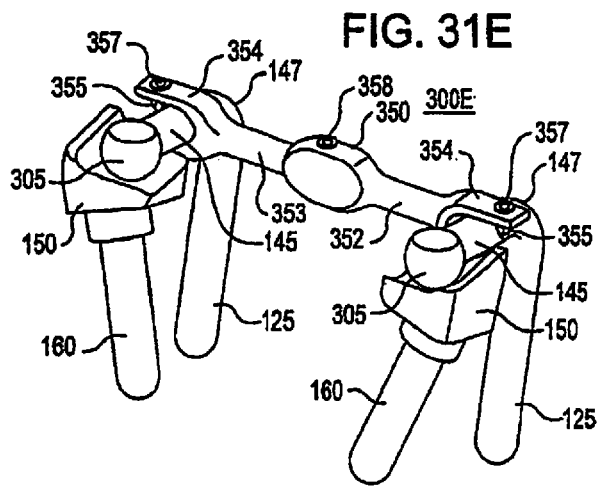
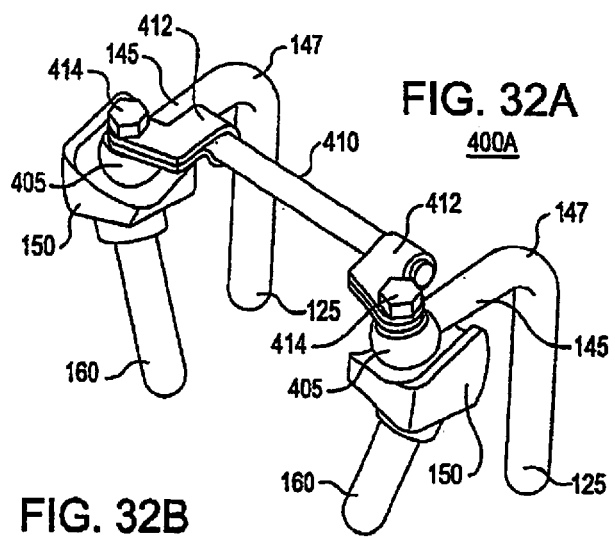
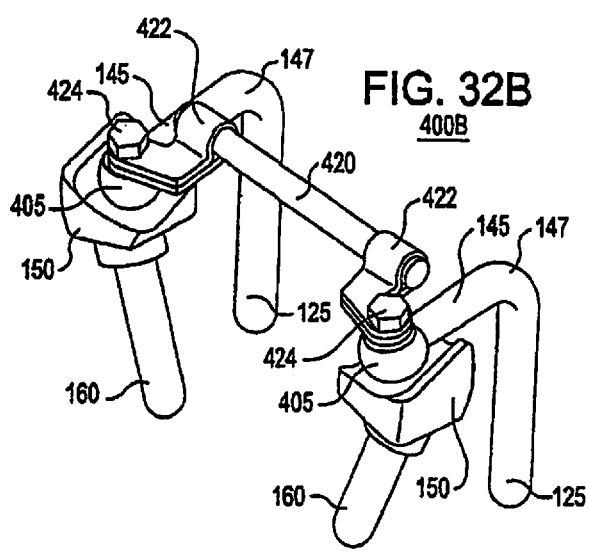

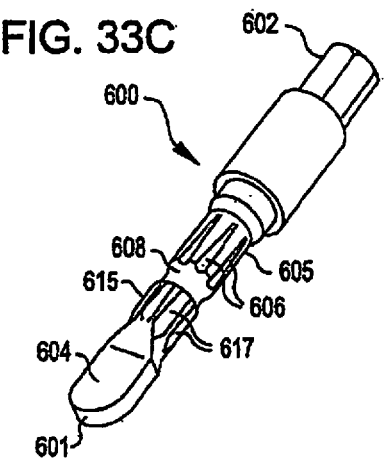
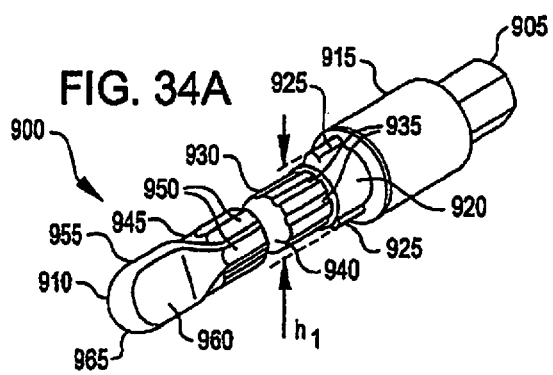
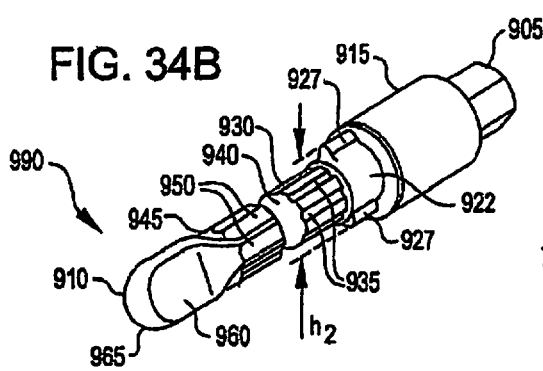
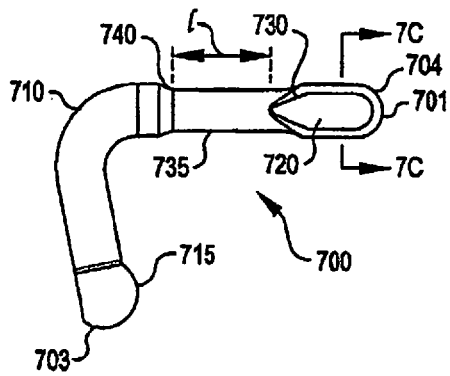
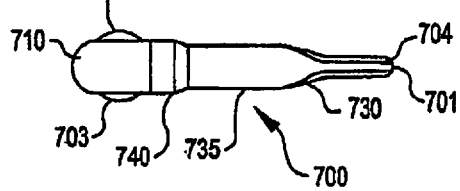
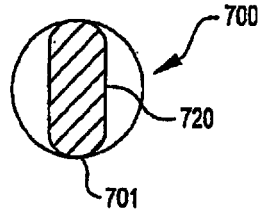
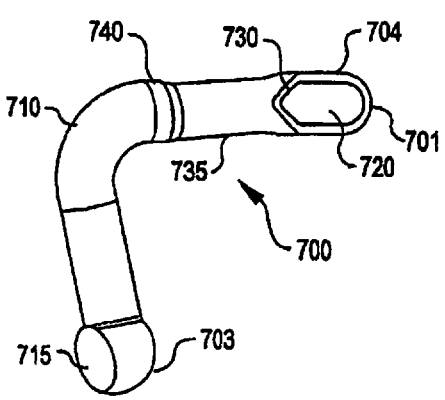

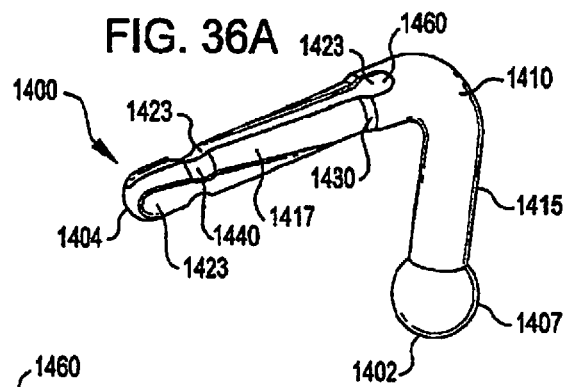
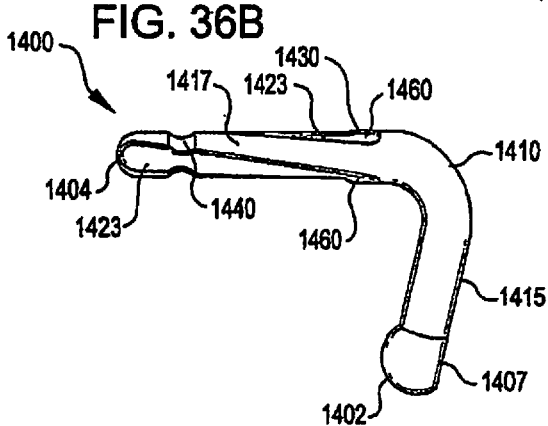
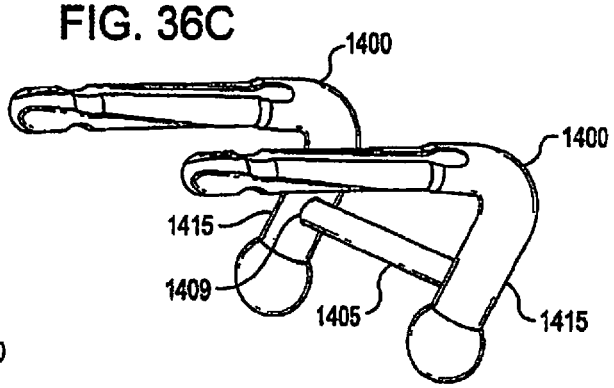
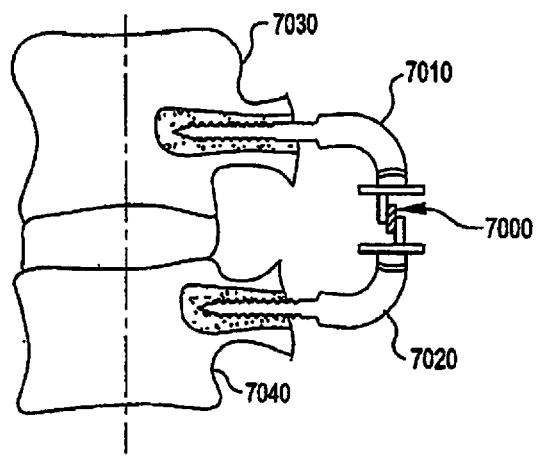

CROSSBAR SPINAL PROSTHESIS HAVING A MODULAR DESIGN AND SYSTEMS FOR TREATING SPINAL PATHOLOGIES

CROSS-REFERENCE TO RELATED APPLICATION

This application is a continuation of U.S. patent Ser. No. 15/350,889, filed on Nov. 14, 2016 (published as U.S. Patent Publication No. 2017/0056196), which is a continuation of U.S. patent application Ser. No. 11/577,964, filed Apr. 25, 2007, now abandoned, which is a continuation of PCT application No. PCT/US2005/038335, filed Oct. 24, 2005. U.S. patent Ser. No. 15/350,889, filed on Nov. 14, 2016 (published as U.S. Patent Publication No. 2017/0056196) is also a continuation-in-part of U.S. application Ser. No. 14/633,722, now U.S. Pat. No. 9,504,502, filed Feb. 27, 2015, which is a continuation of U.S. patent application Ser. No. 13/847,746, filed Mar. 20, 2013, now U.S. Pat. No. 8,992,574, which is a continuation of U.S. patent application Ser. No. 11/948,994, filed Nov. 30, 2007, now U.S. Pat. No. 8,425,557, which is a continuation of U.S. patent application Ser. No. 10/973,939, filed Oct. 25, 2004, now abandoned, which is a continuation-in-part of U.S. application Ser. No. 10/831,657, filed Apr. 22, 2004, now U.S. Pat. No. 8,187,303. U.S. patent Ser. No. 15/350,889, filed on Nov. 14, 2016 (published as U.S. Patent Publication No. 2017/0056196) is also a continuation-in-part of U.S. patent application Ser. No. 14/619,574, filed Feb. 11, 2015, now U.S. Pat. No. 9,526,530, which is a continuation of U.S. patent application Ser. No. 13/033,082, filed Feb. 23, 2011, now U.S. Pat. No. 8,979,907, which is a continuation of U.S. patent application Ser. No. 11/642,417, filed Dec. 20, 2006, now U.S. Pat. No. 7,914,556, which is a continuation-in-part of U.S. patent application Ser. No. 11/206,676, filed Aug. 17, 2005, now abandoned, which is a continuation-in-part of U.S. patent application Ser. No. 11/071,541, filed Mar. 2, 2005, now U.S. Pat. No. 7,674,293, which is a continuation-in-part of U.S. patent application Ser. No. 10/831,657 filed Apr. 22, 2004, now U.S. Pat. No. 8,187,303, which claims priority to U.S. Provisional Application No. 60/602,827, field Aug. 18, 2004, U.S. Provisional Application No. 60/642,321, filed Jan. 7, 2005, U.S. Provisional Application No. 60/643,556, filed Jan. 13, 2005, and U.S. Provisional Application No. 60/650,302, filed Feb. 5, 2005. The disclosures of which are all incorporated herein by reference in their entireties for all purposes.

FIELD OF THE INVENTION

The present invention generally relates to devices and surgical methods for the treatment of various types of spinal pathologies. More specifically, the present invention is directed to several different types of highly configurable and anatomically adaptable spinal joint replacement prostheses and surgical procedures for performing spinal joint replacements.

BACKGROUND OF THE INVENTION

The human spinal column 10, as shown in FIG. 1, is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five fused vertebrae, known as S1-S5, while the coccygeal region contains four fused vertebrae, known as Co1-Co4.

FIG. 2 depicts a superior plan view of a normal human lumbar vertebra 12. Although human lumbar vertebrae vary somewhat according to location, they share many common features. Each vertebra 12 includes a vertebral body 14. Two short boney protrusions, the pedicles 16, extend backward from each side of the vertebral body 14 to form a vertebral arch 18.

At the posterior end of each pedicle 16, the vertebral arch 18 flares out into broad plates of bone known as the laminae 20. The laminae 20 fuse with each other to form a spinous process 22. The spinous process 22 serves for muscle and ligamentous attachment. A smooth transition from the pedicles 16 to the laminae 20 is interrupted by the formation of a series of processes.

Two transverse processes 24 thrust out laterally, one on each side, from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the laminae 20. The superior articular processes 26 are sharp oval plates of bone rising upward on each side of the vertebrae, while the inferior processes 28 are oval plates of bone that jut downward on each side.

The superior and inferior articular processes 26 and 28 each have a natural bony structure known as a facet. The superior articular facet 30 faces medially upward, while the inferior articular facet 31 (see FIG. 3) faces laterally downward. When adjacent vertebrae 12 are aligned, the facets 30 and 31 capped with a smooth articular cartilage and encapsulated by ligaments, interlock to form a facet joint 32, also known as a zygapophyseal joint.

The facet joint 32 is composed of a superior facet and an inferior facet. The superior facet is formed by the vertebral level below the joint 32, and the inferior facet is formed by the vertebral level above the joint 32. For example, in the L4-L5 facet joint, the superior facet of the joint 32 is formed by bony structure on the L5 vertebra (i.e., a superior articular surface and supporting bone 26 on the L5 vertebra), and the inferior facet of the joint 32 is formed by bony structure on the L4 vertebra (i.e., an inferior articular surface and supporting bone 28 on the L4 vertebra).

An intervertebral disc 34 between each adjacent vertebra 12 permits gliding movement between the vertebrae 12. The structure and alignment of the vertebrae 12 thus permit a range of movement of the vertebrae 12 relative to each other.

Back pain, particularly in the "small of the back" or lumbosacral (L4-S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called "pinched" nerves, or nerve compression or impingement. The result is pain, misaligned anatomy, and a corresponding loss of mobility. Pressure on nerves can also occur without facet joint pathology, e.g., a herniated disc.

One type of conventional treatment of facet joint pathology is spinal stabilization, also known as intervertebral stabilization. Intervertebral stabilization prevents relative motion between the vertebrae. By preventing movement, pain can be reduced. Stabilization can be accomplished by various methods. One method of stabilization is spinal fusion. Another method of stabilization is fixation of any number of vertebrae to stabilize and prevent movement of the vertebrae.

Another type of conventional treatment is decompressive laminectomy. This procedure involves excision of part or all of the laminae and other tissues to relieve compression of nerves.

These traditional treatments are subject to a variety of limitations and varying success rates. None of the described treatments, however, puts the spine in proper alignment or returns the spine to a desired anatomy or biomechanical functionality. In addition, stabilization techniques hold the vertebrae in a fixed position thereby limiting a person's mobility and can compromise adjacent structures as well.

SUMMARY OF THE INVENTION

Prostheses, systems and methods exist which can maintain more spinal biomechanical functionality than the above discussed methods and systems and overcome many of the problems and disadvantages associated with traditional treatments for spine pathologies. One example of such prosthesis is shown in FIG. 4. FIG. 4 shows an artificial cephalad and caudal facet joint prosthesis 36 and 50 for replacing a natural facet joint. Cephalad joint prosthesis 36 replaces the inferior facet of a natural facet joint. Cephalad prosthesis 36 has a bearing element 38 with a bearing surface 40. Caudal joint prosthesis 50 replaces the superior facet of a natural facet joint. Caudal prosthesis 50 has a bearing element 52 with a bearing surface 54. Conventional fixation elements 56 attach cephalad and caudal facet joint prostheses 36 and 50 to a vertebra in an orientation and position that places bearing surface 40 in approximately the same location as the natural facet joint surface the prosthesis replaces. The prosthesis may also be placed in a location other than the natural facet joint location.

The prosthesis illustrated in FIG. 4 addresses the immediate problem of facet joint degeneration and restores biomechanical motion. However, this exemplary prosthesis, in addition to others, would benefit from design features having more modular components or a design that lends itself to attaching to the spinal bone in a greater variety of orientations and/or locations. In general, the desire for these kinds of design changes is referred to generally as prosthesis customization.

Prosthesis customization to patient specific disease state and anatomy are among the challenges faced when implanting a prosthesis. The challenges are amplified in the implantation of spinal prostheses that restore facet biomechanical function and vertebral body motion. Current prostheses designs have not provided prosthesis systems having modular designs that are configurable and adaptable to patient specific disease state and anatomy.

There is a need in the field for prostheses and prosthetic systems having configurable designs and that are adaptable to a wide variety of spinal anatomy and disease states to replace injured and/or diseased facet joints, which cause, or are a result of, various spinal diseases. There is also a need for surgical methods to install such prostheses. Additionally, there is also a need for prostheses and prosthetic systems to replace spinal fusion procedures.

In one embodiment of the present invention there is provided a facet joint prosthesis to replace, on a vertebral body, a portion of a natural facet joint having a support component sized to span a portion of the vertebral body and adapted to receive a pair of prosthetic facet elements; and a pair of prosthetic facet elements positionable relative to the support component to replace a portion of a natural facet joint. In a further embodiment the support component is sized to span a portion of a vertebral body between a left lamina and a right lamina or between the left pedicle and the right pedicle. In still further embodiments, there is a kit comprising a plurality of support components having different lengths. In another embodiment, the support component is further adapted to have an adjustable width. In yet another embodiment, the support component is secured to the vertebral body, and in another, the support component is secured to an adjacent vertebral body. In yet another alternative embodiment, the prosthetic facet elements are positioned relative to the support component to provide a symmetric anatomical solution and/or an asymmetrical anatomical solution.

In still another embodiment, the support component has an opening adapted to receive the prosthetic facet elements. In another embodiment, the prosthetic facet elements are slideable along the width of the support component, the prosthetic facet elements may be fixed in a pre-ordained position medial of the typical anatomic location and/or the prosthetic facet elements may be fixed in a pre-ordained position lateral of any typical anatomic location. In another embodiment, the ends of the support component are adapted to receive an opening in each of the pair of prosthetic facet elements. In another embodiment, the pair of prosthetic facet elements is selected from a plurality of prosthetic facet elements each having an opening with a different depth. In another embodiment, the facet joint prosthetic facet evenly distributes the weight and/or static/dynamic forces on the vertebral body using the support component. In another embodiment, the pair of prosthetic facet elements are caudal facet elements. In another embodiment, the pair of prosthetic facet elements are cephalad facet elements.

In another alternative embodiment, there is provided an adaptable spinal facet joint prosthesis, having a crossbar having a first end and a second end; a pair of cephalad prosthesis elements each having a bone engaging end and an end adapted to couple to the crossbar; and a pair of caudal prosthesis elements each having a surface adapted to receive a crossbar end and a fixation element. In one embodiment, the distance between the crossbar first end and second end is adjustable. In another alternative embodiment, the bone engaging end of at least one of the pair of cephalad prosthesis elements is disengagably coupled to the at least one of the pair of cephalad prosthesis elements. In another embodiment, at least one of the pair of cephalad prosthesis elements or at least one of the pair of caudal prosthesis elements comprises an anti-rotation feature. In another alternative embodiment, the height above the crossbar of a part of a cephalad prosthesis element may be adjusted by moving the cephalad prosthesis element relative to the crossbar cephalad prosthesis portion engaging portion. In another alternative embodiment, the crossbar mount posterior height is less than the posterior height of an adjacent spinous process when the adaptable spinal facet joint is implanted in a body.

In yet another alternative embodiment, there is provided a spinal prosthesis, comprising: a first cephalad prosthesis element and a second cephalad prosthesis element; a first caudal prosthesis and a second caudal prosthesis; and a crossbar element connected to the first and second cephalad prosthesis elements, the crossbar element having a first end in contact with the first caudal prosthesis and a second end in contact with the second caudal prosthesis wherein at least one of the first cephalad prosthesis element, the second cephalad prosthesis element, the caudal prosthesis, the second caudal prosthesis and the crossbar element having a configurable portion.

In another embodiment, there is provided a spinal prosthesis, comprising a pair of cephalad prosthesis members each comprising a distal end for securing to a portion of the spine and a proximal end comprising a bearing element; a pair of caudal prosthesis members each comprising a fixation element for securing to a portion of a spine and a bearing element adapting to engage the cephalad prosthesis member bearing element; and a crossbar connected between the cephalad prosthesis members.

In another embodiment, there is provided an adaptable spinal prosthesis, comprising a pair of cephalad elements connected to act in unison with a pair of cephalad arms, each of said cephalad arms comprising a proximal end, a distal end and an elbow between the proximal end, and a pair of caudal bearing elements adapted to engage with the pair of cephalad bearing elements.

In yet another embodiment, there is provided a caudal bearing of a spinal prosthesis, comprising a caudal bearing element having a first surface adapted to engage a cephalad bearing and a second surface adapted to engage the fixation element; and a fixation element having a preconfigured surface adapted to engage with the second surface whereby when the preconfigured surface is engaged with the second surface the first surface maintains an orientation to engage a cephalad bearing and the orientation of the fixation element relative to the caudal bearing element is changed to a desired orientation.

In another alternative embodiment, there is provided a spinal prosthesis having a crossbar having a first end and a second end; a pair of cephalad prosthesis elements having a first end for engaging a vertebrae and a second end; a pair of caudal prosthesis elements each having a surface to slidably engage a crossbar end; and a single crossbar mount for securing the second end of each of the pair of cephalad prosthesis elements to the crossbar.

In yet another embodiment, there is provided a crossbar that is adaptable and configured for placement joining two cephalad elements, or alternatively, two caudal elements. Additional crossbar embodiments provide different attachment mechanisms and locations between the elements. Moreover, additional embodiments provide adaptability of one or more cephalad elements, one or more caudal elements and/or one or more crossbar elements.

In another embodiment, there is provided a modular spinal prosthesis kit and an associated surgical method of selecting from the modular spinal prosthesis kit configurable prosthesis elements that, separately and in combination, provide an adaptable spinal prosthesis corresponding to the prosthetic needs of the patient. The kit provides a variety of various sized cephalad and caudal prosthesis as well as various crossbars. The method includes selecting components from the kit having the desired size, angular orientation and anatomical orientation that correspond to the prosthetic needs of the patient. In additional embodiments, there is provided a method of adapting a prosthesis to an individual's anatomy wherein the adaptability is achieved by selecting from a subset of different sizes and configurations of prosthetic components.

In yet another embodiment, there is provided a method of adapting a spinal prosthesis by selecting the configuration of a prosthesis based in part on the resulting anatomical features of a patient post-resection or post facetectomy. The various adaptable and configurable prosthesis form a modular prosthesis system containing a number of different component configurations and orientations that, depending on disease state at a particular site, may or may not require recision of a portion of the vertebrae/facet including using a method to form a surface for mounting the prosthesis. Based on the surface geometry created and the disease state/anatomy, selectable prosthesis such as a caudal, a cephalad and/or a crossbar element can be chosen to replace and/or accommodate the removed portion of the spine/facet joint.

In yet another embodiment there is provided a crossbar mount that utilizes compression fittings. In another alternative embodiment, there is provided a crossbar mount having a top cap configured to engage with variable depth fittings on the mount body.

In another embodiment, there are provided several alternative cephalad components having modular, configurable and adaptable features including but not limited to arm length, tip length, surface texture and crossbar engagement end and bone engagement end.

In another embodiment, there are provided several alternative caudal components having modular, adaptable and configurable features including but not limited to stem length, inclusion of anti-rotation elements, caudal bearing angle adjustments, caudal bearing shape, size and fittings.

In another embodiment, there are provided several alternative crossbar components having modular, adaptable and configurable features including but not limited to crossbars of fixed length, adjustable length, spherical bearings, non-spherical bearings, crossbar mount engagement configurations, cylindrically shaped crossbars, elongate crossbars having non-circular cross sections (including crossbar mount designs unique to engaging across a crossbar and a cephalad arm). Some embodiments contemplate the use of a polyaxial type connector used in combination with a crossbar mount joining a crossbar and a cephalad arm or in other uses in the context of modular, adaptable and configurable prosthesis.

In another alternative embodiment, a modular spinal prosthesis is adapted to an individual anatomy by selecting and positioning the one or more caudal elements and then based on the caudal component placement and the existing anatomy, select crossbar and cephalad components to conform to the caudal prosthesis component placement. In another alternative embodiment, a modular spinal prosthesis is adapted to an individual anatomy by selecting and positioning the one or more cephalad elements and then based on the cephalad component placement and the existing anatomy, select crossbar and caudal components to conform to the cephalad prosthesis component placement.

In additional alternative embodiments, there are provided different components, methods and configurations to provide improved tissue shielding capabilities, such as for example, basing the selection of the modular components on reducing the occurrence of tissue being caught in the prosthesis. In one specific embodiment, the relative positions are modified such as by reversing the caudal and the cephalad bearings to protect tissue from getting caught in the contacting arms.

Another aspect of the present invention provides an adaptable spinal facet joint prosthesis that includes a pedicle fixation element; a laminar fixation element; and a facet joint bearing surface (such as a cephalad or caudal facet joint bearing surface) having a location adaptable with respect at least one of the pedicle fixation element and the laminar fixation element. In some embodiments, the prosthesis further includes a facet joint bearing surface support, with the laminar fixation element and the pedicle fixation element extending from the facet joint bearing surface support.

In some embodiments, the laminar fixation element is adapted to extend through a lamina portion of a vertebra. In some embodiments, the laminar fixation element is adapted to contact a resected laminar surface. The laminar fixation element and pedicle fixation element may be adapted to resist rotation of the bearing surface. The prosthesis may include both cephalad and caudal facet joint bearing surfaces. One or both of the fixation elements may also include bone ingrowth material.

Another aspect of the invention provides a method of implanting an adaptable spinal facet joint prosthesis including the following steps: determining a desired position for a facet joint bearing surface; attaching a prosthesis having a facet joint bearing surface to a pedicle portion of a vertebra and a lamina portion of a vertebra to place the facet joint bearing surface in the desired position. In embodiments in which the prosthesis also includes a pedicle fixation element and a laminar fixation element, the method may include the step of adjusting a location of the facet joint bearing surface with respect to at least one of the pedicle fixation element and the laminar fixation element. In some embodiments, the attaching step may include the step of extending a laminar fixation element through a portion of the lamina portion of the vertebra. In some embodiments, the method also includes the step of resecting the vertebra to form a lamina contact surface, with the attaching step including the step of attaching a laminar fixation element to the lamina contact surface.

Yet another aspect of the invention provides a facet joint prosthesis implant tool including a tool guide adapted to guide a vertebra cutting tool, such as a lamina cutting tool; and first and second fixation hole alignment elements extending from the saw guide. In some embodiments, the tool also has an adjustable connection between the tool guide and at least one of the first and second fixation hole alignment elements. In some embodiments, the first fixation hole alignment element is adapted to be placed in a cephalad vertebra fixation hole and the second fixation hole alignment element is adapted to be place in a caudal vertebra fixation hole.

Still another aspect of the invention provides a facet joint prosthesis including a facet joint bearing surface; a vertebral fixation element adapted to attach to a vertebra to support the facet joint bearing surface; and a prosthetic disc migration prevention member adapted to prevent migration of a prosthetic disc disposed adjacent to the vertebra. In some embodiments, the prosthetic disc migration prevention member is adapted to contact, and perhaps attach to, the prosthetic disc. In some embodiments, the fixation element is a first fixation element and the vertebra comprises a first vertebra, the prosthesis further including a second fixation element adapted to attach to a second vertebra adjacent to the prosthetic disc to support the bearing surface.

Still another aspect of the invention provides a system for treating spinal pathologies including an intervertebral disc prosthesis in combination with an adaptable facet joint prosthesis comprising a crossbar having a first end and a second end; a pair of cephalad prosthesis elements each having a bone engaging end and an end adapted to couple to the crossbar; and a pair of caudal prosthesis elements each having a surface adapted to receive a crossbar end and a fixation element.

Yet another aspect of the invention provides a system for treating spinal pathologies including an intervertebral disc prosthesis in combination with a spinal prosthesis, comprising: a first cephalad prosthesis element and a second cephalad prosthesis element; a first caudal prosthesis and a second caudal prosthesis; and a crossbar element connected to the first and second cephalad prosthesis elements, the crossbar element having a first end in contact with the first caudal prosthesis and a second end in contact with the second caudal prosthesis wherein at least one of the first cephalad prosthesis element, the second cephalad prosthesis element, the caudal prosthesis, the second caudal prosthesis, and the crossbar element having a configurable portion.

Still another aspect of the invention provides a system for treating spinal pathologies including a facet joint prosthesis to replace, on a vertebral body, a portion of a natural facet joint, comprising: a support component sized to span a portion of the vertebral body and adapted to receive a pair of prosthetic facet elements; and a pair of prosthetic facet elements positionable relative to the support component to replace a portion of a natural facet joint.

Another aspect of the invention provides a system for treating spinal pathologies including an intervertebral disc prosthesis in combination with an adaptable spinal facet joint prosthesis, comprising: a crossbar having a first end and a second end; a pair of cephalad prosthesis elements each having a bone engaging end and an end adapted to couple to the crossbar; and a pair of caudal prosthesis elements each having a surface adapted to receive a crossbar end and a fixation element.

Still another aspect of the invention provides a system for treating spinal pathologies including an intervertebral disc prosthesis in combination with a spinal prosthesis, comprising: a first cephalad prosthesis element and a second cephalad prosthesis element; a first caudal prosthesis and a second caudal prosthesis; and a crossbar element connected to the first and second cephalad prosthesis elements, the crossbar element having a first end in contact with the first caudal prosthesis and a second end in contact with the second caudal prosthesis wherein at least one of the first cephalad prosthesis element, the second cephalad prosthesis element, the caudal prosthesis, the second caudal prosthesis, and the crossbar element having a configurable portion.

Yet another aspect of the invention provides a system for treating spinal pathologies including an intervertebral disc prosthesis in combination with a spinal prosthesis, comprising: a pair of cephalad prosthesis members each comprising a distal end for securing to a portion of the spine and a proximal end comprising a bearing element; a pair of caudal prosthesis members each comprising a fixation element for securing to a portion of a spine and a bearing element adapting to engage the cephalad prosthesis member bearing element; and a crossbar connected between the cephalad prosthesis members.

These and other features and advantages of the inventions are set forth in the following description and drawings, as well as in the appended claims.

BRIEF DESCRIPTION OF THE DRAWINGS

FIGS. 7, 8, 8A-8F are various views of several alternative embodiments of a caudal prosthesis.

FIGS. 9, 9A-C, 10A-B, 11A-B are various views of several alternative crossbar embodiments;

FIGS. 12A-12D and 13A-B are various views of various caudal bearing cup embodiments;

FIG. 14 is a perspective view of an embodiment of a cephalad prosthesis element;

FIG. 15 is an embodiment of an assembled modular prosthesis of the present invention;

FIG. 15A an alternate embodiment of an assembled modular prosthesis;

FIGS. 16A-16B illustrate the internal components of an embodiment of a crossbar mount.

FIGS. 16C-16F illustrate an alternative embodiment of a crossbar mount;

FIG. 18 illustrates a kit embodiment of a modular prosthesis of the present invention;

FIGS. 20, 21, 22, 23 and 24 illustrate a method of implanting an embodiment of a modular prosthesis of the present invention;

FIG. 20A through 20C depict various embodiments of a prosthesis suitability or "GO-NO-GO" gauge;

FIGS. 20D and 20E depict embodiments of a variable depth drill and rongeur;

FIGS. 22C and 23B depict embodiments of compression devices for setting press-fits between various components;

FIG. 23A depicts an embodiment of a cross arm measuring instrument;

FIG. 25 is a section view of the implanted modular prosthesis of FIG. 24;

FIG. 25A is a section view of the caudal portion of the implanted prosthesis of FIG. 25;

FIG. 25B is a section view of an implanted modular prosthesis showing resection of a spinous process to accommodate a crossbar;

FIGS. 26A-26B illustrate an alternative embodiment of a modular prosthesis is an alternative crossbar mount;

FIGS. 30A-30B illustrate alternative crossbar mount embodiments;

FIGS. 31A-31E illustrate alternative crossbar embodiments that join the cephalad arms;

FIGS. 32A-32D illustrate alternative crossbar embodiments that join the cephalad bearings;

FIGS. 33A-34C, 34A-34B, 35A-D, 36A-36B illustrate various views of fixation members having of anti-rotations features; and FIG. 36C illustrates an embodiment of cephalad arms having anti-rotation features and a crossbar;

FIG. 37 illustrates an embodiment of a facet joint replacement prosthesis comprising a polymer block;

The invention may be embodied in several forms without departing from its spirit or characteristics. The scope of the invention is defined by the appended claims, rather than in the specific embodiments preceding them.

DETAILED DESCRIPTION OF THE INVENTION

Embodiments of the present invention provide modular spinal prosthesis that are configurable and/or adaptable prostheses, systems and methods designed to replace natural facet joints and, in some embodiments, part of the lamina at virtually all spinal levels including L1-L2, L2-L3, L3-L4, L4-L5, L5-S1, T11-T12, and T12-L1 (as well as virtually all other spinal levels), using attachment mechanisms for securing the prostheses to the vertebrae. The prostheses, systems, and methods help establish a desired anatomy to a spine and return a desired range of mobility to an individual. The prostheses, systems and methods also help lessen or alleviate spinal pain by relieving the source of nerve compression, impingement and/or facet joint pain.

Figure 1:
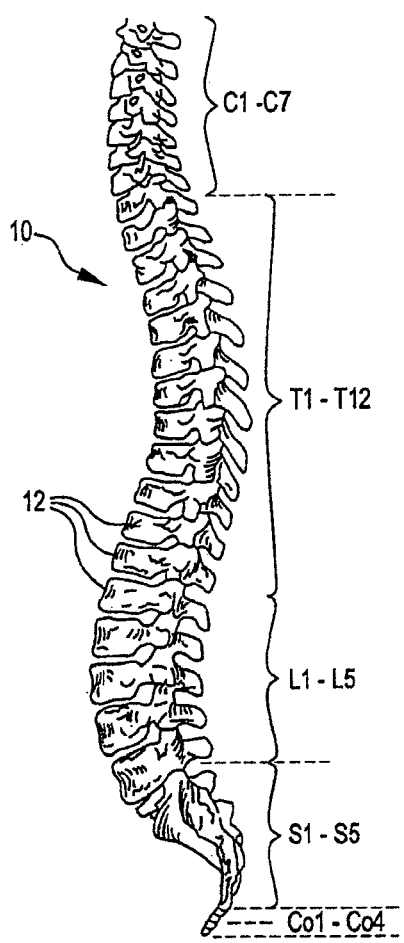
FIG. 1 is a lateral elevation view of a normal human spinal column.
Figure 2:
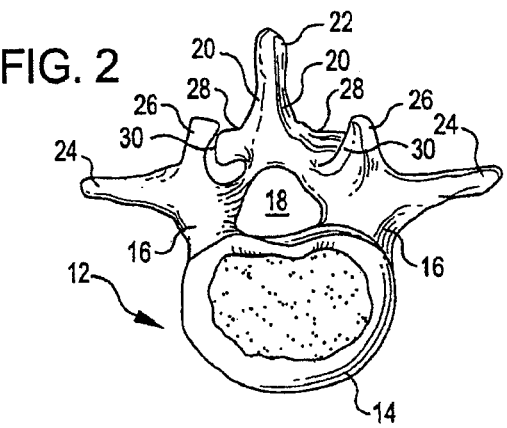
FIG. 2 is a superior view of a normal human lumbar vertebra.
Figure 3:
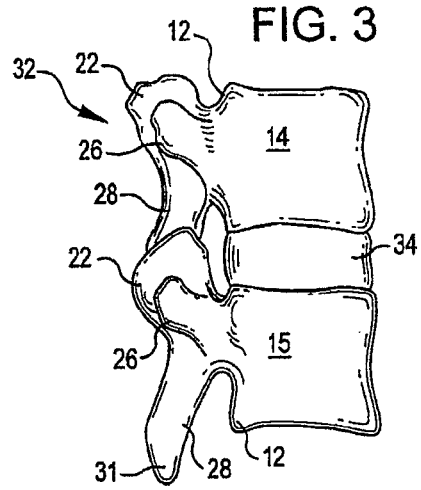
FIG. 3 is a lateral elevation view of vertebral facet joint.
Figure 4:
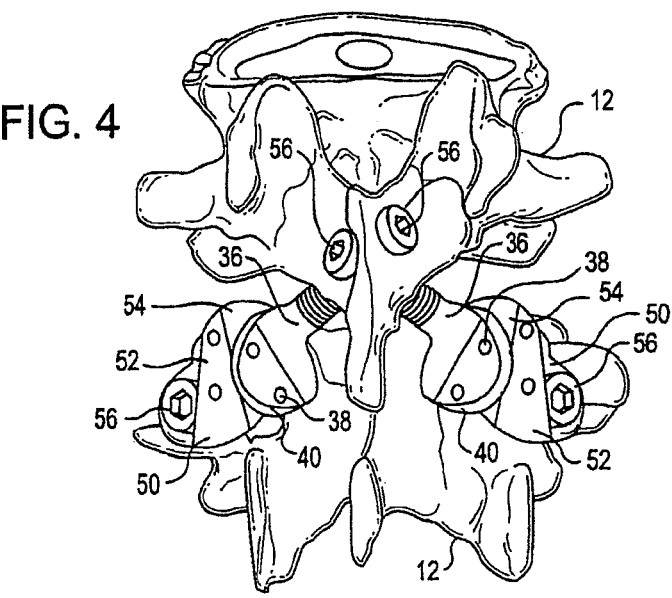
FIG. 4 is a perspective view of a spinal prosthesis.

For the sake of description herein, the prostheses that embody features of the invention are identified as either "cephalad" or "caudal" with relation to the portion of a given natural facet joint they replace. As previously described, a natural facet joint, such as facet joint 32 (FIG. 3), has a superior facet 22 and an inferior facet 28. In anatomical terms, the superior facet of the joint is formed by the vertebral level below the joint, which can thus be called the "caudal" portion of the facet joint because it is closer to the feet of the person. The inferior facet of the facet joint is formed by the vertebral level above the joint, which can thus be called the "cephalad" portion of the facet joint because it is closer to the head of the person. Thus, a prosthesis that, in use, replaces the caudal portion of a natural facet joint (i.e., the superior facet) will be called a "caudal" prosthesis. Likewise, a prosthesis that, in use, replaces the cephalad portion of a natural facet joint (i.e., the inferior facet) will be called a "cephalad" prosthesis.

When the processes on one side of a vertebral body are spaced and/or oriented differently from those on the other side of the same body, the prostheses on each side would desirably be of differing sizes and/or orientations as well. Moreover, it is often difficult and/or impossible for a surgeon to determine the precise size and/or shape necessary for a prosthesis until the surgical site has actually been prepared for receiving the prosthesis. In such case, the surgeon typically needs a family of prostheses possessing differing sizes and/or shapes immediately available during the surgery. The surgeon cannot typically wait for a custom-made device to be created during the surgery. In view of this need, embodiments of the spinal prosthesis of the present invention are modular designs that are either or both configurable and adaptable. Additionally, the various embodiments disclosed herein may also be formed into a "kit" of modular components that can be assembled in situ to create a custom prosthesis.

Configurable refers to the modular design of a prosthesis. For example, a configurable modular prosthesis design allows for individual components to be selected from a range of different sizes and utilized within a modular prosthesis. One example of size is to provide caudal and cephalad stems of various lengths. A modular prosthesis design allows for individual components to be selected for different functional characteristics as well. One example of function is to provide stems having different surface features and/or textures to provide anti-rotation capability. Another example would be having components of different shapes, such as stems incorporating different angulations and/or shapes. Other examples of the configurability of modular prosthesis of the present invention as described in greater detail below.

Adaptable refers to the capacity of embodiments of the modular prosthesis of the present invention to select and position configurable components such that the resulting spinal prosthesis will conform to a specific anatomy or desired surgical outcome. The adaptable aspect of embodiments of the present invention provides the surgeon with customization options during the implantation procedure. It is the adaptability of the present prosthesis systems that also provides adjustment of the components during the implantation procedure to ensure optimal conformity to the desired anatomical orientation or surgical outcome. As described in greater detail in the illustrative embodiments that follow, an adaptable modular prosthesis of the present invention allows for the adjustment of various component to component relationships. One example of a component-to-component relationship is the rotational angular relationship between a crossbar mount and the crossbar. Other examples of the adaptability of modular prosthesis of the present invention as described in greater detail below. Configurability may be thought of as the selection of a particular size and/or shape of a component that together with other component size/shape selections results in a "custom fit" prosthesis. Adaptability then refers to the implantation and adjustment of the individual components within a range of positions in such a way as to fine tune the "custom fit" prosthesis for an individual patient. The net result is that embodiments of the modular, configurable, adaptable spinal prosthesis of the present invention allow the surgeon to alter the size, shape, orientation and/or relationship between the various components of the prosthesis to fit the particular needs of a patient during the actual surgical procedure. It should be understood that, in many respects, the configurability and adaptability aspects of a component or set of components can overlap to varying degrees.

Figure 5:
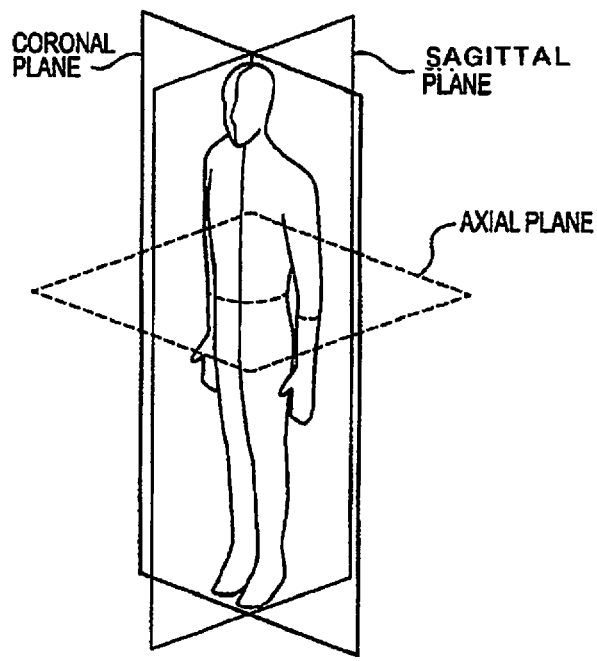
FIG. 5 is a perspective view of the anatomical planes of the human body.

Configurability and adaptability will at times be described in relation to an anatomical plane of the body or between a plane or plane and a component or components. There are three anatomical planes generally used to describe the human body: the axial plane, the sagittal plane and the coronal plane (see FIG. 5). Various embodiments of the spinal prosthesis of the present invention may be configurable and variable with respect to a single anatomical plane or with respect to two or more anatomical planes. For example, a component may be described as lying within and having adaptability in relation to a single plane. For example, a stem may be positioned in a desired location relative to an axial plane and may be moveable between a number of adaptable positions or within a range of positions. Similarly, the various components can incorporate differing sizes and/or shapes in order to accommodate differing patient sizes and/or anticipated loads.

Figure 6:
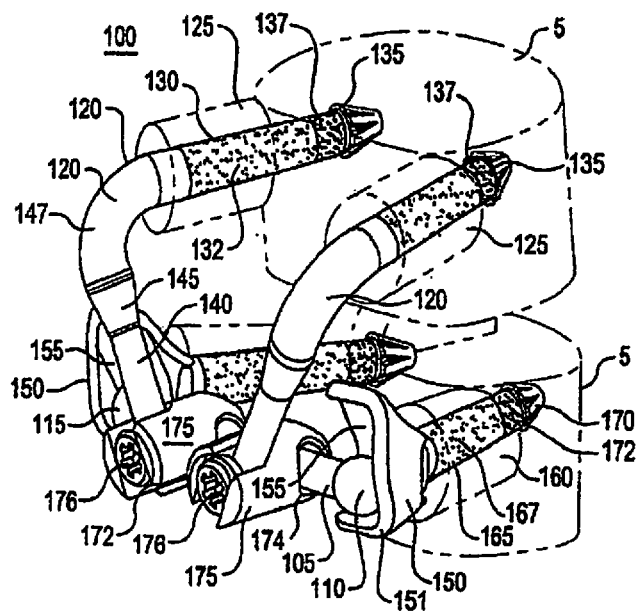
FIG. 6 is an perspective view of an embodiment of a modular spinal prosthesis of the present invention.

FIG. 6 is an isometric view of a modular, configurable and adaptable spinal prosthesis 100 according to one embodiment of the present invention. The spinal prosthesis 100 is illustrated implanted into vertebral bodies 5. The main components of spinal prosthesis 100 will be introduced with reference to FIG. 6. Each of the components will then be described in turn.

The spinal prosthesis 100 includes a crossbar 105, a pair of cephalad prostheses 120 and a pair of caudal prostheses 150. In this exemplary embodiment the superior facets are replaced by the cooperative operation of the crossbar 105, the cephalad prosthesis 120 and the adaptable crossbar mounts 175 that join the cephalad prosthesis 120 to the crossbar 105. The inferior facets are replaced by the caudal prosthesis 150. As described in greater detail below, the components of the spinal facet prosthesis 100 are designed to provide appropriate configurability and adaptability for the given disease state, patient specific anatomy, functionality needed and spinal level where the implant occurs.

Figure 9B:
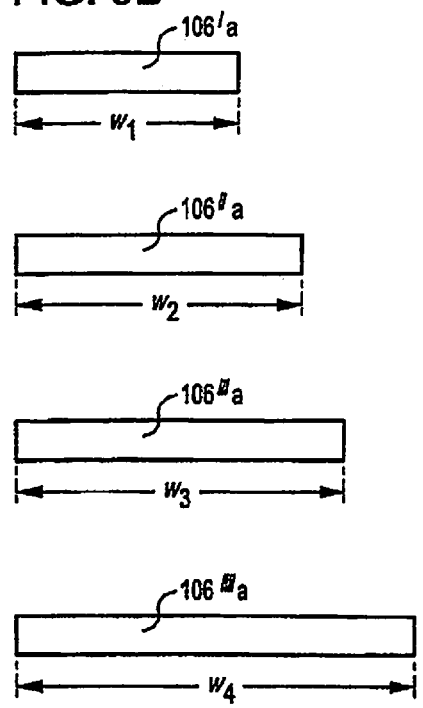
Figure 9C:
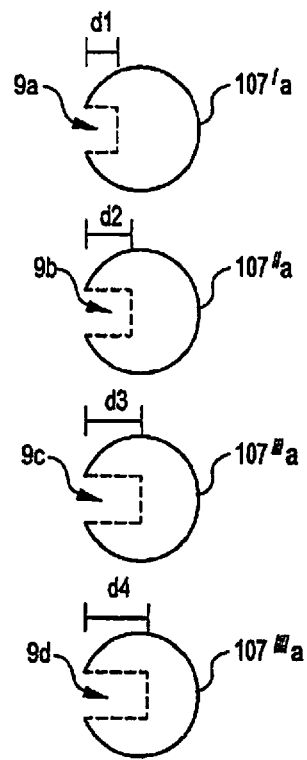

The crossbar 105, in a first embodiment, has a first end 110 and a second end 115. In the illustrated embodiment the crossbar 105 is a two piece bar where the first end 110 is attached to a threaded male portion 104 having threads 109. The crossbar second end 115 is attached to a threaded female portion 106 sized to receive the threads 109. As will be described in greater detail below, the threaded ends allow for the width of the crossbar to be adjusted to mate with the width between caudal bearings 150 (FIG. 9). Additional alternative embodiments of the crossbar 105 could include a series of solid crossbars of varying widths and/or thicknesses (See FIGS. 9A, 9B and 9C), or an adjustable crossbar having some form of locking or biasing mechanism (such as a spring-loaded tensioner or detent mechanism, etc.).

A pair of cephalad prosthesis elements 120 are also illustrated in the exemplary embodiment of the configurable and adaptable spinal prosthesis 100 of the present invention. Each cephalad prosthesis element 120 includes a bone engaging end 125 and an end 140 adapted to couple to the crossbar. The cephalad end 140 adapted to engage the crossbar includes an arm 145 and an elbow 147. The cephalad end 140 is attached to the crossbar using the crossbar mount 175. The bone engaging end 125 includes a cephalad stem 130 and a distal tip 135. The cephalad stem 130 and the distal tip 135 are threaded or otherwise configured to engage bone. (Alternatively, the distal tip 135 could be formed integrally with the cephalad stem 130, of the same or a different material as the cephalad stem 130.) The illustrated embodiment of the cephalad stem 130 has surface features 132. Surface features 132 may be, for example, a textured surface or other surface such as, for example, surface features to assist in bony in-growth. Similarly, the illustrated embodiment of the distal tip 135 has surface features 137.

The crossbar mount 175 is a connection structure to couple the cephalad prosthesis elements 120 to the crossbar 105. In the illustrated embodiment, the crossbar mount 175 includes a cephalad arm engaging portion 172, a cross bar engaging portion 174 and a fixation element 176. As will be described in greater detail below, embodiments of the crossbar mount 175 provide adaptability between the cephalad prosthesis elements 120 and the crossbar 105 and the loading characteristics of the crossbar ends 110, 115 and the caudal prosthesis 150.

Having provided an overview of the main components of an embodiment of a configurable and adaptable spinal prosthesis, each of the components will be described in greater detail.

Caudal Prosthesis Configurability and Adaptability

A pair of caudal prosthesis elements 150 is illustrated in the exemplary embodiment of the configurable and adaptable spinal prosthesis 100 of the present invention. Each of the caudal prosthesis elements 150 includes a caudal cup 151 and a fixation element 160. The caudal cup 151 includes a surface 155 adapted to receive a crossbar end and a surface 157 (not shown) to engage the caudal stem head engaging surface 163 (not shown). The fixation element 160 includes a caudal stem 165 and a distal tip 170. (Alternatively, the distal tip 170 can be formed integrally with the caudal stem 165, of the same or a different material as the caudal stem 165.) The caudal stem 165 and distal tip 170 can be threaded or otherwise configured to engage bone. Additionally, the caudal stem 165 and the distal tip 170 may include textured or otherwise functional surface features 167. In some embodiments, the features on the caudal stem 165 are different from the features on the distal tip 170.

The configurability and adaptability of the caudal prosthesis 150 will now be described with reference to FIGS. 7-8F. FIG. 7 illustrates an isometric view of a caudal prosthesis element 150. The caudal prosthesis element 150 includes a caudal cup 151 having a surface 155 adapted to receive a crossbar end 105 or 110. The caudal cup 151 also has a surface 157 adapted to receive the fixation element stem head 162. The fixation element 160 has a caudal stem 165 and a distal end or tip 170 (as previously noted, the tip 170 could be formed integrally with the stem 165, or can be attachable to the stem 165). The surfaces of each may include textures 167 that may be the same (as illustrated) or different. The textured surfaces of the caudal stem 165 and tip 170 include textures to, for example, promote bony in growth and/or increase the strength of the mechanical bond with fixation cement (adhesion).

The caudal fixation element 160 may be secured directly into the vertebral body, or can be attached and/or "fixed" using a supplemental fixation material such as bone cement, allograft tissue, autograft tissue, adhesives, osteo-conductive materials, osteo-inductive materials and/or bone scaffolding materials. In one embodiment, the fixation element 160 is enhanced with a bony in-growth surface. Examples of such surfaces are created using sintering processes (including the use of a porous coating on the substrate of the implant), metal deposition, mechanical/chemical material addition/removal, and/or chemical etching (Tecomet Corporation of Woburn, Mass.) which can help fix the fixation element within a vertebra. The bony in-growth surface can cover a portion or all of the caudal stem 165 and/or the distal tip 170. In one embodiment, the surface treatment extends approximately halfway from the distal tip 170 along the stem 165.

Further details of the caudal prosthesis element 150 will be described with reference to FIG. 8. The caudal cup 151 has a surface 157 adapted to receive the fixation element stem head 162. The fixation element stem head 162 has a surface 163 adapted to engage with the surface 157. As will be further described below, the caudal fastener 160 and caudal cup 151 are first connected together, and then the caudal fastener 160 is secured to the targeted vertebrae. (Of course, if desired, the caudal fastener 160 could be implanted first and then the caudal cup 151 attached thereto afterwards.) Variations in the configuration and engagement of the surfaces 157, 163 therefore determine the orientation of the caudal cup 151 and the bearing surface 155. The shape and orientation of the bearing surface 155 is a factor in how the cephalad and caudal bearing elements interact and the overall performance of various spinal prosthesis embodiments of the present invention.

One challenge confronted by embodiments of the caudal prosthesis is that the caudal stem provides at least two significant functions. First, the caudal stem is an anchor for the caudal prosthesis portion of the spinal implant. As an anchor, the caudal stem requires an engaging placement with sufficient quantity and quality of spinal bone—bone which can be of varying quality, quantity and anatomical orientation. To meet this challenge, caudal stem of the present invention may be provided in a sufficiently large array of angular orientations, shapes, sizes and lengths to reach and sufficiently engage with the targeted spinal bone. For example, if a patient has thin lamina or is in an excessive disease state requiring removal of spinal bone, then the caudal stem may benefit from modifications to length and orientation (as well as anti-rotation projections, clips, etc.) to reach one or more acceptable bone mass(es) for fixation. In a similar manner, the caudal stem should also resist unwanted rotation. Second, the caudal stem is the attachment point for the caudal cup. Based on the desired spinal prosthesis configuration, there will be a desired caudal cup orientation to provide proper engagement and alignment between the caudal cup and other prosthesis components, such as for example, a cephalad bearing. Alteration of one or both of the surfaces 157, 163 may be utilized to make up the difference between the position and orientation of the caudal stem after implantation or meeting the anchoring function and the position and orientation of an attachment point for the caudal cup. The position and orientation of the attachment point for the caudal cup provides an attachment point that provides the desired orientation of the caudal bearing surface 155.

For purposes of explaining the configurability and adaptability of the caudal prosthesis, the caudal stem is described as varying in relation to the caudal cup. This description and the caudal cup embodiments that follow illustrate the caudal cup in a desired orientation. As such, the caudal cup appears fixed and the variation and adaptability of the caudal prosthesis is apparent by the different positions of the caudal stem. "Variation" refers to the relationship of the caudal stem into the spinal bone where the stem is implanted. As a result of disease state, anatomy and other factors, there may be only a few possible sites and/or orientations available for caudal stem implantation. Based on the position selected/available, the caudal stem will have a resulting orientation relative to the caudal cup. Differences, if any, between the orientation of the caudal stem head 162 and the caudal cup may be accounted for through advantageous alteration and combination of the surfaces 157, 163. This aspect of caudal prosthesis configurability and adaptability provides more options to implant fixation elements while still providing a suitable engagement to provide a caudal bearing surface having a desired orientation. In operation and for a given spinal prosthesis embodiment, there is a desired orientation of the caudal cup to engage with the cephalad bearings (for any given vertebral body, there may be one or more optimal implantation locations/positions for the implant, as well as a host of non-optimal or suboptimal positions/locations/orientations). Caudal stem variability provides for the advantageous insertion angle and depth of the caudal stem into the spine to provide support of the caudal cup. While providing the proper orientation and length (depth) of a caudal stem, the stem must also provide an attachment point for the caudal cup. In some embodiments, the orientation of the caudal cup will be fixed and the caudal stem head must be configurable and adaptable to accommodate the proper alignment between the caudal cup and stem. In other embodiments, the caudal stem will be fixed and the desired caudal cup configurability and adaptability must be provided by the caudal cup surface or a combination including alterations to the caudal stem surface 163.

The illustrated reference system indicates how variation in the relationship between the surfaces 157, 163 can result in sagittal configurability and adaptability. The engagement of the surfaces 157, 163 may be altered to provide a positive sagittal variation (+θsag) or negative sagittal variation (−θsag). One of the surfaces 157, 163 may be altered to provide the entire desired sagittal variation alone or both of the surfaces 157, 163 may be altered so that the desired sagittal variation is provided by the combination of the altered surfaces.

In the exemplary embodiment of FIG. 8 the surface 157 of the caudal cup 151 has been altered to provide the desired sagittal variability taking into account the disposition of the caudal stem head 162 post caudal stem implantation. In each of the embodiments that follow, the relationship between the caudal cup surface 155 and the engaging surface 157 differ to some meaningful degree. In addition, the engaging surface 157 desirably can include sizing or features (such as a taper lock or detent) to remain engaged with the caudal stem head 162 throughout the range of spinal prosthesis motion and loading. In one disclosed embodiment, this engagement is a taper lock designed to release or "unlock" only where the caudal cup 155 moves towards the midline of the patient relative to the caudal stem (desirably, the presence of the cross-bar prevents the caudal cup from unlocking in this manner under normal loading conditions). Alternatively, the caudal stem head 162 and stem head engaging surface 163 may be modified to provide desired variation and adaptability, or a combination of different surfaces 157, 163.

In one disclosed embodiment, the various caudal cup 151 elements incorporate geometry resulting in a selectable sagittal angle of 1°, 6° or 11° as measured between the upper endplate of the caudal vertebral body and the longitudinal axis of the caudal stem when projected onto the sagittal plane. In a similar manner, the various caudal stem elements incorporate geometry resulting in a selectable axial angle of 10°, 20° or 30°, as measured between the midline of the vertebral body and the longitudinal axis of the caudal stem, as projected onto the axial plane. Desirably, some combination of these embodiments will accommodate approximately 95% of the patient population.

The length of the caudal fixation element 160 is also configurable. The length of the caudal fixation element 160 desirably determines the overall depth (do) the fixation element 160 penetrates the spinal implantation site when the prosthesis 100 is implanted. The overall depth can be determined by selecting the desired stem depth (ds) and tip depth (dt). Different stem and tip lengths are provided to ensure that virtually any desired overall depth is available. Alternatively, where the cephalad stem is of one-piece integral construction, a series of cephalad stems having different depths, such as a set of 25, 30, 40, 45, 50 and 55 mm cephalad stems, can accommodate approximately 95% of the given patient population. In addition, the desired diameter of the cephalad stems can include one or more of the following: 7 mm, 6.5 mm, 6 mm, 5.5 mm, 5 mm, 4.5 mm, 4 mm, 3.5 mm and 3 mm diameters. The optimal size will depend upon the anticipated loading, as well as the level (lumbar, thoracic and/or cervical) and size of the treated pedicle and vertebral bodies. As is also made clear in the embodiments that follow, the stem 165 and the tip 170 can be separately selectable components that are joined using any suitable attachment method available in the prosthetic arts.

In the disclosed embodiment, the tip 170 incorporates a distal flared end. This flared end desirably mechanically anchors the tip within the fixation material (and/or bone) of the vertebral body. Moreover, the reduced diameter of the stem adjacent the tip desirably increases the thickness of the mantle of the fixation material, further reducing the opportunity for the stem to migrate and/or the mantle to fracture and fatigue. In a similar manner, a series of scalloped regions 170A around the periphery of the tip 170 and/or stem desirably reduce and or prevent rotation of the cephalad stem within the mantle of fixation material.

FIG. 8A illustrates an embodiment of a caudal prosthesis element 150' having a caudal cup 151A. Caudal cup 151A includes a surface 155 adapted to receive a crossbar end 110, 115 and an embodiment of a surface 157A to engage with the caudal stem head engaging surface 163. In this embodiment of the surface 157A, the surfaces 157A, 163 engage to provide positive sagittal caudal cup-stem variation and adaptability (+θsag). This embodiment illustrates an alteration in the surface 157A to provide caudal cup-stem variation and adaptability. Note the different thickness between the caudal cup surface 155 and the engaging surface 157A (FIG. 8A) and the thickness between the caudal cup surface 155 and the engaging surface 157 (FIG. 8). As a result, when the caudal cup surface 157A is urged into position against the caudal stem engaging surface 163, the existing stem 160 deflection is taken into account in the shapes of surfaces 157, 163 so that the caudal cup 151 and surface 155 will provide the desired orientation when secured to the caudal stem head 162.

FIG. 8B illustrates an embodiment of a caudal prosthesis element 150" having a caudal cup 151B. Caudal cup 151B includes a surface 155 adapted to receive a crossbar end 110, 115 and an embodiment of a surface 157B to engage with the caudal stem head engaging surface 163. In this embodiment of the surface 157B, the surfaces 157B, 163 engage to provide negative, sagittal caudal cup-stem variation and adaptability (+θneg). This embodiment illustrates an alteration in the surface 157B to provide caudal cup-stem variation and adaptability. Note the different thickness between the caudal cup surface 155 and the engaging surface 157B (FIG. 8B) and the thickness between the caudal cup surface 155 and the engaging surface 157A (FIG. 8A). As a result, when the caudal cup surface 157B is urged into position against the caudal stem engaging surface 163, the existing stem 160 deflection is taken into account in the shapes of surfaces 157, 163 so that the caudal cup 151 and surface 155 will provide the desired orientation when secured to the caudal stem head 162.

The variability and adaptability of the caudal prosthesis is not limited to only sagittal variation and adaptability. Caudal prosthesis elements 150"" and 150"" are exemplary embodiments illustrating axial variation and adaptability. FIG. 8C illustrates an embodiment of a caudal prosthesis element 150"" having a caudal cup 151C. Caudal cup 151C includes a surface 155 adapted to receive a crossbar end 110, 115 and an embodiment of a surface 157C to engage with the caudal stem head engaging surface 163. In this embodiment of the surface 157C, the surfaces 157C, 163 engage to provide axial caudal cup-stem variation and adaptability (θ axial). This embodiment illustrates an alteration in the surface 157C to provide axial caudal cup-stem variation and adaptability. As a result, when the caudal cup surface 157C is urged into position against the caudal stem engaging surface 163, the existing stem 160 detection is taken into account in the shapes of surfaces 157, 163 so that the caudal cup 151 and surface 155 will provide the desired orientation when secured to the caudal stem head 162.

FIG. 8D illustrates an embodiment of a caudal prosthesis element 150'''' having a caudal cup 151D. Caudal cup 151D includes a surface 155 adapted to receive a crossbar end 110, 115 and an embodiment of a surface 157D to engage with the caudal stem head engaging surface 163. In this embodiment of the surface 157D, the surfaces 157C, 163 engage to provide axial caudal cup-stem variation and adaptability (θ axial) to a lesser degree than that provided by the caudal prosthesis element 150'''' (FIG. 8C). This embodiment illustrates an alteration in the surface 157D to provide axial caudal cup-stem variation and adaptability. As a result, when the caudal cup surface 157D is urged into position against the caudal stem engaging surface 163, the existing stem 160 deflection is taken into account in the shapes of surfaces 157, 163 so that the caudal cup 151 and surface 155 will provide the desired orientation when secured to the caudal stem head 162.

By incorporating variations in the caudal stem attachment point to accommodate sagittal anatomical variation and incorporating variations in the cup attachment point to accommodate axial anatomical variation, the present embodiments can accommodate over 95% of the targeted patient population using a minimal number of parts or "modules." In the instant example, the anatomical variations in a single pedicle of the caudal vertebral body can be accommodated by only six components. As such, it is to be appreciated that the surface 157 may be modified to provide caudal cup-stem variation and adaptability in axial, sagittal and coronal orientations and combinations thereof.

The previous embodiments have illustrated how the surface 157 may be modified to provide the desired caudal cup-stem variability and adaptability. Caudal cup-caudal stem variability and adaptability may also be accomplished utilizing a caudal cup 150 with a fixed or static engaging surface 157. In these embodiments, caudal cup-caudal stem variability and adaptability is accomplished by altering shape and orientation of the caudal stem head 162 and engaging surface 163. The caudal stem head 162 and stem head engaging surface 163 may be modified to provide desired variation and adaptability between the caudal cup and stem in axial, sagittal and coronal orientations and combinations thereof. Caudal stem embodiments 160' and 160" are exemplary embodiments of the possible modifications available to the surface 163 on the caudal stem head 162. Caudal stem 160' illustrates a caudal stem head 162' having an engaging surface 163'. The shape of the engaging surface 163' is such that, when engaged to an embodiment of the caudal cup, the bearing engaging surface is in a desired position. Caudal stem 160" illustrates a caudal stem head 162" having an engaging surface 163". The shape of the engaging surface 163" is such that, when engaged to an embodiment of the caudal cup, the bearing engaging surface is in a desired position.

In yet another embodiment, caudal cup-caudal stem variability and adaptability is accomplished through a combination that utilizes different angled surfaces on both surface 157 and surface 163. As such, one of ordinary skill will appreciate the wide variety of caudal cup-caudal stem variability and adaptability that is provided by altering the engaging surfaces between the caudal cup 157 and caudal stem 163.

If desired, a pad or contact surface piece (not shown) that attaches to the stem head 162 can be used to account for discrepancies (or misalignments) in the orientation of the implanted stem and the desired orientation of the caudal cup. In this way the caudal cup surface and the stem head surface would be "standard" and the contact surface would have one or more inclined faces to mate between and provide the desired stem-cup orientation. This system could incorporate a color code (i.e., blue side to stem and yellow side to caudal cup) to inform the physician of the proper alignment of the pad to the stem and or caudal cup. In a similar manner, alphanumerical designators could be used to denoted the size and orientation of the contact's surfaces (i.e., 3C 5S 10A—indicates a 3 degree coronal tilt, 5 degree sagittal tilt and a 10 degree axial tilt).

In a similar manner to the previously-described caudal stem and cup arrangement, the cephalad elements of the facet replacement prosthesis could incorporate a similar standard stem and multiple attachable cephalad component arrangement, with various size and/or shape cephalad components attached to the cephalad stem to complete the cephalad portion of the facet joint replacement construct. Depending upon the patient's anatomy as well as the desired size, shape and performance/functionality of the construct, the various components could also include components that treat single levels or multiple levels, and could also include components that perform functions in addition to or in place of facet joint replacement. For example, a multi-level facet replacement system could comprise one or more levels that replace removed/damaged/diseased facet joint structures, while one or more other levels of the multi-level replacement system could be designed to accomplish a myriad of tasks, including fusion of other spinal levels or restoration of spinal stability to one or more spinal levels after disc replacement surgery. Similarly, either the cephalad and caudal attachments (or both) could comprise attachments that replace/augment spinal structures both above and below the treated vertebral body, such that a single attachment could extend both above and below the stem to replace/augment both the cephalad and caudal facet joint structures on a single treated vertebral body. Various embodiments could also include attachments (and attachment methods) that facilitate replacement/repair of components during subsequent surgical procedures in the event that additional spinal levels degenerate or require treatment of some sort (or existing levels require intervention of some type or another), to include removal of existing single-level components (but optionally retain the anchoring elements within their anchored position in the vertebral body) to accommodate multiple-level components on the existing anchor structure.

Crossbar Configurability and Adaptability

Because the distance w between the caudal cups can vary depending upon the placement of the caudal stems which in turn varies with the anatomy of the patient, crossbar embodiments of the present invention are adaptable and configurable to accommodate a variety of different widths using, for example, an adjustable crossbar 105 (FIG. 9) or one of several different fixed length crossbars 105A (FIG. 9A). The crossbar is a support member for the bearings (or cephalad facet bearings) and is sized and shaped to span the distance between a portion of the vertebral body where the modular prosthesis is to be implanted. The portion of the vertebral body may include left and right pedicles or lamina. As discussed below, the spanning distance may be fixed (crossbar 105A) or adjustable (crossbar 105). Specifically, the threaded sections 104 and 106 may be adjusted relative to the threaded portion 109 to adjust the crossbar width w (FIG. 9). Bearings may be fixed using conventional means to the ends of an adjustable width crossbar (FIG. 9) or variable depth bearings may be fixed to either an adjustable crossbar (not shown) or to one length of several fixed length crossbars (FIG. 9A). As best seen in FIGS. 9 and 9A, embodiments of a crossbar 105, 105A include a cylindrical bar of approximately 5 mm in diameter (although the diameter could vary from 3 mm to 10 mm, depending upon the desired loads) having a first end 110, 110A and a second end 115, 115A, respectively. Spherical bearings 107, 107A (preferably between 6 and 10 mm, most preferably 8 mm in diameter) are positioned at each end 110, 110A, 115, 115A. Desirably, the bearings 110A, 115A are secured to the bar 105A by a press-fit or tapered fitting or the like (this could also include various other fastening methods, including threads, gluing, welding or the like).

Because the distance w between the caudal cups can vary depending upon the placement of the caudal stems (which varies with the anatomy of the patient), the crossbar 105A will desirably be of varying widths to span this distance. In one embodiment, a series of crossbars having widths from 37 to 67 mm (in increments of 2 or 3 mm) is provided. FIG. 9B illustrates a variety of different length crossbars (106'a-106''''a) corresponding to a variety of different widths (w1-w4). FIG. 9C illustrates a number of alternative embodiments of bearing 107A each with securing holes 9a to 9d of different depth (d1 to d4). As illustrated in the embodiments of FIG. 9C, the securing hole may had a depth, d, that is less than about one-half the diameter of the bearing (i.e., d1, d2), about one-half the diameter of the bearing (i.e., d3) or more than one-half the diameter of the bearing (i.e., d4). In addition, a selection of bearings 107A is similarly provided, the bearings having each having a securing hole extending at least part-way therethrough, sized to accommodate the ends of the crossbar via a press fit. Desirably, the various bearings will have varying depths to the securing holes, with one embodiment of a system having (1) one bearing set with a pair of bearings having a depth of one-half the diameter of the bearing, (2) a second bearing set having the depth of one-half of the bearing plus 0.5 mm deeper and (3) a third bearing set having the depth of one half of the bearing plus 1 mm deeper. By utilizing the various crossbar and bearing combinations (and not necessarily identical depth bearings on each end of the crossbar), the ultimate width of the crossbar construct can be chosen from a minimum of 43 mm long to a maximum of 75 mm long, in one-half millimeter and/or one millimeter increments. Various embodiments of this fixed width crossbar arrangement can be seen in FIGS. 26A, 26B, 30A and 30B, in which crossbar width adaptability is accomplished by providing crossbars having various fixed distances between the ends 110, 115 and variable depth bearings.

Figure 10A:
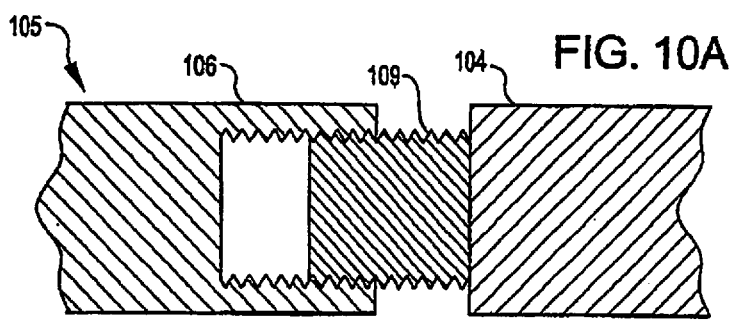

An alternate embodiment of a crossbar 105 constructed in accordance with the teachings of the present invention will now be described with reference to FIGS. 10 and 10A. FIG. 10 is a posterior view of a cross bar 105 in position with a pair of caudal prosthesis 150. The crossbar 105 is a threaded, two piece bar where a first end 110 is attached to a threaded male portion 104 having threads 109. A second end 115 is attached to a threaded female portion 106 having threads sized to receive the threads 109 (FIG. 10A). The threaded ends allow for the interpedicular crossbar width ("w") to be adjusted. The crossbar width is adjusted until the crossbar ends 110, 115 are positioned as desired in contact with the caudal cup surface 155. The interpedicular width, crossbar width "w" or distance between the ends 110, 115 is adjusted by rotating the male portion 104 relative to the female portion 106 to either advance the threads (i.e., increase crossbar width "w") or retreat the threads (i.e., decrease the crossbar width "w"). Cooperative threaded portions (i.e., male and female portions) are provided in each end to allow the width "w" to be altered. Thus, in the illustrated embodiment, the interpedicular distance w is adjustable by rotating the first crossbar end relative to the second bar end.

In the illustrated embodiment, the ends 110, 115 have a generally spherical or rounded external surface 107. The external surface 107 may have any shape that allows for load bearing as well as needed relative movement between the crossbar ends and the caudal cup surface 155. Moreover, the caudal cup surface 155 may also be a factor in determining the crossbar end external shape 107. As will be described in greater detail below, the caudal cup surface 155 is adapted to receive the crossbar ends 110, 115. In addition to the interdependency between the shape of the crossbar ends and the caudal bearing surface, the materials used to coat or form the caudal cup surface 155 and/or the crossbar end external surface 107 may also be selected to improve the durability and operation of the spinal prosthesis. The caudal cup 151 and/or bearing surface 155 and the crossbar ends 110, 105 and/or external surface 107 and/or coatings placed on any of the above may be made of any materials commonly used in the prosthetic arts, including, but not limited to, metals, ceramics, plastics, bio-resorbable polymers, titanium, titanium alloys, tantalum, chrome-cobalt (or cobalt-chrome), surgical steel, bony in-growth surfaces, artificial bone, uncemented surface metals or ceramics, diamond, bulk metallic glasses, or a combination thereof. The caudal cup 151 and/or bearing surface 155 and the crossbar ends 110, 105 and/or external surface 107 and/or coatings placed on any of the above may be the same or different material.

Figure 10B:
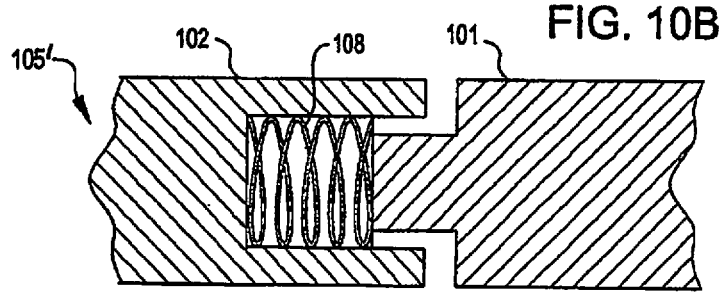

FIG. 10B illustrates another embodiment of a crossbar. The crossbar 105' is a two piece bar having a first end 110 that is attached to an unthreaded male portion 101. A second end 115 is attached an unthreaded female portion 102. The unthreaded female portion 102 is sized to receive the unthreaded male portion 101 and house a bias element 108. The bias element 108 urges the first end and the second end apart and into engaging contact with the caudal cup 151. A retaining ring or other suitable retaining device (not shown) may be included to retain the bias element 108 in place between the male and female ends. In an embodiment of a modular spinal prosthesis utilizing a crossbar 105', a plurality of the crossbars 105' are provided each having a different working width. A working width refers to a range of crossbar width values within which the bias element may outwardly urge the ends 110, 115 into engaging contact with the caudal bearing 151 while still providing sufficient structural strength for the crossbar 105' to operate as a load bearing element within the spinal prosthesis The crossbar ends 105, 110 and the caudal cup 151 and bearing surface 155 may also be any appropriate and cooperative shapes to give appropriate support to the prosthesis bearing components, the spine and to provide the appropriate range of motion for the anatomical location of the prosthesis. FIG. 11A illustrates an exemplary modification to the external surface 107 of the crossbar ends 110, 115. In the illustrated embodiment, a portion of the end of crossbar outer surface 107 has been modified to provide altered surface 107'. Altered surface 107' has been added to the crossbar ends 110, 115 to improved bearing performance of the ends 110, 115 against the caudal bearing surface 155. In the illustrated embodiment, a crossbar end lateral portion 107' has been altered to provide an improved bearing surface with the lateral surface 159. In this embodiment, the lateral surfaces 159 and the shaped crossbar end surface 107' are both flat. Other shapes are possible, such as a shape that conforms to the inner surface of the caudal cup at the ends of each range of motion.

In alternate embodiments, the entirety or a portion of the crossbars may have non-circular cross sections, including polygonal, hexagonal, oval, etc, to reduce and/or prevent rotation of the crossbar during loading conditions, as well as to allow the crossbar to be rotated (if desired) using tools such as wrenches, etc. Accordingly, embodiments of the crossbar may be utilized as a support component sized to span a portion of the vertebral body and adapted to receive a pair of prosthetic facet elements. The pair of prosthetic facet elements are positionable relative to the support component to replace a portion of a natural facet joint. Additionally, there may also be a kit comprising a plurality of support components having different lengths, or alternatively, the crossbar or support element may be further adapted to have an adjustable width. In some embodiments, the crossbar may be secured to a vertebral body or to an adjacent vertebral body. The crossbar or support member in conjunction with other components may be used to provide symmetric and/or asymmetric anatomical solutions. In other embodiments, the support component has an opening adapted to receive the prosthetic facet elements, and/or the prosthetic facet elements are slideable along the width of the support component. The prosthetic facet elements may be fixed in a pre-ordained position medial or lateral of the typical or atypical anatomic location. While the crossbar has been illustrated in embodiments where the prosthetic facet elements are cephalad elements, embodiments of the crossbar or support component may also be used with caudal prosthetic facet elements. Similarly, crossbar elements could be used in conjunction with BOTH cephalad and caudal elements, with varying results.

Additional modifications of the caudal cup are also possible in order to improve the operation and reliability of the prosthesis through the range of spinal motion. One such modification is illustrated in FIG. 11B. Caudal cup 150' is a modified version of the caudal cup 150. The caudal cup 150' includes an upper crossbar end retainer 161 and a lower crossbar end retainer 164. The upper and lower crossbar end retainers 161, 164 may optionally be provided to reduce the likelihood that the crossbar ends 110, 115 will slide out of contact with or leave an acceptable area adjacent the caudal cup surface 155 (dislocate). In a similar manner, the posterior surface of the caudal cup could also be closed (not shown), thereby capturing and holding the crossbar ends 110, 115 and limiting and/or preventing posterior movement of the crossbar relative to the caudal cups. In this alternate embodiment, the caudal cups could also comprise a "clamshell" design with the lower portion (shown in FIG. 11A) and a mating shape (not shown) that clamps, bolts, clips, or bonds to the lower portion.

The caudal cup 151 desirably provides a surface 155 to engage with the bearing surface located at the crossbar ends 110, 115 and will be described with reference to both FIGS. 12A and 12B. The surface 155 is adapted to receive a crossbar end. The surface 155 has a size, shape(s), and contour(s) that may be adapted to allow, for example, for sliding and relative motion between the crossbar ends 110, 115 and the caudal cup 151 during relative motion between the treated spinal levels. As used herein, relative spinal motion includes flexion, extension, lateral bending, axial/torsional rotation and compound motions including combinations of the above listed types of motion.

The surface 155 is best illustrated with reference to FIGS. 12A and 12B. The surface 155 refers to the interior surface of the caudal cup 151 that is adapted to receive and engage the cross bar ends 105, 110. Once an adaptable spinal prosthesis embodiment of the present invention is implanted into a portion of the spine, the forces generated between the cross bar ends 105, 110 and the caudal cup interior surface 155 will change depending upon the relative movement (i.e., flexion, rotation, extension, etc.) between adjacent vertebrae containing the prosthesis. Force and loading profiles created in the prosthesis will also change depending upon the type and magnitude of the movement. In addition, the caudal cup engaging surface 155 should be configured to allow for relative motion between the crossbar ends 105, 110 and the caudal cup engaging surface 155 while also preventing the cross bar ends 110, 105 from disengaging from the caudal cup 151. The illustrated embodiment of the surface 155 includes: an upper edge 152, an upper bottom surface 153, a lower edge 154, a lower bottom surface 156, a medial edge 158, and a lateral edge/surface 159. The size, shape, relationships between and relative positions of the above listed facets of the surface 155 provide wide ranging options for the configurability and adaptability of the surface 155.

Advantageously, embodiments of the present invention provide engaging surfaces 155 that are highly adaptable and may be configured in a number of ways to accommodate a wide range of force and loading profiles. FIGS. 25 and 25A illustrate how the flexion angle (θF) relates to the shape and slope of the upper bottom surface 153. The flexion angle is desirably determined relative to the upper endplate of the caudal vertebral body. A line, labeled CEP on FIG. 25A, desirably runs parallel to the upper endplate of the caudal vertebral body. A line perpendicular to the CEP (extending along the longitudinal axis of the caudal vertebral body—labeled PEP) is then determined, and the flexion angle (θF) is the angle of the upper bottom surface 153 relative to the PEP. A wide variety of flexion angles may be provided by altering the slope of the upper bottom surface 153. Desirably, the flexion angles associated with various embodiments of the present invention would range from 15 degrees to 35 degrees. More desirably, the flexion angles would range from 20 degrees to 30 degrees. In the most desirable embodiment, the flexion angle is a 25 degree ramp.

In various embodiments, the prosthesis will not only desirably replicate the performance of the facet joint (as well some or all of the various spinal structures removed and/or altered while treating the patient's underlying condition), but will also replicate some or all of the various anatomical structures removed and/or altered by the surgeon to allow access to the treatment area. For example, in order to access the posterior spine, the physician may need to cut and distract soft tissues such as muscles, ligaments and tendons away from the targeted treatment area. By incorporating various limiting devices, such as hard "stops" and sloped ramps, into the facet prosthesis, the various embodiments replicate the function of these tissues as well, thereby more accurately mimicking the performance of a healthy spinal unit.

It should be understood that many of the angles discussed herein are described with reference to one or more two-dimensional angle measuring systems, even though the angles themselves are actually positioned in three-dimensional space. Accordingly, the disclosed desired angle measurements, when projected upon a two-dimensional reference frame, may differ to some degree (however slight) from the specific angles and/or angle ranges disclosed herein, depending upon the extent to which the components of that angle relate to the reference frame.

A functional spine unit can be defined as the caudal and cephalad vertebral body and the intervertebral disc and facet tissues (as well as connective tissues) therebetween (effectively the upper and lower vertebral bodies and the joints therebetween). Because the natural motion of each functional spine unit can differ depending on the spinal level as well as variations in the natural spinal anatomy, the desired flexion angles can differ from unit to unit. In one disclosed embodiment for the replacement of facet joints in the L3-L4 and/or L4-L5 levels, a flexion angle of 25° will desirably (1) allow significant freedom-of-motion to the treated unit, thereby closely mimicking the freedom-of-motion allowed by the original anatomy, and (2) provide for significant stabilization of the treated level, especially where the removal of connective tissues and/or related structure(s) has destabilized the treated unit.

FIGS. 12C and 12D depict an alternate embodiment of a caudal cup 151A incorporating a flange 160A which desirably creates a pocket 162A to contain and/or secure the corresponding cephalad bearing element (not shown) when the prosthesis is articulated to one or more extreme limits of its range of motion. In this embodiment, when the cephalad and caudal elements are compressed together (such as during extension of the spine), the cephalad bearing element (not shown) will slide along the caudal bearing element in the cephalad direction, desirably coming to rest in the pocket 162A formed by the interior surface 155A of the caudal cup 151A. When the bearing (not shown) is positioned within the pocket 162A, any increased compressive force acting on the prosthesis will desirably seat the bearing even further into the pocket 162A, reducing and/or eliminating any opportunity for the bearing to slide out of the cup and potentially dislocate. If desired, a similar flange and pocket (not shown) may be formed on the opposing (cephalad) side of the caudal cup 151A, to capture the cephalad bearing and prevent dislocation of the bearing surfaces during flexion of the prosthesis.

In alternate embodiments, additional crossbar motion may be accommodated by altering the caudal cup width (wcup) or adjusting the distance between the medial edge 158 and the lateral edge 159 in some embodiments. If desired, the upper edges of 152 and 154 could curve over at the top to enclose (partially or fully) the upper portion of the cup 151. In other embodiments, the radius of the curve that transitions between the lateral edge 159 and the upper edge 152 and the radius of the curve that transitions between the lateral edge 159 and the lower edge 154 may also be adjusted to accommodate the various shapes of the crossbar end outer surface 107. In additional alternative embodiments, the medial edge 158 and lateral edge 159 are nonparallel. In other embodiments, the medial edge 158 and the lateral edge 159 could have an actuate shape, or the cup 151 could be completely enclosed with a flexible and/or rigid cover or "cap". In other embodiments, the medial edge 158 could have a raised lip or ridge (not shown) which would desirably assist in retaining the cephalad bearing within the caudal cup. Such arrangements could help prevent dislocation of the construct and/or allow for spontaneous and/or controlled relocation of the bearing surface (operatively, minimally invasively or non-invasively, including non-operative manipulation of the patient's spine through chiropractic procedures, etc.).

In one alternate embodiment, once the cephalad and caudal components of the prosthesis have been secured to the targeted vertebral bodies, one or more elastic compression devices or "bands" could be secured about the caudal cups and bearing elements (see FIGS. 12E-G), to the vertebral bodies themselves, between other parts of the cephalad or caudal prosthesis (see FIG. 12H), or any combination thereof. Properly positioned and/or tensioned, these "bands" would tend to keep the bearing surfaces and caudal cups in contact and/or close proximity, even under extreme and/or unusual loading conditions, and thus reduce and/or eliminate the opportunity for the bearing elements to dislocate. Moreover, in the event that dislocation of the implant did occur, the bands could prevent and/or limit motion of the dislocated joint (by holding the bearing surfaces and caudal cups together), and thus reduce or eliminate damage to other tissues (such as the spinal cord, various other nerves and/or circulatory/connective tissues) resulting from the dislocation. In fact, the compression of the bands might make it possible to eventually "reduce" the dislocation and/or repair the dislocated prosthesis through external manipulation and/or minimally-invasive surgery. If desired, one or more "bands" could be secured between the articulating surfaces of the prosthesis, or between the various arms, cups, stems and/or cross-arms of the construct elements, with varying results. In one embodiment, such a band could be looped around the base of the caudal cup, and around the corresponding cross-arm, in a figure-8 shape. Properly positioned and tensioned, this arrangement would allow the cup and cephalad bearing to articulate without allowing the band to slip off (either or both) the cup and cross-arm. Depending upon the length and size of the band, and the tension therein, the band could positioned and tighten to reduce and/or ultimately prevent any significant articulation of one or both sides of the facet joint replacement prosthesis.

Figure 12E:
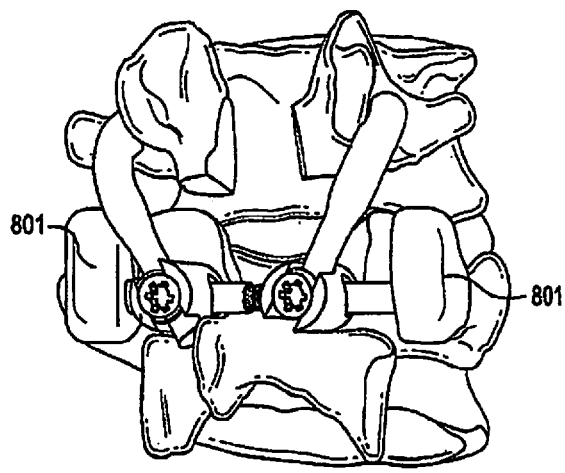
FIGS. 12E-F illustrate an embodiment of a compression device secured about the caudal cups.
Figure 12F:
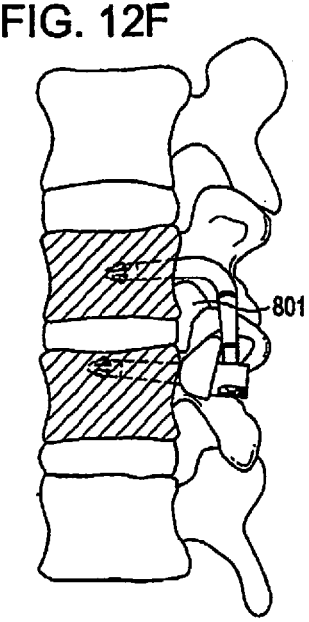
Figure 12G:
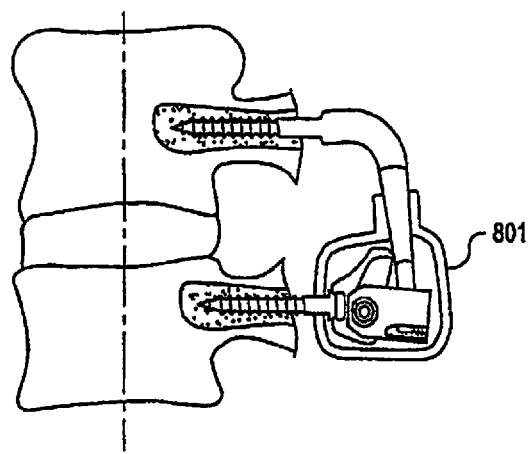
FIG. 12G illustrates an alternative embodiment of a facet replacement prosthesis.
Figure 12H:
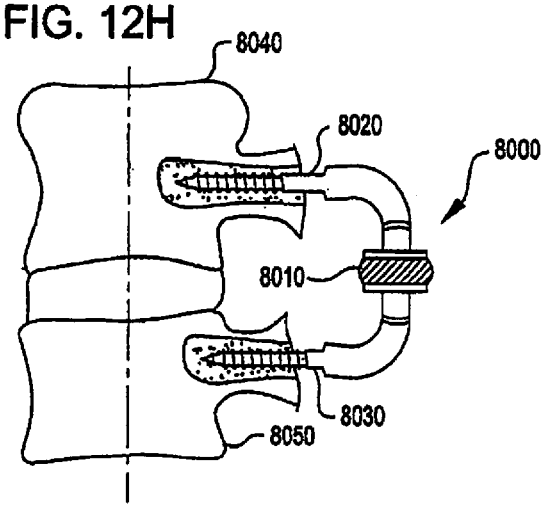
FIG. 12H illustrates another alternative embodiment of a facet replacement prosthesis.

In another alternate embodiment, the compression device could comprise an elastic or pliable material, which may or may not be surrounded by a non-elastic housing, whereby the elastic material allows various movement of the bearing surfaces (with resistance commensurate to the flexibility of the material, as well as flexibility allowed by the coupling to the prosthesis components), but the optional non-elastic housing acts as an ultimate "stop" to movement of the bearing surfaces relative to the caudal cup. Such embodiments could include one or more "encapsulated" bearing surfaces, such as shown in FIGS. 12E and 12F, which show two caudal cup and cephalad bearing pairs (of a facet replacement prosthesis), each pair surrounded by a flexible skin or "jacket" 801 which permits relative movement between the cup and bearing, but which desirably encapsulates or isolates the cup and bearing pair from the surrounding environment (totally or partially or some combination thereof). In practice, the jacket 801 can serve many functions, including (but not limited to) (1) as a shock absorber or brake to limit movement of the bearing/cup complex throughout and/or at the extreme ranges of motion, (2) as a stop or limiter to reduce and/or prevent complete or partial dislocation of the joint, (3) as a barrier to prevent surrounding tissues from invading the bearing surfaces and/or being "pinched" or damaged between moving surfaces, and (4) as a barrier or "filter" to prevent "bearing wear particulate," or other bearing by-products, from reaching and impacting surrounding tissues. In a similar manner, the jacket 801 could encompass the entire bearing construct, with only the cephalad and caudal stems (and possibly the crossbar, depending upon whether the jacket encompasses one or both bearing constructs) protruding through the jacket and extending into the vertebral bodies (see FIG. 12G). Depending upon the type of polymer (or other material) used, as well as the physical properties and orientation of the polymer, the jacket 801 could be designed to control the motion of the prosthesis in a desired manner, and could also control the movement of the prosthesis to more accurately replicate the natural motion of the spinal segment. For instance, a polymer jacket could be designed to allow a greater degree of freedom in flexion/extension, but limit (to some extent) the degree of lateral bending or torsion of the same segment, by proper choice and orientation of the polymer or other material. In one alternative embodiment, the prosthesis could comprise a flexible, polymeric material 8010, such as shown in FIG. 12H.

In various alternative embodiments, the physical properties of the jacket/polymeric material could alter over time or in response to one or more biological, environmental or temperature factors, altering the properties of the material (i.e., polymers, ceramics, metals—Nitinol—etc.). For example, the material could comprise a material that hardens over time (or in the presence of body fluids, proteins, or body heat, etc.), which initially allows the prosthetic components to freely articulate at the time of implantation (and thus minimizing the stresses experienced by the anchoring components), but which hardens and subsequently resists movement to a greater degree once the component anchoring has solidified or bonded to the surrounding bone.

Similarly, the "band" could comprise an elastic, non-elastic or rigid material, such as stainless steel cable, which desirably prevents relative motion of the prosthesis components beyond a certain pre-defined maximum extension/flexion. In various embodiments, the band could alternatively be installed to limit motion of the prosthesis to prevent dislocation, or to minimize or control the articulation of the prosthesis to some degree (such as to protect a disc replacement prosthesis against unwanted motion in one or more directions, protect an adjacent fused level against unwanted stresses, or to protect various tissues from experiences stresses and/or damage). If desired, the cable could be tightened or loosened post-surgery, in a minimally-invasive manner, to alter performance of the prosthesis.

In another alternative embodiment, the prosthesis could incorporate locks or "fusion caps" that desirably convert the prosthesis from an articulating joint replacement construct to a non-articulating spinal fusion construct. In this embodiment, the fusion cap can be installed on or into the caudal cups to desirably immobilize the cephalad bearings within the cups. In various embodiments, the fusion caps could immobilize the cephalad bearings by direct compression or contact, through use of a set screw or other device to secure the cephalad bearing relative to the cup, or the fusion cap could contain or cover an encapsulating material, such as bone cement, which could fill the caudal cup and immobilize the cephalad bearing. Various techniques could be used in conjunction with the installation of such fusion caps, and the cap could be installed prior to, during, or after the completion of a concurrent spinal fusion procedure, including the removal of intervertebral disc material, installation of fusion cages, and/or introduction of material (such as bone graft material) that desirably promotes spinal fusion.

In one disclosed embodiment, the caudal cup has a length of 11.3 mm and a width of 8 mm. Desirably, this arrangement will allow the facet replacement construct to move approximately 15° (between full flexion and full extension of the construct). In one embodiment, the extension will stop at approximately −2° and the flexion will stop at approximately 13° (relative to the longitudinal axis of the spine). If desired, the lateral wall could have a slightly medial inclination to assist in keeping the crossbar ends within the cup during extreme range of motion. Similarly, the implant is desirably able to accommodate at least 7.5° lateral bending to each side.

The caudal cup 151 or the surface 155 may be formed from or coated with a material, e.g. polyethylene, polyurethane, Ultra High Molecular Weight Polyethylene (UHWMP), ceramic, or metal (as well as those materials previously described), which provides glide and cushioning ability for any potential contacting components, such as the crossbar ends or cephalad bearings. In one embodiment (see FIG. 12A), the surface 155 can be formed in a gently upwardly curving shape, similar in shape to a catcher's mitt. Desirably, the caudal cup 151 can be sized to be larger than the crossbar ends 110, 115, allowing for significant articulation and motion of the joint. In addition, the cup 151 and/or surface 155 may comprise modular components of varying sizes, shapes and/or orientations, further increasing the adaptability and/or configurability of the prosthesis.

Figure 13A:
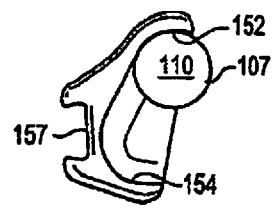
Figure 13B:
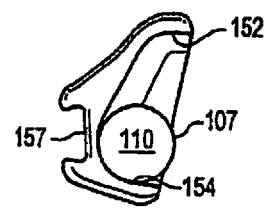

FIGS. 13A and 13B illustrate a crossbar end 110 at the extreme ends of the range of motion for an illustrative embodiment of the caudal cup 151 and surface 155. At full flexion, the crossbar end 110 can be in contact with the upper edge 152 (FIG. 13A). At full extension, the crossbar end 110 can contact the lower edge 154 (FIG. 13B). Depending upon the desired range of motion, the design of the caudal cups and crossbar ends, and the configuration of the implanted components, the crossbar ends will desirably ride against the surface 155 throughout the entirety of the range of motion, and will only sit above and/or not contact the caudal cup surface 155 at the extreme ends of the range of motion.

Cephalad Prosthesis Configurability and Adaptability

An embodiment of a cephalad prosthesis element 120 is illustrated in FIG. 14. The exemplary embodiment of the cephalad prosthesis element includes a bone engaging end 125, a crossbar engaging end 145 and an elbow 147 between the ends 125, 147.

Similar to the caudal stem, the bone engaging end is used as an attachment point to spinal bone and an anchor for the crossbar. The bone engaging end 125 includes a cephalad stem 130 and a distal tip 135. (As previously noted, in various embodiments the distal tip may be configurable or may be formed integrally as part of the cephalad stem.) The length of the bone engaging end 125 in this embodiment is configurable. The length of the bone engaging end 125 determines the overall depth (do) the bone engaging end 125 penetrates the spinal implantation site when the prosthesis 100 is implanted. The overall depth (do) is determined by selecting the desired stem depth (ds) and tip depth (dt). Different stem and tip lengths are provided to ensure that virtually any desired overall depth is available. In various embodiments, the overall depth (do) can range from 35 mm to 55 mm (in 5 millimeter increments). In one embodiment, the diameter of the cephalad stems is approximately 6.5 mm, with a minimum diameter (proximate the flared distal tip) being no less than approximately 5.5 mm.

The distance from the elbow 147 to the distal tip 135 can also be configurable and adaptable depending upon the length of a configurable distal tip selected to attach to a fixed length cephalad stem 130. In one embodiment, the cephalad stem 130 has a fixed length and the distal tip 135 may be selected from a number of distal tips 135 having a variety of lengths. In this embodiment, the bone engaging end 125 length will be the sum of the fixed length cephalad stem 130 and the length of the selected distal tip 135. Alternatively, the length of each of the cephalad stem 130 and the distal tip 135 may be configurable. In this embodiment, the bone engaging end 125 length will be the sum of the length of the selected cephalad stem and the length of the selected distal tip (i.e., 120A, B and C and 170A through 170E of FIG. 18).

In various alternate embodiments, the arm length of the cephalad element 120 can be configurable. Between the crossbar engaging end 140 and the elbow 147 is the arm 145. Embodiments of the cephalad prosthesis 120 may include arms of a variety of different lengths. In another embodiment, the arm length is selected such that the resulting dorsal height of the prosthesis 100, when implanted, is equal to or less than the dorsal height of an adjacent spinous process, or can be equal to or less than the average dorsal heights of the immediate adjacent vertebral levels. In various embodiments, dorsal height can be measured relative to the caudal vertebral body and/or the cephalad vertebral body, or can be measured with regards to an approximate average value there between. In one embodiment, the dorsal height of the construct is not greater than approximately 22 mm from pedicle entry point to the most dorsal point. In an alternate embodiment, the dorsal (posterior) height of the construct is not greater than approximately 25 mm from pedicle entry point to the most dorsal point.

Another aspect of the configurability and adaptability of the cephalad element 120 is the elbow angle ($\theta$elbow). The elbow angle ($\theta$elbow) is the angle formed between the bone engaging end 125 and the crossbar engaging end 140. In the illustrated embodiment, the elbow angle is about 90 degrees. In alternative embodiments, the elbow angle may be greater than or less than 90 degrees, or could possibly range from 60° to 100°, desirably in 5° increments. Moreover, while the arm 145 in the disclosed embodiment is essentially straight, other embodiments could incorporate varying arm orientations, including curved, rounded or compound angles and/or shapes (including C or S-shapes).

The cephalad prosthesis 120 may itself be made of any joint materials commonly used in the prosthetic arts, including, but not limited to, metals, ceramics, titanium, titanium alloys, tantalum, chrome-cobalt/cobalt-chrome, surgical steel, bony in-growth surfaces, artificial bone, uncemented surface metals or ceramics, or a combination thereof. The bone engagement end 125 may be secured directly into a vertebral body, or can be attached and/or "fixed" using a supplemental fixation material such as bone cement, allograft tissue, autograft tissue, adhesives, osteo-conductive materials, osteo-inductive materials and/or bone scaffolding materials. In one embodiment of an adaptable spinal prosthesis of the present invention, at least one bone engagement end 125 is enhanced with a bony in-growth surface. Examples of such surfaces are surfaces created using aggressive bead blasting, sintering processes, porous coatings on substrates, or mechanical/chemical etching (Tecomet Corporation of Woburn, Mass.) which can help fix the fixation element within a vertebra. In other embodiments, the bony in-growth surface can cover a portion or the entire bone engaging end 125. In yet another alternative embodiment, the textured surfaces 132, 137 include a bony in-growth surface. Textured surfaces 132 and 137 may be the same or different. Either or both of the textures surfaces 132, 137 may include features or surface finish to improve or assist in, for example, bony in-growth, or bone cement adhesion. In one disclosed embodiment, the surface finish can extend approximately halfway up the bone engaging end 125 from the distal tip 135.

Alternative embodiments of the present invention could include a prosthesis system having selectable elbows with a stem receiving end and an arm receiving end, arms of different lengths having an end to engage with the elbow arm receiving end and an end to engage with the crossbar; cephalad stems having a variety of lengths and an end adapted to engage the elbow stem receiving end and an end adapted to receive a distal tip; and distal tips having a variety of lengths and cephalad stem engaging ends. In this embodiment, the starting point could be the elbow angle. Unlike the single dimension elbow angle of FIG. 14, this elbow angle would include configurability in any one or a combination of the sagittal, axial or coronal planes. Once the spine had been prepared to receive the prosthesis 100 and the surgeon understood the anatomical orientation requirements of this specific patient, then an elbow having the proper orientation could be selected. The elbow would be selected as a bridge between the anchoring function of the bone engaging end and the crossbar engaging function of the end 140. The elbow angle would also be selected such that, with the proper selection of arm length and stem length, the cephalad prosthesis element would be in the desired alignment for proper alignment and operation of the cephalad elements and crossbar.

Once the desired configuration of the implant is determined, one or more openings or bores (to accommodate the anchoring stems) can be created in the targeted vertebral bodies, and the caudal and cephalad components inserted. If desired, the physician can employ a trialing system or other type of measurement tool (e.g., a device that determines the size and orientation of the various modular components so as to provide proper alignment between the caudal cup and the cephalad attachment point—caudal stem length and cup orientation, an elbow having the desired angular relationship, a cephalad stem of the indicated length and an arm of the indicated length). These pieces can all be fastened together and test fitted in their respective positions on the vertebral body. If a proper fit is achieved, then the pieces are cemented or otherwise permanently joined and the cephalad stem is cemented or otherwise joined to the spinal bone.

FIG. 15 illustrates embodiments of an assembled configurable and adaptable spinal prosthesis 100. These embodiments illustrate how the various components of the prosthesis may be selected and configured to accommodate an individual's anatomy. For example, the illustrated embodiments utilize differing caudal prosthesis. Crossbar end 110 engages with a caudal prosthesis 150' while the crossbar end 115 engages with a caudal prosthesis 150. Both caudal prosthesis 150, 150' have fixed length caudal stems 165. The caudal prosthesis 150' has a caudal fastener length that is the sum of the caudal stem 165 and tip 170. The caudal fastener length of the caudal prosthesis 150 is longer because the distal end 170' has a length longer than the distal tip 170 of the caudal prosthesis 150'. Similarly, the cephalad prosthesis fasteners have different length or depths because the cephalad tip 135' is longer than the cephalad tip 135.

Figure 16E:
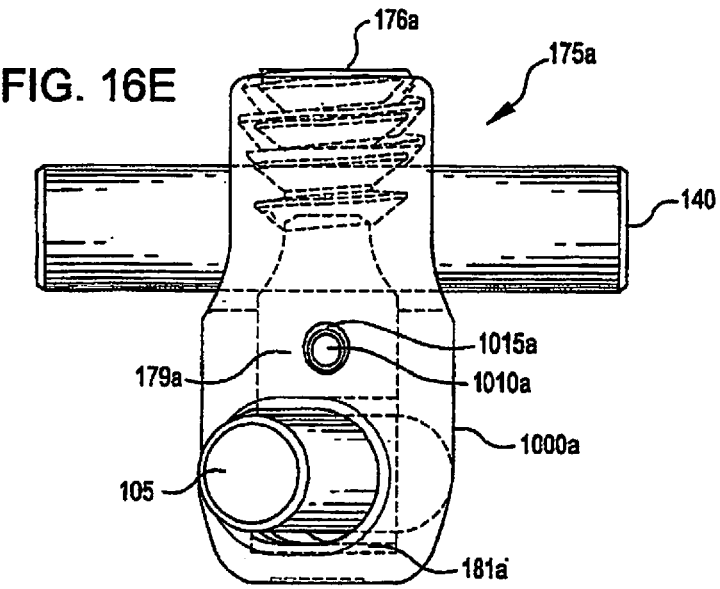
Figure 16F:
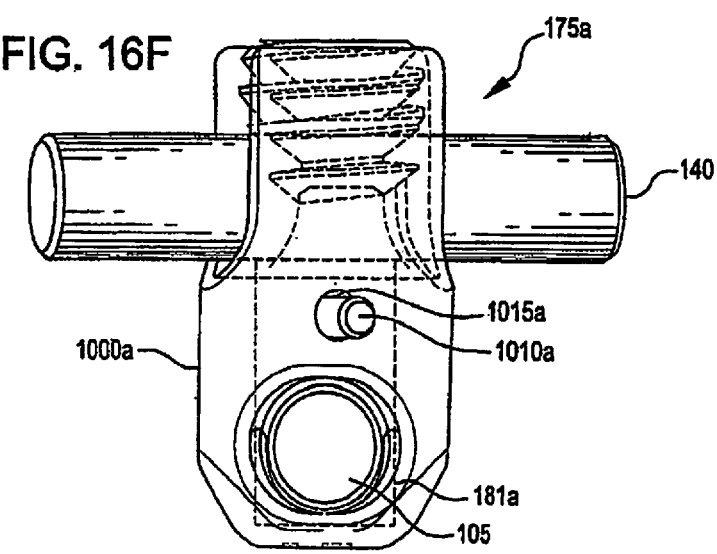

FIG. 15 also illustrates the inner structure of one embodiment of a crossbar mount 175. The crossbar 175, including interior components 172 and 174, will be described with reference to FIGS. 15, 16A and 16B. The crossbar interior components 172, 174 are illustrated in phantom in FIG. 15 and are illustrated in detail in FIGS. 16A and 16B. Arm-crossbar lock engaging element 179 includes a first surface 171 for engaging the cephalad arm end 140 and a second surface 173 for engaging the crossbar 105. The crossbar locking element 181 includes a first surface 177 for engaging the cross bar 105 and a second surface 178 shaped to engage with the interior contours and shape of the crossbar arm mount 175. Each of the locking surfaces 171, 173, 177, 178 may include features, surface treatments or knurling to increase friction contact between the locking surface and the respective component. In one embodiment, the interior components comprise commercially-pure Titanium (CPTi) while the housing and set screw comprise ASTM F136 Titanium Alloy (Ti6Al4V).

The arm-cross bar lock 179 and the cross bar lock 181 each play a roll in providing adaptability to the prosthesis during implantation, fitting and securing the prosthesis in the desired anatomical orientation and position. The fastener 176 is used to lock the cephalad arm and the cross bar into position relative to the crossbar 105. As the fastener 176 compresses the cephalad arm end 140 into the lock element first surface 171, the lock element 179 in turn compresses the second surface 173 onto the crossbar 105. The forces acting on the crossbar 105 urge the cross bar 105 against the crossbar lock first surface 177 and, in turn, the crossbar lock second surface 178 into position against the interior of the crossbar mount 175. As the fastener 176 is tightened, the cephalad arm end 140 is compressively secured in position relative to the crossbar mount 175 between the fastener 176 and the arm-crossbar lock first surface 171. With the same securing action of the fastener 176, the lateral position of the crossbar mount 175 in relation to the cross bar 105 or to the crossbar ends 110, 115 is also secured. As the fastener compresses the cephalad aim end 140, the cephalad arm end 140 applies force to the arm-crossbar lock element first surface 171 that in turn urges the arm-cross bar lock second surface 173 against the crossbar 105. The force applied to the crossbar 105 urges the crossbar 105 against the crossbar lock first surface 177 and the crossbar lock second surface 178 against the interior of the crossbar and arm mount 175. Thus, using a single compressive force, the cephalad arm is secured relative to the crossbar lock 175 and the crossbar lock is secured relative to the crossbar 105 or crossbar ends 110, 115.

One advantage of the current embodiment is that the fastener 176 may place a compressive force against the cephalad arm end 140 and the other components large enough to hold the components in position. This hold force would be less than the force used to secure the components into the final position for implantation. By utilizing a hold force less than a securing force, the prosthesis fit may be adjusted with regards to orientation and relationship between the components. Thereafter, the fastener 176 may be torqued to place a fall compressive load onto the prosthesis to lock it into place. Once the fall torque force is applied, the relatively softer CPTi (as compared to the harder ASTM F136 Ti of the housing, cross-bar and cephalad stems) of the arm-cross bar lock 179 and the cross bar lock 181 will desirably deform to some extent and essentially lock and/or "cold weld" to the ASTM F136 Titanium, locking the implant in its desired configuration. (In the case of subsequent readjustment of a "cold-welded" housing and cross-bar, the cold-weld can be "broken" safely by application of sufficient force in a known manner, and then subsequent re-tightening of the housing when in its new desired position.)

Percutaneous Adjustment of Prosthesis

The various embodiments of facet replacement prosthesis described herein lend themselves to varying degrees of percutaneous, minimally invasive adjustment of the prosthetic components after completion of the surgical procedure. For example, the housings of the prosthesis depicted in FIGS. 29 and 30 can be accessed subsequent to the initial surgical implantation and tightened/loosened via a percutaneous access. Similarly, the connection of various other embodiments depicted herein can be loosened and/or tightened to accommodate damage/loosening of the prosthesis and/or its components as well as to accommodate desired changes in the shape/position of the prosthesis components.

Figure 27A:
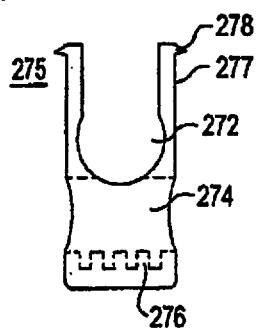
FIGS. 27A-27B illustrate two side views of the crossbar mount of FIGS. 26A and 26B.
Figure 27B:
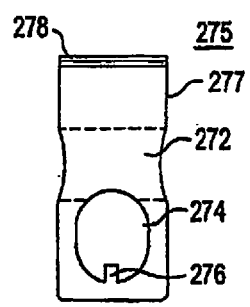
Figure 27C:
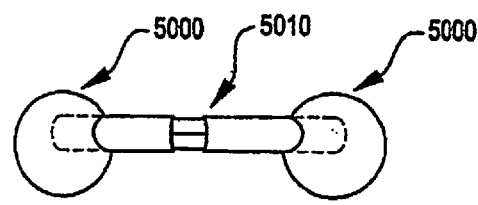
FIGS. 27C, 27D and 27E depict one alternative embodiment of a cross arm and associated cephalad bearings.
Figure 27D:
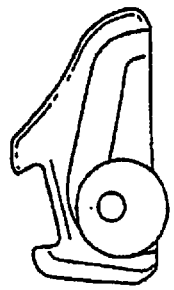
Figure 27E:
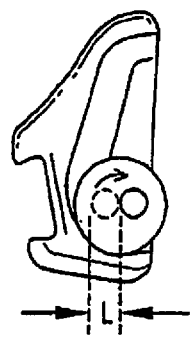

Moreover, in the case of the embodiment of FIGS. 27C, 27D and 27E, the prosthesis can be accessed percutaneously and altered to increase and/or decrease the amount of pre-loading of the cephalad bearings relative to the caudal bearings. Such alteration may be desirous because of anatomical changes in the spinal motion segment (i.e.: the height of the intervertebral disc reduces due to damage or age degeneration, etc.), physical changes in the prosthesis (wearing of the bearing surfaces and/or movement/degradation of the implant), or resulting from a desire to alter the performance of a portion or all of the prosthesis for some reason (i.e., desire to reduce mobility and/or cause hyper mobility of the treated spinal motion segment and/or treat scoliosis, etc). For example, where the cephalad bearings have significantly worn, the prosthesis may be accessed percutaneously, the housings loosened, and the crossbar and attached bearings rotated to present an unworn face of the cephalad bearings to the caudal cups. The housing can then be retightened, and the tools and access instruments removed. By allowing repair and/or adjustment of the spinal prosthesis to be accomplished in a percutaneous manner, this embodiment alleviates the need for a significantly invasive second surgery to repair and/or re-adjust the implant/bearing surfaces due to prosthesis wear.

In a similar manner, various embodiments of the facet joint replacement prosthesis could incorporate varying adjustable features, with the features desirably adjustable through a range of positions using only post-surgery, minimally invasive percutaneous access to the prosthesis. Desirably, percutaneous adjustment of the facet prosthesis can be used to accomplish numerous alterations to the position, loading and/or orientation of the facet joint replacement prosthesis, including alteration of the position and/or orientation of the cephalad arm(s) relative to the cephalad anchor(s), extension/contraction of the cephalad arm(s), alteration of the housing angle (between one or more cephalad arms and the cross-arm) and housing position(s) relative to the cephalad arms and/or cross-arm, rotation and/or displacement of the cephalad bearing surface(s) relative to the caudal cup(s), and rotation and/or displacement of the caudal cup(s) relative to the cephalad bearing(s) and/or the cephalad anchor(s).

FIGS. 16C through 16F depict various views of one alternative embodiment of a crossbar mount 175A constructed in accordance with the teachings of the present invention. These figures depict the fastener 176A, the cephalad arm lock 179A and the crossbar lock 181A, with the housing 1000A illustrated in phantom. As with the previously described embodiment, tightening of the fastener 176A into the housing 1000A desirably "locks" the prosthetic components in place within the housing 1000A.

In the embodiment of FIG. 16C, a retaining pin 1010A extends through an opening 1015A formed through the cephalad arm lock 179A and press fits into openings 1020A in the housing 1000A. Desirably, the opening 1015A is larger than the outer diameter of the pin 1010A, allowing the cephalad arm lock 179A to "float" within the housing 1000A relative to the pin, but be retained within the housing 1000A. Moreover, the presence of the cephalad arm lock 179A will desirably retain the cross-bar arm lock 179A within the housing 1000A in its desired position as well.

Figure 17:
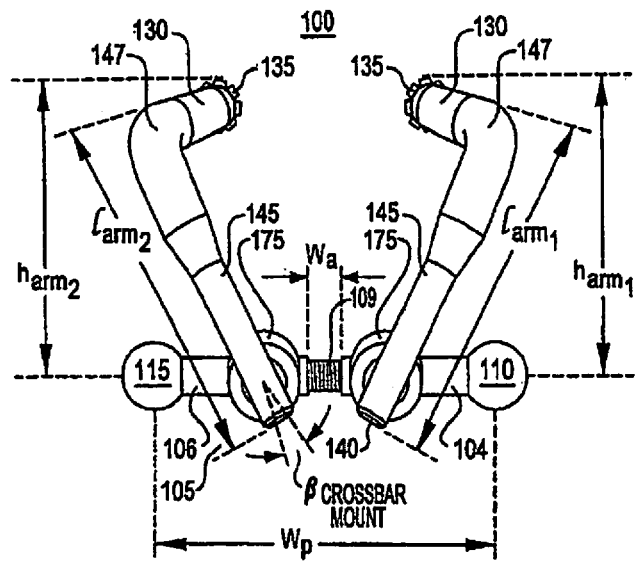
FIG. 17 is a posterior view of the cephalad portion of an embodiment of a modular prosthesis.

The interplay between the various components of the cephalad prosthesis may be appreciated through reference to FIG. 17. FIG. 17 illustrates a posterior view of an embodiment of the cephalad portion of an anatomically adaptable spinal prosthesis of the present invention. Several adaptable features are presented. The cephalad arm height (harm1 and harm2) may be adjusted, for example, by moving the cephalad cross bar engaging end 140 relative to the crossbar mount 175, or rotating the crossbar mount 175 about the crossbar 105. While illustrated as the having the same height, each of the cephalad arms may be individually sized and selected as well as adjusted relative to the crossbar mount 175 to provide different arm heights. As such, it is possible in some embodiments that harm1 will be a different value than harm2. It is to be appreciated that in various embodiments, the size of an individual cephalad arm could be adaptable depending upon, for example, selecting an arm length, a stem length and a distal end length. Stem length and distal tip length are described earlier. Desirably, more than one housing, each housing having a differing angle β (cephalad arm 145 relative to the crossbar mount) is provided. In one embodiment, β crossbar mount is either 15° from normal or 35° from normal (the individual housings could be symmetrical—i.e., both 15° or both 35°, or could be non-symmetrical—i.e. one 15° and one 35° housing on the same cross-bar, depending upon anatomical considerations). Moreover, because the housing through-hole for the crossbar mount is larger than the diameter of the cross-bar, the housing can be rotated approximately 20° with the cross-bar in position, thereby allowing for further variance and/or further misalignment of the cephalad arm relative to the cross-bar. Thus, in this embodiment, the two housings could accommodate angle β crossbar mount from 5° to 45°. The prosthesis width (wp) is also variable by increasing or decreasing the adjustable width (wa) of the threaded portion 109 between the threaded crossbar ends 106, 104 (in this embodiment) or by simply choosing a different width crossbar during initial implantation (in various alternate embodiments).

In summary, the illustrated embodiment of a cephalad prosthesis 100 of the invention is adaptable in at least four ways. First, the cephalad arm 145 and crossbar end 140 may move relative to the crossbar mount 175 to vary cephalad arm height (harm1 and harm2). Second, the cephalad arm 145 and crossbar end 140 may also rotate relative to the crossbar mount 175 thereby moving the position of the distal tip 135 along an actuate pathway. Third, the crossbar mount, with or without the cephalad arm secured thereto, may move along the crossbar 105 towards or away from, for example, the other crossbar mount 175, and/or the ends 110, 115. Fourth, the crossbar width may be increased or decreased by rotating the threaded crossbar ends 104, 106.

The modular design aspects of embodiments of the present invention are illustrated in FIG. 18. FIG. 18 illustrates an embodiment of a kit 290 having embodiments of the modular, configurable and adaptable components of the present invention. The kit 290 provides an organization for the various configurable and adaptable components of the spinal prosthesis embodiments of the invention. More importantly, the kit 290 provides a way to organize the various components and simplify the process of selecting, configuring and adapting a spinal prosthesis of the present invention. Adaptable spinal prosthesis kit 290 includes a plurality of components that may be utilized to produce an embodiment of an adaptable spinal prosthesis according to the present invention. These components are related to the spinal prosthesis 100 but are also generally applicable to the adaptable component embodiments of other spinal prosthesis embodiments.

Adaptable cephalad prosthesis embodiments 120A, 120B and 120C differ in cephalad stem 130 length. The length of each stem 130 may be any length and the difference between the three sizes may be small or large. In one embodiment, the small stem 120C has a cephalad stem length of approximately 35 mm (which can include a selection of bone-penetration lengths of approximately 55 mm, 50 mm, 45 mm, 40 mm and/or 35 mm), the medium stem 120B has a cephalad stem length of approximately 45 mm and the large stem 120A has a cephalad stem length of approximately 55 mm. While the illustrated embodiments have a common elbow angle of approximately 85°, it should be understood that alternative embodiments may include elbow angle as a configurable option—an exemplary selection for such a kit could include stems having elbow angles ranging from 60° to 100°, with the most desirable angle being approximately 85°.

Three exemplary crossbar sizes are also provided having increasing width from 105A, 105B and 105C. The crossbar 105A may have, in an exemplary embodiment, widths of approximately 37 mm, 51 mm and 67 mm, with preferred adjustment widths of 0 to 15 mm. During the implantation process, the patient anatomy and the placement of the caudal cups comprise two of the inputs used to determine the crossbar size. In most instances, the crossbar selected is narrower than the caudal cup spacing but within the adjustable range for the threaded ends. Once the caudal cup is positioned, the crossbar may be placed in the cups and then fine tuned for width using the threaded ends. In an alternative embodiment, individual cross-bars of set sizes (i.e., a set of crossbars of the following widths: 37 mm, 39 mm, 41 mm, 43 mm, 45 mm, 47 mm, 49 mm, 51 mm, 53 mm, 55 mm, 57 mm, 59 mm, 61 mm, 63 mm, 65 mm and 67 mm), with adjustable depth bearings, can be provided.

While the illustrated embodiment illustrates the distal tips 170 and 135 having the same length selections, alternative embodiments provide distal tips 170 selectable from a variety of lengths that are different from the selectable lengths for distal tip 135.

Caudal stem 160 adaptability is also illustrated by various angled stems. In this embodiment, angle Θc changes for each of the caudal stem head 162 and the stem 160. Θc in stem 160A is ranges from approximately 5° up to approximately 35°, in 5° increments. While the illustrated embodiment only illustrates one form of caudal stem adaptability, it is to be appreciated that each of the adaptable characteristics of the caudal stem (i.e., the stem angle Θc, the shape of the caudal stem head 162 and the shape of the caudal cup engaging surface 157) may each be used alone or in any combination to provide caudal stem variability into any orientation sagittally, axially, coronally or combinations thereof. While the stem 160 embodiments have been illustrated having the same length, it is to be appreciated that the stem 160 may also have various lengths or range of lengths as described above with regard to cephalad stem 130.

Figure 19:
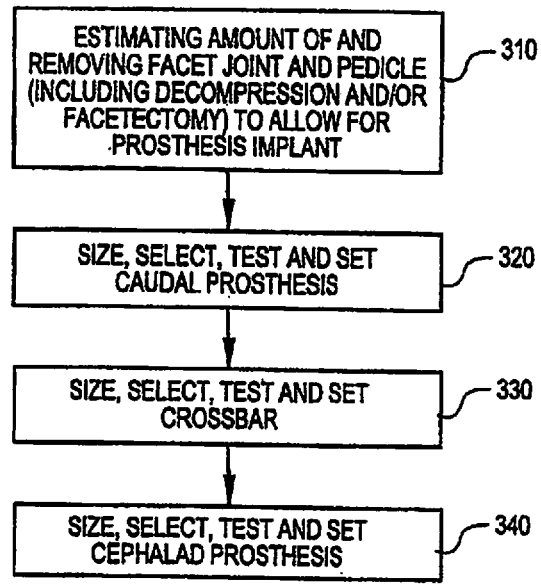
FIG. 19 is a flow chart of an embodiment of a surgical method.

FIG. 19 is a flow chart illustrating an embodiment of a surgical method 300 for implanting an embodiment of an adaptable spinal prosthesis according to the present invention. The surgical procedure comprises exposing the spinous process, lamina, and facet joints at a desired level of the spine using any method common to those of skill in the medical arts. Once the physician is prepared to implant the prosthesis, he/she will first estimate the amount of and remove any portions of the vertebral body (such as facet joints, lamina, processes, etc.) to allow for prosthesis implantation (310). The prominent bone may be removed and/or rongeured using any means common in the field. The superior facet and/or lamina may also be trimmed to decompress the nerve root. A reamer or any other instrument that is useful for grinding or scraping bone may be used to ream, shape or contour the spinal bones as depicted in FIG. 20 in preparation for implanting the prosthesis.

Prosthesis Implantation Methods and Tools

Figure 20:
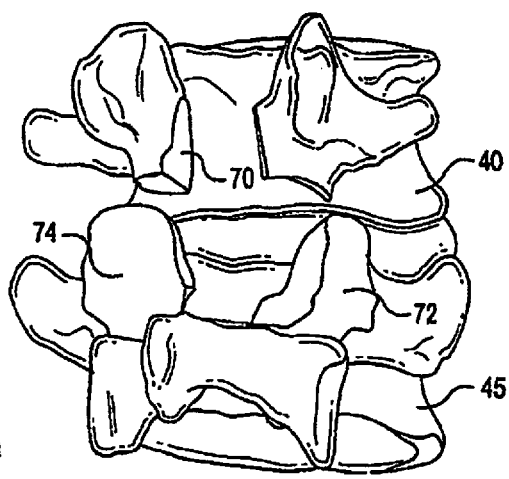

FIG. 20 illustrates a posterior view of vertebral bodies 40, 45 after performing a procedural bone resection, a wide decompressive laminectomy, facetectomy and/or laminectomy to the degree determined in step 310 and discussed above. Some and/or all of the spinous process and inferior facet joints have been removed from vertebra 40 to remove diseased bone, relieve pressure on nerves or other tissues, and/or create sufficient space for placement of an embodiment of an adaptable spinal prosthesis of the present invention. The superior facet joints have been removed from vertebra 45 and the lamina shaped to produce caudal prosthesis receiving surfaces 74, 72. Pilot holes are initially formed in the vertebra 40, 45 to prepare for cephalad and caudal stem implantation and/or carry a trialing system (desirably for trialing and/or sizing prosthesis prior to implantation). Desirably, this initial diameter and/or depth of the pilot holes in each of the pedicles will be sufficiently small to allow for the implantation of a commercially available spinal fusion system (such as the TSRH rod and screw system commercially available from Medtronic/Sofamor Danek) in the event that the spinal anatomy and/or bone condition is such as to preclude implantation and/or proper functioning of the facet replacement system of the present invention. In the disclosed embodiment, the pilot holes are drilled to approximately a 4 mm diameter.

In order to determine if the components of the spinal prosthesis can accommodate the specific anatomy of the patient undergoing treatment, the system can include a "component variance" device or "go-no go" (GNG) gauge. In one embodiment, the GNG gauge comprises a series of adjustably-linked components, each component adjustable within a given range of variability equal to the range spanned by each group of components in the modular component set. Desirably, if the posts of the GNG gauge can each be inserted into a corresponding cephalad and caudal pilot hole, this fitting indicates that the individual components can acceptably span that anatomy, and thus a properly-fitting facet joint replacement prosthesis can be constructed and implanted into the targeted vertebral bodies.

Figure 20A:
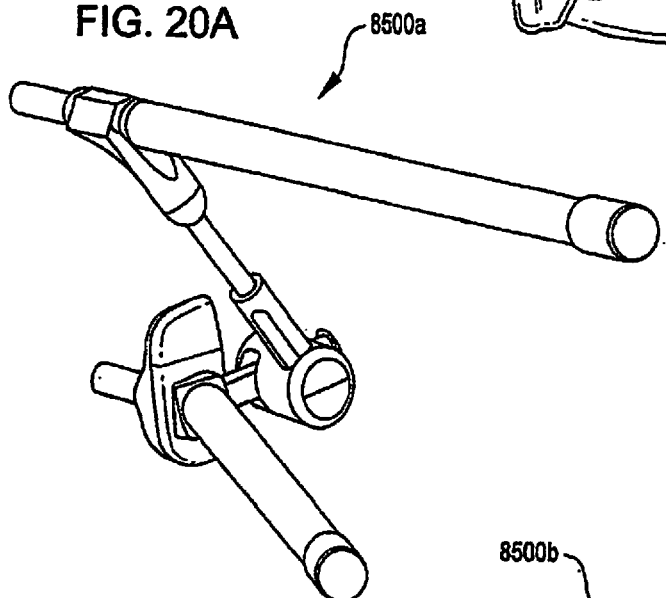
Figure 20B:
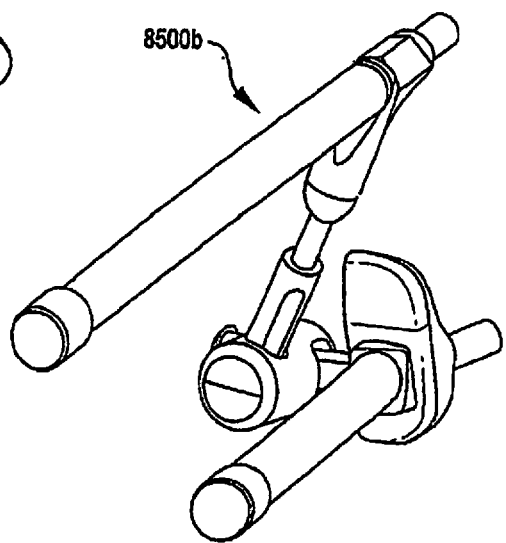

In the disclosed embodiment, the GNG gauges duplicate the variability of: (1) the cephalad arm length, (2) the housing angle, (3) the cross-arm width and clearance (4) the cross-arm rotation, and (5) the caudal cup clearance and orientation. The embodiment shown in FIG. 20A depicts a left-side GNG gauge 8500a, and the embodiment shown in FIG. 20B depicts a right-side GNG gauge 8500b. If desired, both individual gauges could be combined into a single GNG gauge 8500c to replicate the range of variability of the entire construct, as shown in FIG. 20C. Moreover, if desired the GNG gauge could accommodate visual markings to indicate the size and shape of the component(s) necessary to construct a prosthesis capable of spanning the targeted anatomy. Once the GNG gauge has satisfactorily indicated that a prosthesis can be constructed that fits the targeted anatomy, the GNG gauge is removed and the caudal stem holes 52 and 54 are formed in vertebra 45 and cephalad stem holes 56, 58 are formed in vertebra 40 (see FIG. 21), which in the disclosed embodiment are approximately 6 mm diameter holes. The depth, size, and orientation of these holes are used to determine selections in the prosthesis kit 290 and embodiments thereof.

If desired, a drill 6000 and/or rongeur 6010 incorporating an adjustable depth stop, such as depicted in FIGS. 20D and 20E, could be used to drill/enlarge the hole of desired depth/dimensions.

Figure 22:
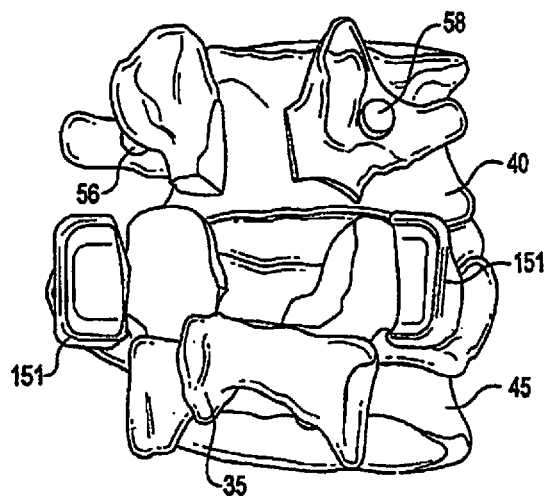

Returning to the surgical method 300, size, select, test and set the caudal prosthesis (step 320). As described above, the adaptability of the orientation and position of the caudal prosthesis may be utilized to meet a wide variety of anatomical situations and to accommodate a variety of different adaptable prosthesis. It is to be appreciated that each of the adaptable characteristics of the caudal prosthesis including, for example, the stem angle Θc, the shape of the caudal stem head 162 and the shape of the caudal cup engaging surface 157 and the lengths of the caudal stem and distal end may each be used alone or in any combination to provide caudal stem variability into any orientation sagittally, axially, coronally or combinations thereof. The caudal prosthesis may be configured by selecting the desired caudal stem (see stems 160A-160E in FIG. 18), distal tip (see distal tips 170A-170E) and caudal cup 151 (see FIG. 18). FIG. 22 illustrates the selected components after implantation. The caudal cups 151 are secured to caudal stems (not shown) that have been implanted into the caudal stem holes 52, 54 formed in the vertebral body 45.

Figure 22A:
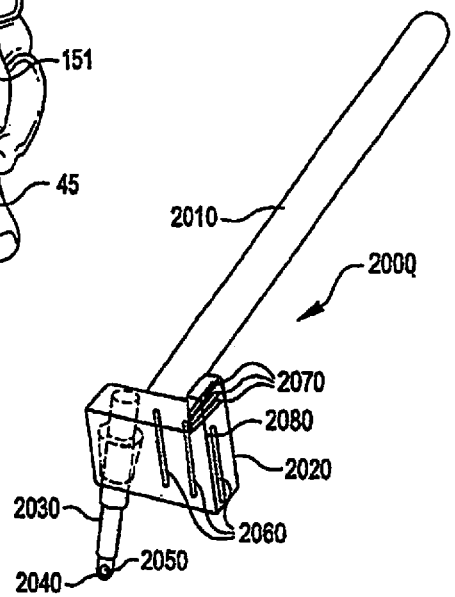
FIGS. 22A and 22B depict embodiments of component selection instruments.
Figure 22B:
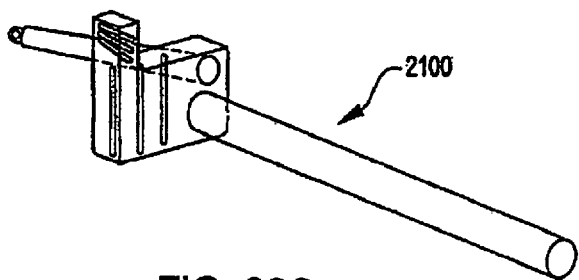

Aside from trialing a plurality of caudal prosthesis to determine the necessary caudal components, one alternate device and method for determining the proper size and orientation of the caudal cups 151 is disclosed in FIGS. 22A and 22B, which depict a component selection instruments 2000 and 2100 for determining the proper combination of caudal anchor stem and caudal cup best suited for the targeted anatomy. In this embodiment, one component selection instrument 2000 comprises a handle 2010, a body 2020 and a stem 2030, each of these preferably comprising a radiolucent material. Within the body 2020 and the distal tip 2040 of them stem, radiopaque markers 2050, 2060 and 2070 are positioned, such that, when the stem 2040 is inserted into the pilot hole (not shown) of a targeted vertebral body, upon radiographic visualization of the body, the radiopaque markers align to indicate the proper combination off components for the targeted region.

Specifically, the depicted embodiment of a component selection instrument (CSI) 2000 incorporates a distal radiopaque marker 2050 positioned within the distal tip 2040 of the stem 2030. A series of stem selection radiopaque markers 2060 (in this embodiment, three markers) is positioned within the housing. A series of cup selection radiopaque markers 2070 (in this embodiment, three markers) are also positioned within the housing. If desired, the CSI can be optimized for single-sided use (for measurement of only the left or right pedicle) or for dual-sided use (for example, the CSI could incorporate symmetrical radiopaque markers that provide the proper measurements depending upon the orientation of the instrument—see FIGS. 22A and 22B).

Once the stem 2030 is inserted into the pilot hole (not shown), the interior edge 2080 of the housing 2020 (the edge nearest the centerline of the spine) is visually aligned with the spinous process, and an anterior/posterior (A/P) view is taken of the spine and CSI using a fluoroscope. Depending upon the lateral angle of the pedicle, the distal radiopaque marker 2050 will line up with (or will be closest to) one of the stem selection radiopaque markers 2060, each of which correspond to a different stem angle. After taking the A/P view, the physician can then take a lateral view of the spine and CSI. From the lateral view, the physician will align the cephalad endplate of the caudal vertebral body (not shown)

with the most appropriate cup selection radiopaque marker, which gives the proper cup size for implantation. If desired, the CSI 2000 and 2100 can incorporate shortened or removable handles 2010, to accommodate small incisions (or can even have no handle 2010, allowing placement of the device with a removable clamp or similar instrument.).

The caudal stem may be secured directly into the vertebral body, or can be attached and/or "fixed" using a supplemental fixation material such as bone cement, allograft tissue, autograft tissue, adhesives, osteo-conductive materials, osteo-inductive materials and/or bone scaffolding materials. In one embodiment, the first fixation element can be enhanced with a bony in-growth surface, such as surfaces created using sintering processes or chemical etching (Tecomet Corporation of Woburn, Mass.) which can help fix the fixation element within a vertebra. As described above, the bony in-growth surface can cover all or a portion of the caudal fixation element. Desirably, the final orientation of the caudal cups 155, 157 will be parallel (relative to the lateral walls 159) and coplanar (with respect to the upper bottom surfaces 153).

A caudal cup holder (not shown) can be used to ensure the caudal cups are properly aligned and positioned during the implantation and cement curing process. Desirably, the caudal cups will be aligned such that the inner edges and inner faces of each caudal cup are parallel to the other.

Figure 22C:
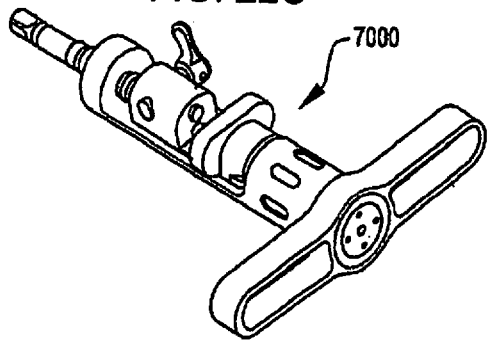

In the disclosed embodiment, each of the caudal cups is secured to its respective caudal stem using a tapered press-fit. To ensure proper and secure attachment, a compression device 7000 (see FIG. 22C) is provided that accurately and repeatably compresses and secures the cup onto the stem.

Figure 23C:
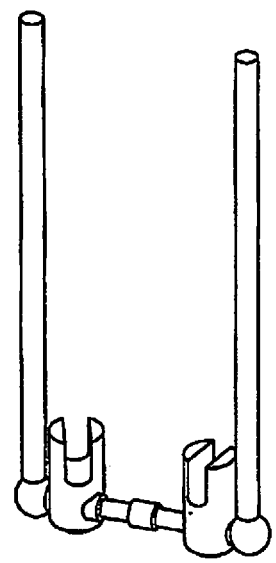
FIGS. 23C and 23D depict embodiments of housing trials.
Figure 23D:
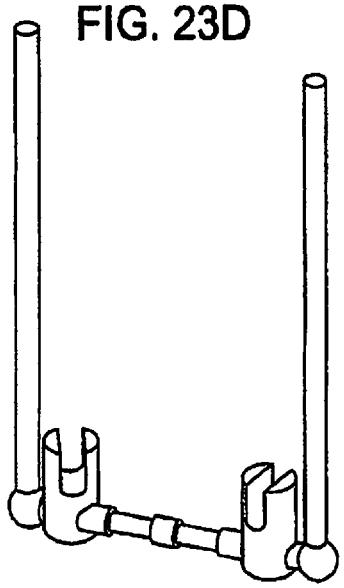
Figure 23E:
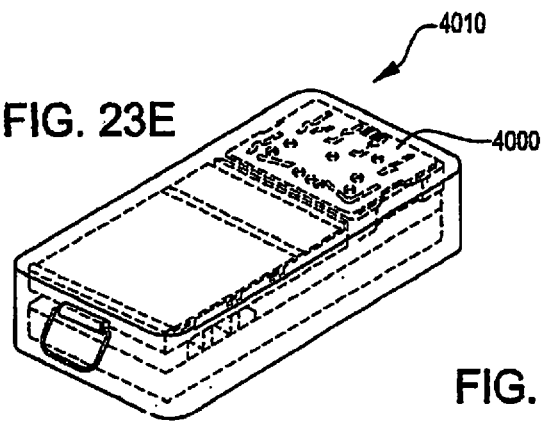
FIG. 23E depicts one embodiment of an implant case incorporating an integral component holder tray.

Once the cement secures the caudal cups in position, the physician can size, select, test and adjust the crossbar (step 330). FIG. 23 illustrates an embodiment of a crossbar 105 in position between the caudal cups 151. The crossbar 105 has been selected from, in this exemplary embodiment, crossbars 105A, B and C in the kit 290 (FIG. 18). The particular selection of crossbar 105A, B or C is based, in part, on the distance between the caudal cups 151. As discussed above, the width of the crossbar 105 may be selected initially to place the crossbar ends 115, 110 against the caudal cup receiving surface 155. The crossbar width is adjusted into final position using the adjustable crossbar members 104, 106 and threaded portion 109. Additionally, the crossbar mounts 175 are present with the crossbar 105 disposed within the crossbar engaging portion 174. A crossbar measuring tool 3000, such as shown in FIG. 23A, can be used to determine the distance between the caudal cups and recommended crossbar length/bearing sizes. Once the proper crossbar components are selected, a crossbar compression device 9000 (see FIG. 23B) can be used to securely press-fit the cephalad bearings onto the crossbar.

Figure 24:
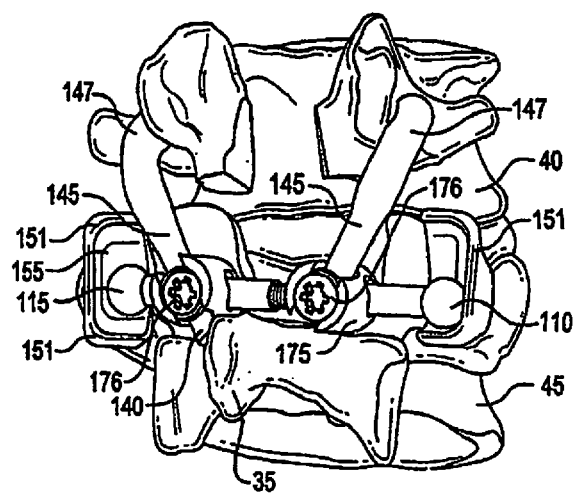

Size, select, test and set the cephalad prosthesis (340). If desired, a tool similar to the CSI cam be used to size the cephalad elements of the prosthesis, or trialing of different cephalad components can be used. Referring initially to FIG. 23, the cephalad prosthesis is adapted to have the crossbar engaging end 140 engage with the crossbar cephalad engaging portion 172 and the bone engaging end 125 (not shown) engaged within the lamina or spinal bone via holes 56,58. Within these parameters the cephalad arms are configured and adapted by selecting the desired cephalad stem 130 length (see cephalad arms 120A-120C in FIG. 18). In alternative embodiments, distal tip 135 length (see distal tips 135A-135E in FIG. 18), elbow angle and arm length may also be configurable and selectable characteristics. As illustrated in FIG. 24, the cephalad arm crossbar engaging ends 140 are secured by fixation element 176 to the cross bar mount cephalad engaging portion 172. In addition, the cephalad arm 145 has also secured the crossbar relative to crossbar mount utilizing the locks 179 and 181 (not shown).

Various additional surgical tools, including housing trials (see FIGS. 23C and 23D), can be used to determine proper component sizes and shapes. Of course, it should be understood that different size and shape components can be used together (such as two different sizes of housings and/or cephalad arms) to accomplish the objective of accommodating the widest range of anatomy. Once the proper components have been selected (or whenever each proper component has been determined through measuring and/or trialing) the surgical kit includes a component staging area 4000, formed on the tray cover 4010, which can hold the various components of the unassembled and/or partially assembled prosthesis in a secure and sterile location (see FIG. 23E).

FIG. 24 also illustrates one of several advantages of the modular design of the present invention. One advantage is the independence of cephalad arm and crossbar mount adaptability. Note that the cephalad arm end 140 in the crossbar mount adjacent the end 115 extends significantly beyond the crossbar mount 175 while the cephalad arm end 140 in the crossbar mount adjacent the end 110 does not extend significantly beyond crossbar mount 175. Another advantage is the independence of the cephalad components. Each cephalad arm 145 may be separately adjusted to best accommodate the anatomical situation of the patient as well as the crossbar position and loading parameters. As illustrated, the cephalad arm adjacent end 115 is arranged differently within the prosthesis 100 than the cephalad arm adjacent 110.

If desired, a series of clamps or rigs (not shown) can be used to hold either or both of the cephalad or caudal prosthesis (or their trialing analogs) in place during the sizing and/or testing phases and/or while the cement or other fixation material cures.

FIGS. 23 and 24 also depict another advantage of one embodiment of the modular design of the present invention. Because the spinous process 35 is located directly caudal to the crossbar 105 and the caudal cups 151, the spinous process 35 can act as a "stop" or barrier to the crossbar 105 beyond a certain pre-determined point, reducing and/or preventing any opportunity for the cephalad bearings 110 and 115 to dislocate caudally out of the caudal cups 151, even if various forces push the cephalad bearings posterior of the caudal cups. By choosing the proper amount of spinous process 35 to resect (if necessary and/or desired), the physician can position the remaining spinous process 35 of the caudal vertebrae 45 to allow full freedom of motion to the crossbar 105 relative to the caudal cups 151, but prevent undesired caudal movement and/or dislocation of the crossbar 105. In addition, proper positioning of the cross-bar can potentially result in the cross-bar contacting the spinous process prior to contacting the bottom of the caudal cups. Such an arrangement could result in a pain response (resulting from contact between the cross-bar and the spinous process) alerting the patient to the imminent "bottoming-out" of the cephalad bearings in the caudal cups (and thus inducing the patient to discontinue further motion in that direction).

FIG. 25 is a section view of a portion of the spine having 4 vertebral bodies. Vertebral bodies 30 are unmodified while vertebral bodies 40, 45 have been altered by the surgical techniques described with regard to surgical method 300 to implant an embodiment of the adaptable spinal prosthesis 100.

FIGS. 25, 25A and 25B depict the desired placement for one embodiment of a caudal cup constructed in accordance with the teachings of the present invention. In this embodiment, the upper endplate 45A of the caudal vertebral body is utilized as a guide for proper placement of the caudal cup. As previously noted, a line, labeled CEP on FIG. 25A, desirably runs parallel to the upper endplate 45A of the caudal vertebral body (which can be visualized fluoroscopically, or via minimally-invasive or open visualization). A line perpendicular to the CEP (extending along the longitudinal axis of the caudal vertebral body—labeled PEP) is then determined, and the flexion angle (θF) is the angle of the upper bottom surface 153 of the caudal cup relative to the PEP. Desirably, the physician will implant and position the caudal cup such that the upper bottom surface 153 of the caudal cup is approximately 25° posterior from the PEP (such that the surface is located approximately 115° from the CEP). This desired position will (1) maximize the flexibility of the prosthesis, allowing for maximal proper flexion and extension of the joint surfaces, and (2) provide a proportional amount of stability to the prosthesis to account for removal of any connective tissues that have occurred due to the implantation of the prosthesis as well as any other surgical procedures impacting the connective tissues of the treated area. FIG. 25B depicts a similar prosthesis implanted, with a portion of the spinous process of the caudal vertebral body removed to desirably allow unimpeded movement of the crossbar.

It should be understood that the angulation disclosed in this embodiment (approximately 25°) is desirably suited for replacement of the caudal facet joints of the L4 or L5 levels of the spine. Replacement of caudal facet joints in other levels of the spine might necessitate other varying angulations, as well as other orientations of the caudal and/or cephalad joint surfaces to accommodate torsional movement, flexion and extension, and/or lateral bending. In addition, depending upon the actual anatomy of the L4 or L5 levels, as well as the anatomy of adjacent levels, different angulation and/or orientation of the facet replacement prosthesis (other than that described herein) may be desired.

An inferior and posterior view of an embodiment of an adaptable spinal prosthesis 200 of the present invention are illustrated in FIGS. 26A and 26B. This embodiment of the adaptable spinal facet joint prosthesis 200 includes a crossbar 205 and a pair of cephalad prosthesis elements 220 coupled to a crossbar mount 275. The crossbar 205 has two ends 210, 215 engaged with a pair of caudal prosthesis elements 150. The adaptable prosthesis 200 has several features in common with the earlier described adaptable spinal prosthesis 100 and these components are similar to the above description. In the illustrated embodiments the cephalad bone engaging end 125 has been generalized and the caudal stems omitted for clarity.

The illustrated embodiment of the crossbar 205 has a first end 210, a second end 215 and a plurality of indexing features 206 along a portion of the outer surface. The indexing features 206 cooperatively engage with features 276 in the crossbar mount 275 to provide variable lateral alignment capability for the crossbar mount 275 relative to the crossbar 205. The plurality of indexing features may be in sections, two are illustrated in FIG. 26A, or the indexing features 206 may be spaced along the entire or a substantial portion of the width of crossbar 205. The illustrated embodiment of the indexing features 206 are aligned orthogonal to the width of the crossbar 205. Other angular relationships are possible and are within the scope of the invention. For example, the indexing features may form a lateral angle of 0 to 45 degrees relative to a line orthogonal to the width of the crossbar 205 measured between the two ends 210, 215. The illustrated embodiment of the crossbar 205 has a fixed width between ends 210, 215. Accordingly, crossbar 205 may be provided in a variety of different, fixed widths in order to achieve the adaptability advantages of the present invention. Alternative embodiments of crossbar 205 may include, for example, any of the adjustable width configurations described above such as threaded or slidably engaged (desirably incorporating a locking feature) crossbar pieces.

In the illustrated embodiment, there are provided a pair of cephalad prosthesis 220 having an end 240 adapted to engage the crossbar mount 275, an arm 245, an elbow 147 and a bone engaging end 125. The end 240 includes features 242 along the arm 245 for engaging with the outer surface of the crossbar 205. If desired, the crossbar could have a complementary feature to engage with feature 242. In the illustrated embodiment, the features 242 are threads. Other features such as knurling, barbs, surface roughing or other surface treatment or finish to increase the hold between the cephalad arm and the crossbar may be used. Similarly, the crossbar mount 275 could incorporate a triangular, square or other geometric shaped opening (not shown) to engage a complimentary surface (not shown) on the crossbar to reduce and/or eliminate rotation of the crossbar under loading conditions, if desired.

An exemplary embodiment of the crossbar mount 275 is illustrated in FIGS. 27A and 27B. The exemplary embodiment of the crossbar mount 275 includes a housing 277, a cephalad arm engaging portion 272, and a crossbar engaging portion 274. FIG. 27A is a view of the crossbar mount 275 along the cephalad arm engaging portion 272. The housing 277 includes a ridge 278 that engages with the threads of interior threaded cap 280 (see FIG. 26A). The cephalad arm portion 272 is sized and shaped to engage with the cephalad arm crossbar engaging end 240. FIG. 27B is a view of the crossbar mount 275 along the crossbar engaging portion 274. The crossbar engaging portion 274 is sized and shaped to engage with crossbar 205. Within the crossbar engaging portion 274 there is at least one complementary indexing feature 276. Indexing feature 276 is sized and shaped to form a cooperative mating with the crossbar indexing feature or features 206. While the indexing features 276 are illustrated as orthogonal to the crossbar 205 other angular orientations are possible as discussed above with regard to crossbar indexing features 206.

FIGS. 27C, 27D and 27E depict an alternate embodiment of a crossbar and cephalad bearing design and arrangement, which incorporates features allowing a physician to "preload" the prosthesis after implantation and prior to completion of the surgical procedure, desirably ensuring that the prosthesis is properly loaded to minimize and/or eliminate subsequent dislocation of the prosthesis. In this embodiment, the cephalad bearings 5000 incorporate off-center holes such that the center of each bearing is not coincident with the axis of rotation of the cross-arm 5010. When the cross-arm is rotated (after being fixed in place via connection to the cephalad arms/housings, etc.) (see FIGS. 27D and 27E), the cephalad bearings will also rotate at each end of the cross-arm. Because the center of each bearing is positioned off the rotational axis of the cross-arm, the subsequent rotation of the cross-arm results in a translation of the cephalad bearings (relative to the cephalad arm/cross connection). If the bearings are properly positioned relative to the cross-arm during initial placement of the caudal cups and cephalad arms (as shown in FIG. 27D), subsequent 180° rotation of the cross-arm can result in a net translation of L (see FIG. 27E). In such a case, proper rotation of the cross-arm can create a "preload" between the cephalad and caudal bearing surfaces. This embodiment could also be particularly useful in situations where some displacement of the cephalad bearings is desired, such as where the alignment of the components of the prosthesis is not optimal after initial implantation of the prosthesis. A further embodiment could incorporate a two or more-piece cross-arm allowing each cephalad bearing/cross arm section to be rotated, and thus displaced, independently of the other bearing.

If desired, the cross-arm can incorporate a hexagonal or other non-smooth intermediate surface which allows a tool to engage with and rotate the cross-arm against resistance that may be encountered. If desired, the cross arm may also be non-symmetrical (such as having a longitudinal "U" or "V" shape) to accomplish a similar goal with symmetrically-bored cephalad bearings, or a combination of both non-uniform cross-arm and non-symmetrically bored cephalad bearings may be used to accomplish the teachings of this invention.

Returning to FIG. 26A, an internally threaded cap 280 and set screw 282 are used to secure the cephalad arms, crossbar mount and crossbar into the desired position. The threaded cap 280 is secured to the housing 277 using ridge 278 once the cephalad arm has been positioned within the cephalad arm engaging portion 272 and the crossbar mount features 276 are engaged with the desired crossbar features 206. As the cap 280 advances, the cap 280 engages the cephalad arm 245 and urges the features 242 into engaging contact with the crossbar 205. At the same time, the housing 277 urges the indexing features 276 into contact with the crossbar indexing feature(s) 206. The cap 280 is tightened to a desired degree (and can include a breakaway feature to obtain a desired loading of the crossbar) and then secured with the set screw 282, if desired The modular prosthesis kit 290 (FIG. 18) may also be modified to accommodate embodiments of the adaptable spinal prosthesis 200. For example, the cross bar portion could include a plurality of crossbar 205 embodiments each having a different width. In addition, the crossbar mount 175 could also be modified to include the engagement elements 276 in the desired orientation. Also, the cephalad arms could be modified to include the desired embodiment of features 242.

Returning to FIG. 19, which is a flow chart illustrating one embodiment of a surgical method 300 for implanting an embodiment of an adaptable spinal prosthesis according to the present invention. The method 300 was described above with regard to one embodiment of a spinal prosthesis 100 of the present invention. The method 300 will now be discussed with reference to an embodiment of a spinal prosthesis 200. As previously noted, once the physician is prepared to implant the prosthesis, he/she can first estimate the amount of and remove a portion of the vertebral body, such as facet joints and pedicle, to allow for prosthesis implantation (310). (FIG. 20 illustrates vertebral bodies 40 and 45 after performing one embodiment of a procedural bone resection, a wide decompressive laminectomy, facetectomy and/or laminectomy). In this embodiment, the spinous process and inferior facet joints have been removed from the vertebra 40. The superior facet joints have been removed from vertebra 45 and the lamina shaped to produce caudal prosthesis receiving surfaces 74, 72. As illustrated in FIG. 21, holes are formed in the vertebra 40, 45 to prepare for cephalad and caudal stem implantation. Caudal stem holes 52 and 54 are formed in vertebra 45 and cephalad stem holes 56, 58 are formed in vertebra 40.

The physician can then size, select, test and set the caudal prosthesis (step 320). As described above, the adaptability of the orientation and position of the caudal prosthesis may be utilized to meet a wide variety of anatomical situations. It is to be appreciated that each of the adaptable characteristics of the caudal prosthesis including, for example, the stem angle Θc, the shape of the caudal stem head 162 and the shape of the caudal cup engaging surface 157 and the lengths of the caudal stem and distal end may each be used alone or in any combination to provide caudal stem variability into any orientation sagittally, axially, coronally or combinations thereof. The caudal prosthesis may be configured by selecting the desired caudal stem (see stems 160A-160E in FIG. 18), distal tip (if desired—see distal tips 170A-170E) and caudal cup 151 (see FIG. 18). FIG. 22 illustrates the selected caudal components after implementation. The caudal cups 151 are secured to caudal stems (not shown) that have been implanted into the caudal stem holes 52, 54 formed in the vertebral body 45.

Figure 28:
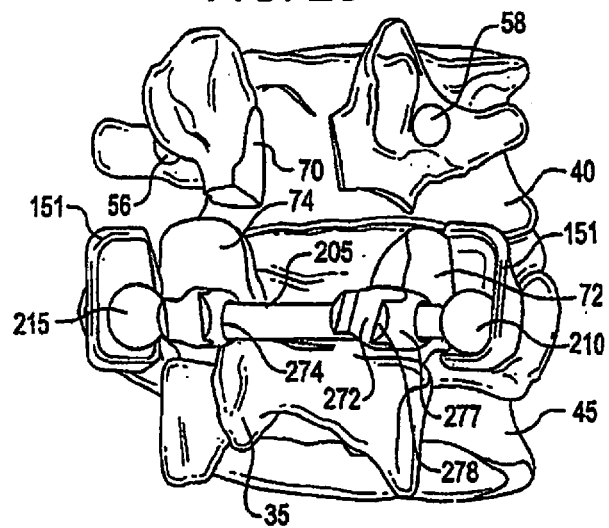
FIGS. 28-29 illustrate a method for implanting the prosthesis of FIGS. 26A-B.

Size, select, test and adjust the crossbar (step 330). The crossbar 205 is selected based on the distance between the caudal cups 151. The crossbar may be configured by selecting from a plurality of crossbar 205 embodiments each having a different width. Typical fixed width crossbars 205 may have a width ranging from 37 to 67 mm, and have a thickness of approximately 5 mm and different width increments increasing by 1 or 2 mm for each different crossbar. As discussed above, in an alternative embodiment where adjustable crossbars 205 are used, the width of the crossbar 205 may be selected initially to place the crossbar ends 215, 210 against the caudal cup receiving surface 155. The crossbar width is adjusted into final position using the adjustable crossbar members 104, 106 and a threaded portion 109. FIG. 28 illustrates an embodiment of a cross bar 205 in place against caudal cups 151. The crossbar mounts 275 are present with the crossbar 205 disposed within the crossbar engaging portion 274.

Figure 29:
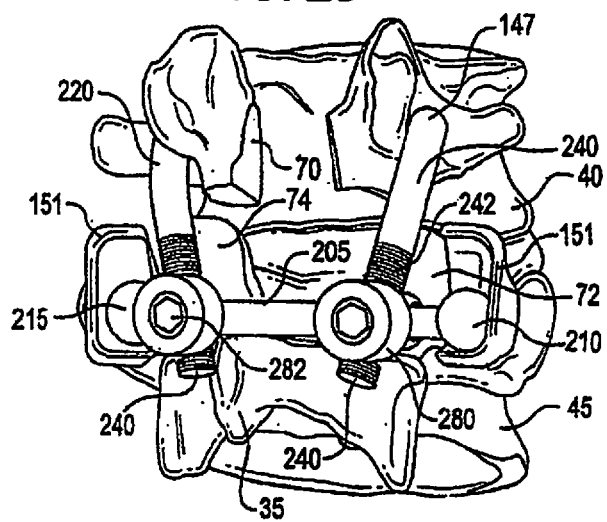

Size, select, test and set the cephalad prosthesis (340). Referring initially to FIG. 28, the cephalad prosthesis 220 is adapted to have the crossbar engaging end 240 engage with the crossbar cephalad engaging portion 272 and the bone engaging end 125 (not shown) engaged within the lamina via holes 56, 58. Within these parameters the cephalad arms 220 are configured and adapted by selecting, at least, the desired distal tip 135 length (see distal tips 135A-135E in FIG. 18), and cephalad stem 130 length (i.e., cephalad arms 120A-120C in FIG. 18 modified to include an embodiment of the engagement features 242). As described above with cephalad prosthesis elements 120, in some embodiments of the cephalad elements 220, elbow angle and arm length may also be selectable characteristics. As illustrated in FIG. 29, the cephalad arms cross bar engaging ends 240 are secured by cap 280 and fixation element 282 to the cross bar mount cephalad engaging portion 272. In addition, the cephalad arm 245 has also secured the crossbar relative to crossbar mount 275 utilizing the features 242. At the same time, but not illustrated in FIG. 29, tightening the cap 280 also urges the crossbar indexing features 206 into locking cooperation with the crossbar housing indexing feature 276 to secure the crossbar housing 275 in position between crossbar ends 210, 215. Also illustrated is the independence of cephalad arm and crossbar mount adaptability. In this embodiment, it should be appreciated that the cephalad arm end 240 in the crossbar mount adjacent the end 210 can extend beyond the crossbar mount casing 277 a greater, equal or lesser length than the length the cephalad arm end 240 extends beyond the crossbar mount casing 277.

FIGS. 30A and 30B illustrate alternative crossbar mounts 500, 550. Each of the mounts 500, 550 provide adaptability related to cephalad arm height ("h"), cephalad arm rotation ("r") and crossbar mount lateral position ("L") and rotation. Crossbar and mount 500 includes a central mount 520 including a pair of articulating mounts 525 shown with a portion of a pair of cephalad arms 545 extending therefrom. While only a portion of the cephalad arms 545 is illustrated, it is to be appreciated that the crossbar mounts 500 and 550 function with all of the earlier described embodiments of the adaptable spinal prosthesis described above including the adaptable caudal and cephalad prosthesis element embodiments. Moreover, while crossbar 505 is illustrated as a fixed width crossbar, it is to be appreciated that the earlier described adjustable width crossbar concepts may also be applied to embodiments of crossbar 505.

The central mount 520 is illustrated in a position between the ends 510, 515 and secured to a crossbar 505. The central mount 520 may be adjusted laterally ("L") between the ends 510 and 515 by engaging the desired set of complementary engaging elements 504, 506. Engaging elements 504 are located within the central mount cross arm engaging portion 574. Engaging elements 506 are located on crossbar 505. The engaging elements are positioned to allow not only lateral movement but also rotation of the central mount about the crossbar 505. Once the central mount is in the desired position and orientation, the position of the central mount 520 relative to the crossbar 505 may be secured using fastener 508.

The central mount 520 includes a pair of articulating mounts 525 that provide adaptable, independent cephalad arm height ("h") and cephalad arm rotation ("r") for each cephalad arm 545. Separate engaging elements are provided within a mount 525 and between the mount 525 and central mount 520 to maintain the desired height and rotation settings for each cephalad arm 545. Cephalad arm height is maintained by engaging the desired mount engaging elements 532 with the desired cephalad arm engaging elements 530. Once the desired elements are aligned, the engaging elements are locked using the locking element 535. Locking element 535 articulates the engaging elements between an "unlocked" configuration and a "locked" configuration. The unlocked configuration is illustrated in the mount 525 adjacent the end 510 and the locked configuration is illustrated in the mount 525 adjacent the end 515. Cephalad arm rotation is achieved by adjusting the position of the articulating mount engagement elements 534, 536. Engagement elements 534 are distributed along the proximate edge of the articulating mount 525. Central mount engagement elements 536 are distributed along the interior of the central mount 520. Once the desired rotational orientation of the cephalad arm 545 relative to the central mount 520 is achieved, the engagement elements 534, 536 are secured using fastener 538.

An alternative crossbar mount 550 is illustrated in FIG. 30B. Central mount lateral position ("L") and rotation operate similar to crossbar mount 500. Crossbar mount 555 includes two internally articulating, lockable cephalad arm mounts 560. The internally articulating, lockable cephalad arm mounts 560 combine the adaptability features of the cephalad arm height ("h") and cephalad arm rotation ("r") in a single adjustment and locking mechanism. The single adjustment and locking mechanism is provided by a plurality of lockable elements 562 that may be articulated between and "unlocked" and "locked" configuration by the locking driver 564. The locking elements are formed from a biocompatible polymer or other suitable material to compress against and grip the cephalad arms 545 when secured by the locking driver 564. The locking driver 564 may be, in one exemplary embodiment, a band encircling the elements 562 in a first position in an unlocked configuration and in a second position in the locked configuration. In another exemplary embodiment, the locking driver is a clamp ring. The elements are shaped with relative orientations to allow cephalad arm movement to adjust arm height and rotation. When the locking driver 564 is positioned into the "locked" configuration, the elements 562 are gradually engaged so as not to alter the desired height and rotation alignments. The locking elements 562 are illustrated in an "unlocked" configuration in the mount 560 adjacent the end 510. The locking elements 562 are illustrated in a "locked" configuration in the mount 560 adjacent the end 515. The mount 560 interior is sized to allow for angular movement and height adjustments of the cephalad arm 545.

FIGS. 31A to 32D illustrate embodiments an adaptive spinal prosthesis of the present invention having alternative embodiments of the crossbar component. These adaptive spinal prosthesis embodiments each include caudal cups and stems as well as cephalad arms having elbows, stems and distal ends similar to the earlier described embodiments. For clarity, similar or simplified reference number designations are used to designate these earlier described components. In addition, these components will be represented simplistically rather than with full details as before.

FIG. 31A illustrates an embodiment of an adaptive spinal prosthesis 300A having a crossbar 310. The adaptive spinal prosthesis 300A includes a pair of cephalad arms each having a cephalad bearing 305 on the proximate end. The crossbar 310 is attached to one cephalad arm 145 using fixed clamp 312 and fastener 313. The clamp 312 may be positioned along the cephalad arm 145 until the clamp 312 and, in turn, the crossbar 310, is positioned in the desired spacing between the cephalad bearing 305 and the elbow 147. Clamp slide assembly 314 includes a piston 318, joined to clamp 316 using the fastener 315. The clamp slide assembly 314 provides crossbar width adjustment as well as cephalad bearing-elbow spacing for the clamp 316. The clamp 316 secures the clamp slide assembly 314 (including the crossbar 310) to the cephalad arm 145 in the desired position between the cephalad bearing 305 and elbow 147. The piston 318 is slidably engaged with the crossbar 310. In operation the piston 318 slides along the crossbar 310 to the desired crossbar width. Once the desired crossbar width and cephalad bearing-elbow spacing are obtained, the fastener 315 is tightened. Tightening the fastener 315 secures the crossbar 310 within the piston 318 and the cephalad arm 145 within the clamp 316. In the illustrated embodiment, the clamp 312 and the clamp 316 engage the cephalad arms 145 between the bearing 305 and the elbow 147 in a position leaving the crossbar 310 forming an angle of about 90 degrees with each of the cephalad arms 145. It is to be appreciated that the clamps 312, 316 operate independently and that the ends of crossbar 310 may attach to the cephalad arms 145 in a configuration where the crossbar 310 forms an angle of other than 90 degrees with each of the cephalad arms 145. In the illustrated embodiment, the crossbar 310 lays in a plane below a plane that contains both cephalad arms 145.

Figure 31B:
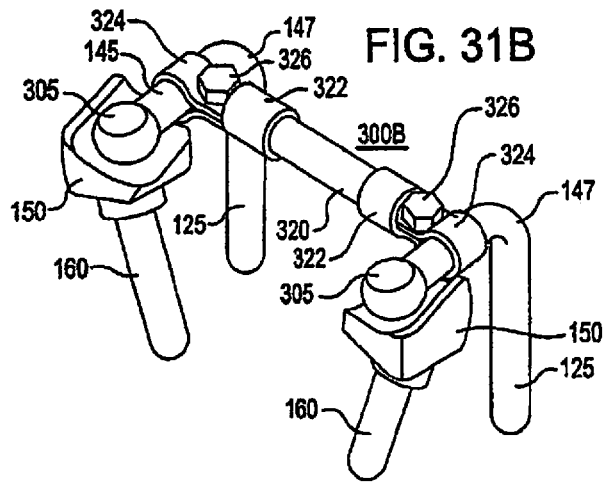

FIG. 31B illustrates an embodiment of an adaptive spinal prosthesis 300B having a telescoping crossbar 310. The telescoping crossbar 320 includes telescoping sections 322 that are attached to clamps 324. Clamps 324 are adjustably engaged about the cephalad arms 145 between the bearing 305 and the elbow 147. Fasteners 326 are used to secure the clamps 324 to the cephalad arms 145. The width of telescoping crossbar 320 may be adjusted as the telescoping sections 322 move towards or away from fasteners 326. Once the telescoping crossbar 320 width is selected, tightening fasteners 326 secures the crossbar clamps 324 about the cephalad arms 145 and locks the position of the telescoping sections 322 in the selected width. In the illustrated embodiment the crossbar 320 lies in a plane that contains the cephalad arms 145.

Figure 31C:
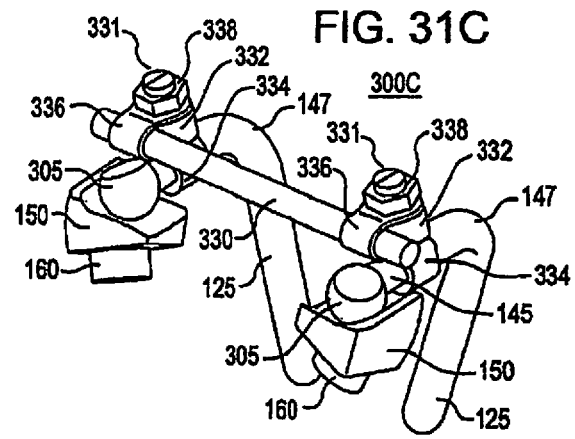

FIG. 31C illustrates an embodiment of an adaptive spinal prosthesis 300C having a crossbar embodiment 330 and crossbar locks 331. A crossbar lock 331 includes a cephalad arm clamp 334 about a cephalad arm 145 and a crossbar clamp 336 that encircles the crossbar 330. A dual clamp housing 332 and fastener 338 join the clamps 334, 336. The width of crossbar 330 is determined by moving the crossbar 330 relative to the crossbar clamps 336. The crossbar spacing between a cephalad bearing 305 and an elbow 147 is determined by moving the cephalad arm clamp 334 along the cephalad arm 147 to the desired position. Once the width of crossbar 330 and the position of the crossbar 330 relative to the bearing 305 and the elbow 147 are selected, the crossbar 330 is secured into the selected position by tightening the fastener 338. Tightening fastener 338 results in articulation within dual clamp housing 332 to tighten both the arm clamp 334 about the cephalad arm 145 and the crossbar clamp 336 about the crossbar 330. In the illustrated embodiment the crossbar 330 is positioned in a plane above a plane that contains the cephalad arms 145, but the crossbar 330 could alternatively be even with or below the plane containing the cephalad arms 145 (or any combination thereof).

Figure 31D:
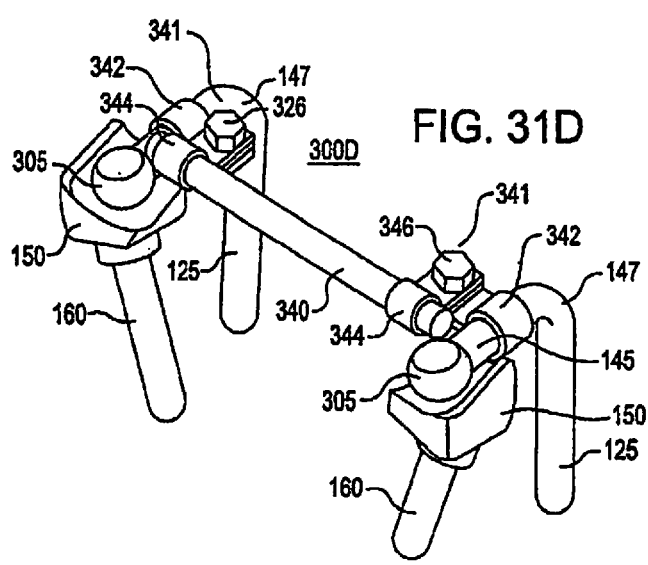

FIG. 31D illustrates an embodiment of an adaptive spinal prosthesis 300D having a crossbar embodiment 340 with crossbar locks 341. A crossbar lock 341 includes a cephalad arm clamp 342, a crossbar clamp 344 and a fastener 346. The position of the crossbar 340 between the cephalad bearing 305 and the elbow 147 is changed by sliding the arm clamps 342 along the cephalad arms 147. The crossbar width between the crossbar clamps 344 is adjusted by sliding the crossbar 344 relative to the clamps 344. Once the position of the crossbar 340 between the cephalad bearing 305 and the elbow 147 and the width of the crossbar 340 are selected, the crossbar position is secured by tightening fastener 346. Tightening fastener 346 urges the arm clamp 342 about the cephalad arm 145 and the crossbar clamp 344 about the crossbar 340. In the illustrated embodiment, the crossbar 340 is contained in a plane above a plane that contains the cephalad arms 145, though it could be even with or below the plane containing the cephalad arms 145, if desired. In the illustrated embodiment, the arm clamp 342 and the crossbar clamp 344 and the fastener 346 are configured to form a 90 degree angle. In alternative embodiments of the crossbar 340, angles other than 90 degrees may be formed by the crossbar clamp 344, fastener 346 and arm clamp 342.

FIG. 31E illustrates an embodiment of an adaptive spinal prosthesis 300E having a crossbar embodiment 350. The crossbar 350 includes a base end 352 and an articulating end 353. Each of the base end 352 and the articulating end 353 include arm clamps 354. Arm clamps 354 are each secured to a corresponding cephalad arm 145 by tightening of a set screw 357. The articulating end 353 is slidably connected to the base end 352, with the ends 353, 352 similarly secured relative to each other by tightening of a set screw 358. One advantage of the crossbar 350 is that the articulating end 353 is free to rotate, telescope and articulate about the cephalad arm 145 and move relative to the base end 352.

In contrast to attaching the crossbar using a slideable cephalad arm clamp attachment as in spinal prosthesis 300A-300E, the following spinal prosthesis embodiments 400A-400D utilize attachment points at or adjacent the cephalad bearing 305. FIG. 32A illustrates an embodiment of an adaptive spinal prosthesis 400A having a crossbar embodiment 410. Crossbar arm clamps 412 are attached to cephalad bearing 405 using a fastener 414 placed into a threaded receiver within cephalad bearing 405. Cephalad bearing 405 is threaded to receive fastener 414. When the width of the crossbar 410 between the clamps 412 and the cephalad arms 145 is in the desired position, the fastener 414 is tightened securing the clamp 412 about the crossbar 410 and the clamp 412 relative to the cephalad bearing 405. In the illustrated embodiment, the clamps 412 are configured to provide the crossbar 410 within a plane that contains the cephalad arms 147. In this specific embodiment, the crossbar 410 lies at approximately the mid-height of the cephalad arms 147.

FIG. 32B illustrates an embodiment of an adaptive spinal prosthesis 400B having a crossbar embodiment 420 with crossbar clamps 422. Crossbar 420 includes clamps 422 that attach about the ends of crossbar 420 and to the cephalad bearing 405 using fastener 424. The cephalad bearing 405 is desirably threaded or otherwise configured to receive the fastener 424. The crossbar 420 width is adjustable between the clamps 422. Once the desired crossbar width is selected, the fastener 424 is tightened. When the fastener 424 is tightened, the clamp 422 secures about the crossbar 420 and the clamp 422 is secured relative to the cephalad bearing 405. The cephalad bearing 405 is threaded to receive the fastener 424. In the illustrated embodiment, the clamps 422 are configured such that, when secured to the cephalad bearings 405, the crossbar 420 is located in a plane above the plane containing the cephalad arms 145 and the clamps 422 are positioned between the cephalad arms 145.

Figure 32C:
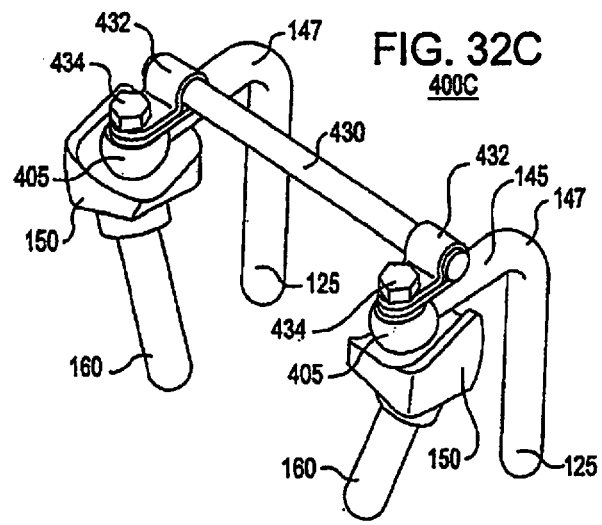

FIG. 32C illustrates an embodiment of an adaptive spinal prosthesis 400C having a crossbar embodiment 430 with crossbar clamps 432. The crossbar clamps secure the crossbar to the cephalad bearing 405 using the fastener 434. The cephalad bearing 405 is threaded or otherwise configured to receive the fastener 434. In the illustrated embodiment, the crossbar clamps 432 are in line with the cephalad arms 145. The crossbar is positioned between the clamps 432 to the desired width. Once the crossbar is positioned in the desired width, the fastener 434 is tightened. When the fastener 434 is tightened, the clamp 432 is secured about the crossbar 430 and to the cephalad bearing 405.

Figure 32D:
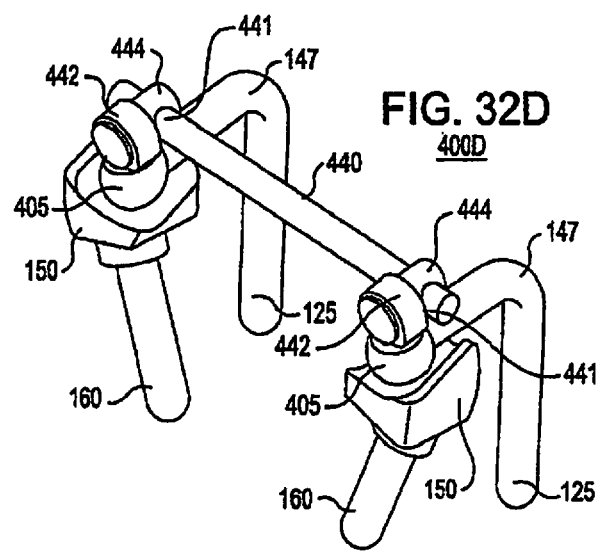

FIG. 32D illustrates an embodiment of an adaptive spinal prosthesis 400D having a crossbar embodiment 440 with a locking system 441. A locking system 441 includes a crossbar lock 444 and a cephalad bearing lock 442. Each end of the crossbar 440 is secured to a cephalad bearing 405 using a locking system 441. Once the width of crossbar 440 between crossbar locks 444 is selected, then the cephalad bearing lock 442 is pressed into the cephalad bearing 405. This same motion secures the crossbar lock 444 about crossbar 440 and the bearing lock 442 about the crossbar lock 444.

In alternate embodiments, the crossbar could comprise a plurality of crossbars. For example, a first crossbar could fasten to the right side cephalad bearing with a crossbar attached between the bearing and elbow of the left side cephalad arm. The second crossbar could be fastened to the left side cephalad bearing with a crossbar attached between the bearing and elbow of the right cephalad arm. Where the first and second crossbars cross, they could pass above and below one another without contact or a bearing/securement surface could be located where the first and second crossbars intersect. Alternatively, a pair of parallel crossbars, either adjacent to one another or spaced apart, connecting the cephalad arms to each other, could be used. Moreover, in embodiments where only a single side of the facet joints in a vertebral body are replaced, a crossbar could secure the cephalad and/or caudal arms (or both) to the lamina and/or the spinous process. In a similar manner, the caudal prostheses could incorporate a crossbar or other arrangement to link the two caudal prostheses together in a like manner.

While the above exemplary adaptive spinal prosthesis and crossbar embodiments have been shown and described with certain features, other embodiments and alternatives are also within the scope of the invention. For example, the crossbar shape has been illustrated as having a circular or rectangular cross section. Other cross sectional shapes are possible such as, for example, polygonal, hexagonal, or other suitable shapes. Additionally, crossbar orientation between the crossbar and the cephalad arms has been described as being above, within, or below a plane that contains the cephalad arms 147. It is to be appreciated that each of the described embodiments may be modified to provide any or all of these crossbar-cephalad arm configurations. Crossbar width may also be modified to provide thicknesses and crossbar widths other than those illustrated. The crossbar position relative to the cephalad bearing and cephalad arm elbow may also vary from the illustrated embodiments and may be positioned into configurations below, on top of, or above the cephalad bearing as well as positioned between the cephalad bearing and the elbow, and including positions adjacent the elbow 147. It is to be appreciated that while each of the above listed crossbar embodiments is illustrated with a straight crossbar, conventional rod bending techniques may be utilized to shape the crossbar into a desired configuration further expanding the adaptability aspect of embodiments of the present invention. In the exemplary embodiments, the clamps joining the crossbar to the cephalad arms engage the cephalad arms 145 in a manner where the crossbar forms an angle of about 90 degrees with each of the cephalad arms 145. It is to be appreciated that the clamping systems and elements described herein operate independently and that the ends of crossbar may attach to the cephalad arms 145 in alternative configurations, such as, for example, where the crossbar forms an angle of other than 90 degrees with the cephalad arms 145.

Earlier described embodiments of caudal fastener 160 and cephalad bone engaging end 125 have in common a generally linear geometry and similar distal tips 170, 135. However, embodiments of the caudal fastener 160 and cephalad bone engaging end 125 may be modified to include one or more or combinations of anti-rotation and anti-pull out features. These additional features are described below with reference to FIGS. 33A-36C. Irrespective of the design and configuration of the following exemplary embodiments, the principals illustrated in the embodiments of FIGS. 33A-36C are applicable to both caudal and cephalad fasteners even though a feature or design principal may be shown or described as it may be utilized in either a caudal fastener or a cephalad fastener. For example, FIGS. 35A-35D illustrate an anti-rotation paddle in an embodiment of a cephalad prosthesis similar to the cephalad prosthesis illustrated in embodiments of the spinal prosthesis 200 (i.e., FIGS. 31A-32D). However, the anti-rotation paddle may be utilized with embodiments of the caudal fastener and/or embodiments of the cephalad element in spinal prosthesis 100.

Figure 33A:
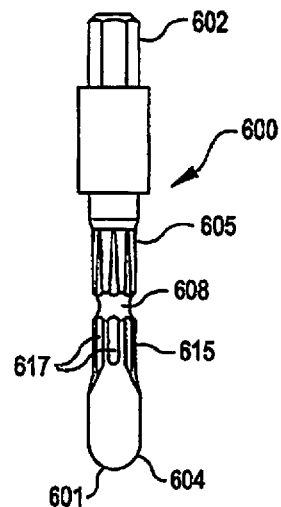
Figure 33B:
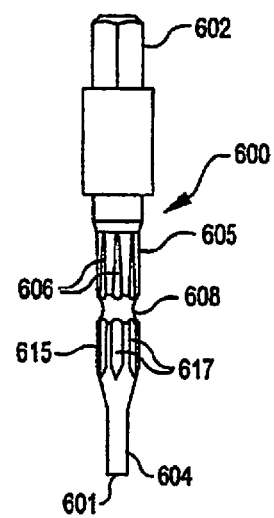

FIGS. 33A, 33B, and 33C show an embodiment of a stem 600 with a paddle 604 and grooves as anti-rotation element(s). The stem 600 may be modified to act as a bone engaging end of an embodiment of a cephalad prosthesis element or as a fixation element for an embodiment of a caudal prosthesis. While desiring not to be bound by theory, it is believed that the wide surface area(s) provided by the anti-rotational paddle embodiments of the present invention provide greater resistance to the torque loads applied to the prosthesis and attempted rotation of the paddle within the vertebra. For example, the addition of surface projections and/or pits can significantly increase the total surface area of the prosthesis, thereby increasing the ability of any adhesion between the prosthesis and the surrounding material (such as bone cement, epoxy or in-growing bony material) to secure the prosthesis in position. As another example, the addition of surface projections and pits can interact with the surrounding material to create a geometric or mechanical "interlock" that resists relative motion between the prosthesis and the surrounding material. As such, the paddle embodiments of the present invention described herein act as improved anti-rotational and/or anti pull-out elements. Similarly, other anti-rotation elements described herein are also used to counteract the torque and/or axial loads developed within and acting upon various portions of vertebral prosthesis.

The stem 600 has a distal end 601 and a proximal end 602. The proximal end 602 may be configured to accept tooling and instruments to secure the stem 600 into the vertebra and/or to provide an attachment point to another component within an embodiment of an adaptable spinal prosthesis of the present invention. The distal portion of the stem 600 includes a paddle 604 configured to act as an anti-rotation element to prevent the rotation of the stem 600 once implanted into a portion of the spine. Alternative embodiments of the stem 600 can have multiple paddles. Although the illustrated paddle 604 has a rounded profile, alternative embodiments may have different profiles including, for example, one or more corners. Although the illustrated paddle 604 is flat, alternative embodiments can have nonflat contours, with one or more concave and/or convex features.

FIGS. 33A, 33B, and 33C also illustrate an embodiment of an anti-pull out feature of the stem 600. Embodiments of the stem 600 also include anti-pull out features. As used herein, an anti-pull out feature refers to an element or combination of elements of a prosthesis portion or fastener acting to mitigate, minimize or counteract forces bearing upon the prosthesis portion or fastener to disengage, loosen, advance, pull or otherwise axially translate the fastener relative to a desired position on or within the vertebra. (For purposes of this disclosure, anti-pullout forces can be interpreted to include, but are not limited to, both "pull" and "push" forces, as well as components of various twisting and/or rotational forces, which serve to translate the prosthesis along a longitudinal axis outward or inward relative to the targeted vertebral body.) In the illustrated embodiment, the stem 600 includes a proximal grooved portion 605 having proximal grooves 606 and a distal grooved portion 615 having distal grooves 617. In the illustrated embodiment, proximal grooves 606 have a proximal tip with a width that increases distally and distal grooves 617 have a nearly constant width terminating in a distal tip. A reduced diameter portion 608 separates the proximal grooved portion 605 from the distal grooved portion 615. The proximal grooves 606, distal grooves 617 and reduced diameter section 608 act to increase the surface area of the vertebral prosthesis portion 600. Increasing the surface area of the stem 600 provides greater attachment between the stem 600 and the vertebra. The greater amount of surface area may be used advantageously with bone cement, bone growth compounds or other materials used to bond the external surfaces the stem 600 to the interior of the vertebra. The greater surface area allows, in embodiments where bone fixation cement is used, more cement to be present along the length and a particularly greater amount of cement or fixation material to be present about the reduced diameter section 608. The increased amount of cement present adjacent the reduced diameter portion 608 (and increased thickness of the cement mantle in these areas) produces a section of increased diameter that strengthens the overall mantle and/or counteracts pull out forces. Other configurations, arrangements and geometries of the proximal grooved portion 605, reduced diameter portion 608, and distal grooved portion 615 are possible. For example, different groove configurations are possible (e.g., FIGS. 34A, 34B, 36A, 36B and 36C), there may be multiple distal or proximate grooved portions, multiple reduced diameter portions or different paddle configurations (e.g., FIGS. 35A-35D).

FIGS. 34A and 34B illustrate an alternative embodiment of stems 900, 990 having anti-rotation and anti-pullout elements. The paddle 955 and proximal ridges 925, 927 act as anti-rotation elements. The reduced diameter section 940, grooved sections 930, 945 and reduced shank diameter 920, 922 act as anti-pullout elements. The stems 900 and 990 are similar in many regards to stem 600 of FIGS. 33A, 33B and 33C. However, several differences are worth noting. Paddle 955 has a flat face 960 but a rounded, tapered distal end 965 instead of a flat distal edge found on paddle 604 (see FIG. 33B). Proximal grooves 935 have a constant width instead of a tapered width (see FIG. 33A grooves 606). Distal grooves 950 have a uniform width and a rounded distal end instead of a distal tip (grooves 617 of FIG. 33B).

One notable difference between the stems 900, 990 and the stem 600 is the addition of the proximal anti-rotation sections 920, 922. The proximal anti-rotation sections 920, 922 include a shank having a diameter less than the shank 915 and a plurality (two in the illustrated embodiments) of ridges that act as proximal anti-rotation elements. Stem 900 has a proximal anti-rotation portion 920 and ridges 925 having an overall height h1. Stem 990 has a proximal anti-rotation portion 922 and ridges 927 having an overall height h2. These embodiments advantageously provide reduced shank sizes thereby allowing for increased cement mantle (if cement is desired), while still providing a mechanical "interlock" with the surrounding tissue that resists prosthesis rotation—in various embodiments, the ridges can desirably engage surrounding cortical bone at the pedicle entry point, which is often stronger than the cancellous bone contained within the vertebral body, although the ridges' engagement with either or both types of bone will serve to resist rotation to varying degrees. In a specific embodiment of the stem 900 the height h1 is 8.25 mm and the proximal anti-rotation section diameter is 6.5 mm but still desirably maintains a moment of inertia (Iy) approximately equal to that of a 7 mm rod. In a specific embodiment if the stem 990, the overall ridge height h2 is 8.75 mm and the proximal anti-rotation section diameter is 6.0 mm but the embodiment still desirably maintains a moment of inertia (Iy) approximately equal to that of a 7 mm rod.

It is to be appreciated that the stems 900 and 990 may differ from the illustrated embodiments. For example, there may be one or more ridges present in the proximal anti-rotation sections (as opposed to the pair of ridges disclosed above). The additional ridges need not have uniform cross sections or be uniformly spaced about the perimeter of the proximal anti-rotation section. The paddle face 960 may have a different face such as convex, concave or other compound shape or combinations thereof.

FIGS. 35A-D show an embodiment of a cephalad arm 700 with a fixation element having a bend 710, and a paddle 704 as an anti-rotation element, similar to the stem 600 of FIGS. 6A, 6B, and 6C. The cephalad arm 700 includes a distal end 701 and a proximal end 703. The proximal end 703 includes a bearing element 715 for engagement to other portions of the vertebral prosthesis. To accommodate a number of different facet joint prosthesis configurations, the fixation element includes a bend 710 connected to a shaft 735 having a paddle 704 attached thereto.

The cephalad arm 700 also illustrates another aspect of the adaptable and configurable concepts of the present invention. For example, in some embodiments, the shaft 735 is detachably fastened to the attachment point 740. The shaft 735 has a length "l" between the attachment point 740 and the proximate end of the paddle 704. The shaft 735 is detachably coupled to the attachment point 740 to allow for shafts 735 of different lengths to be used 40 with different configurations of the cephalad arm 700 thereby providing a modular vertebral prosthesis. As such, in use, the shaft 735 may be detached from the attachment point 740 and replaced with a shaft 735 having a different length "l" as needed until the proper alignment of the vertebral prosthesis is achieved. The highly configurable and modular components of embodiments of the spinal prosthesis of the present invention can be attached to the prosthesis using one or more attachments methods well known in the art, including threaded screws, Morse (or other types) tapers, welding, adhesives or set screws.

While the modular concept has been described with regard to the vertebral prosthesis 700, it is to be appreciated that other embodiments of the cephalad arm 700 described herein may have a portion or portions that are detachably coupled in furtherance of the configurable, adaptable spinal prosthesis concepts of the present invention. For an alternative example, the shaft 735 may be of fixed length and permanently attached to the attachment point 740 while the detachable attachment point is positioned between the shaft 735 and the paddle 704 thereby allowing paddles 704 of different lengths to be used. In yet another alternative, both the shaft and the paddle may have detachable attachment points thereby allowing various shaft lengths and configurations and paddle lengths and configurations to be used in furtherance of the modular spinal prosthesis concepts described herein. It is to be appreciated that the detachable attachment point may be positioned between any portion or portions of the embodiments of the spinal prosthesis portions described herein. Similarly, the anchoring devices may comprise pedicles screws or other similar modules which provide a solid anchor to the vertebral body, which can in turn be attached to various modules that either (1) replace the facet joint structure (allowing for motion) or (2) immobilize the facet joint structure (as an adjunct to spinal and/or facet joint fusion). In addition, the anchoring devices could incorporate multi-axial heads/connection mechanisms to accommodate the various articulating components.

In an alternate embodiment, one or more sections of the stem or cephalad arm prosthesis may be made of a deformable or shape-memory material (such as Nitinol or similar materials), which permits the physician to make adjustments to the prosthesis geometry to "form-fit" the implant to the patient's specific anatomy. In the case of Nitinol, the material can be heated or cooled away from the body temperature (depending upon the type of material and it's martensitic/austenitic properties), be deformed to a desired shaped, and then held in the deformed position and allowed to return to the body temperature, thereby "hardening" into the desired shape or form. Such an embodiment would facilitate a reduction in the number of sections or "modules" required for a modular prosthesis, as each module could assume a variety of desired positions.

While the angle of the illustrated bend 710 is acute, other embodiments of the cephalad arm 700 can have a bend 710 having a right angle or an obtuse angle. Alternative embodiments of the cephalad arm 700 may include two, three, or more bends 710. In the illustrated embodiment, the paddle 704 has a flat surface 720 and a proximal end having a transition portion 730. The flat surface 720 is illustrated in the same plane in which the fixation element has the bend 710. In other embodiments, the paddle 704 has a flat surface 720 in another plane, and/or a nonflat contour, with one or more concave and/or convex features or have paddle shapes (the flat surface 720 can be at virtually any angle relative to the angle of the elbow, including perpendicular to or parallel to the bend 710). The transition portion 730 has a width that decreases linearly in a proximal direction. Other configurations of the transition portion 730 are possible for transitioning from the paddle 704 to the shaft 735 of the vertebral prosthesis portion 700. The alternative shapes of the transition portion include, for example, a non-linear decreasing proximal width, asymmetric portions, curved portions or compound portions.

FIGS. 36A and 36B show an embodiment of a cephalad arm 1400 with helical longitudinal depressions as anti-rotation elements and a fixation element with a bend. The illustrated embodiment of the cephalad arm 1400 has a distal tip 1404 and a proximal end 1402. The proximal end 1402 includes a socket element 1407 for further attachment to a vertebral prosthesis component. In an alternative embodiment, the element 1407 could comprise a cephalad bearing surface for slidably engaging a corresponding caudal cup as described above with regard to an embodiment of a spinal prosthesis of the present invention. Proximal shaft 1415 is attached to the socket element 1407 and the bend 1410. The tapered section 1430 transitions from the proximal shaft 1415 to the distal shaft 1417. The proximal shaft 1415 is a different diameter than the distal shaft 1417. Other transitions are possible such as a stepped transition (e.g. section 740 of FIG. 35B) or no transition if the diameter of the shafts 1415 and 1417 are the same.

The distal shaft 1417 includes a plurality of longitudinal depressions 1423 extending from the distal end 1404 to a point beyond the tapered section 1430. The proximal end of the longitudinal depressions 1423 has a bulbed section 1460. The distal shaft 1417 also includes a reduced diameter section 1440. The reduced diameter section 1440, longitudinal grooves 1423 and bulbed section 1460 may be used to increase the surface area of the vertebral prosthesis portion 1440 that is, when implanted, within a vertebra of the spine. The increased surface area allows for more area to support the cement mantle for applications using cement or bony in-growth for applications using bone ingrowth. It is to be appreciated that the longitudinal grooves 1423 may also be varied as described elsewhere with regard to other grooves and, for example, as described with regard to FIGS. 33A-33C. In addition, alternative embodiments of bend 1410 are possible as described with regard to FIGS. 35A-35D.

It is to be appreciated that each of the longitudinal depressions 1423 has a longitudinally varying profile, narrowing as the longitudinal depression extends proximally. In alternative embodiments, the longitudinally varying profile can widen or remain constant as the longitudinal depression extends proximally. Although in the illustrated embodiment all of the longitudinal depressions are identical, in other embodiments, the multiple longitudinal depressions can differ, for example by having different profiles, lengths, starting and/or ending points, etc. Alternative embodiments can have one longitudinal depression, two longitudinal depressions, four longitudinal depressions, five longitudinal depressions, or more longitudinal depressions.

FIG. 36C depicts an alternate embodiment of the vertebral prosthesis of FIGS. 36A, 36B in which a pair of cephalad prosthesis arms 1400 are connected by a cross-bar 1405. The crossbar 1405 provides yet another alternative arm attachment in addition to the crossbar-cephalad arm attachment embodiments illustrated in FIGS. 31A-32D. Cross-bar 1405 can be a cylindrical member fitting into openings 1409 in each of the shafts 1415 of the prosthesis arms 1400 (or can be virtually any rigid or semi-rigid member secured between the two prosthesis arms), and the cross-bar 1405 desirably reduces or prevents rotation of the prosthesis arms 1400 relative to each other. When both of the prosthesis arms are secured into a targeted vertebral body through the pedicles (not shown), any torsional loads experienced by an individual prosthesis arm 1400 will be transferred to the shaft 1415 of the opposing prosthesis arm by the cross-bar 1405, which will convert the torsional load to a transverse load acting on the opposing prosthesis. Desirably, the newly loaded prosthesis arm can resist this transverse force, thereby maintaining the entire structure in a desired position. In this embodiment, the cross-bar therefore "shares" and redistributes the torsional loading experienced by an individual prosthesis arm, significantly reducing the tendency for an individual prosthesis arm to deflect and/or rotate. In an alternative embodiment the crossbar 1405 may have an adjustable portion that allows adjustment in the width between the cephalad prosthesis arms 1400.

Additional anti-pull out and anti-rotation embodiments and disclosures are described in commonly assigned U.S. patent application to Tokish et al. entitled "Anti-Rotation Fixation Element for Spinal Prostheses," Ser. No. 10/831, 657, filed Apr. 22, 2004, the entirety of which is incorporated herein by reference for all purposes.

Additional trialing embodiments and disclosures are described in commonly assigned U.S. patent application to Augostino et al entitled "Facet Joint Prosthesis Measurement and Implant Tools," Ser. No. 10/831,651, filed Apr. 22, 2004, the entirety of which is incorporated herein by reference for all purposes.

In further embodiments, one or more surfaces of the embodiments of the spinal prosthesis of the invention may be covered with various coatings such as antimicrobial, antithrombotic, and osteoinductive agents, or a combination thereof (see, e.g., U.S. Pat. No. 5,866,113, which is incorporated herein by reference). These agents may further be carried in a biodegradable carrier material with which the pores of the stem and/or cup member of certain embodiments may be impregnated (see, e.g., U.S. Pat. No. 5,947, 893, which is also incorporated herein by reference).

Laminar Reinforcement

In various alternative embodiments (shown, e.g., in FIGS. 39A-F), modular joint replacement prostheses 3100 provided herein are installed, with or without the use of cement, on one or more spinal levels (i.e., on multiple spinal levels).

In addition, implantation of the joint replacement prostheses of the present invention can be augmented such that these prostheses are also attached to one or more posterior elements of a vertebra, such as one or more portions of the lamina and/or the spinous process. In general, fixation or support component of a joint prosthesis (i.e., via the laminar fixation arm 3105) extends through, or is otherwise mounted on, a laminar portion of a vertebral body as further described below. Desirably, laminar augmentation not only provides additional fixation for the implant, but also provides a significant anti-rotation feature, especially where the components of the implant are secured into the targeted vertebrae using a combination of screw threads (for immediate mechanical fixation) and biological ingrowth (for long-term fixation) of the implant.

Figure 39A:
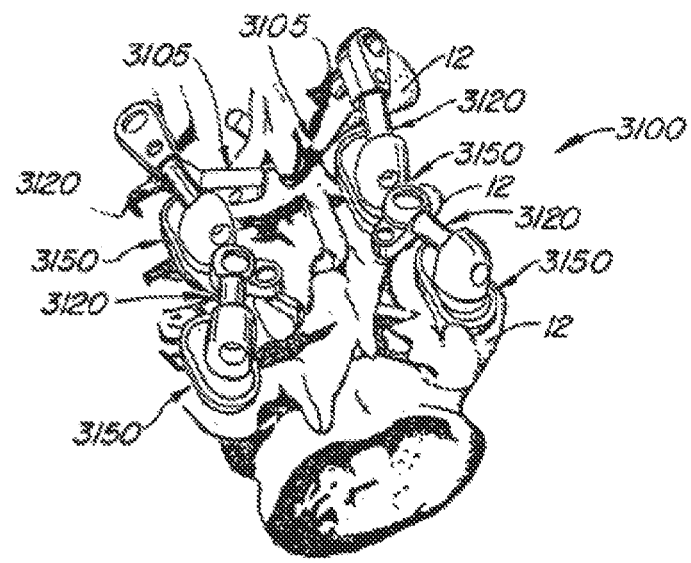
FIGS. 39A-39F illustrates an alternate embodiment of a facet replacement incorporating a laminar support arm.
Figure 39B:
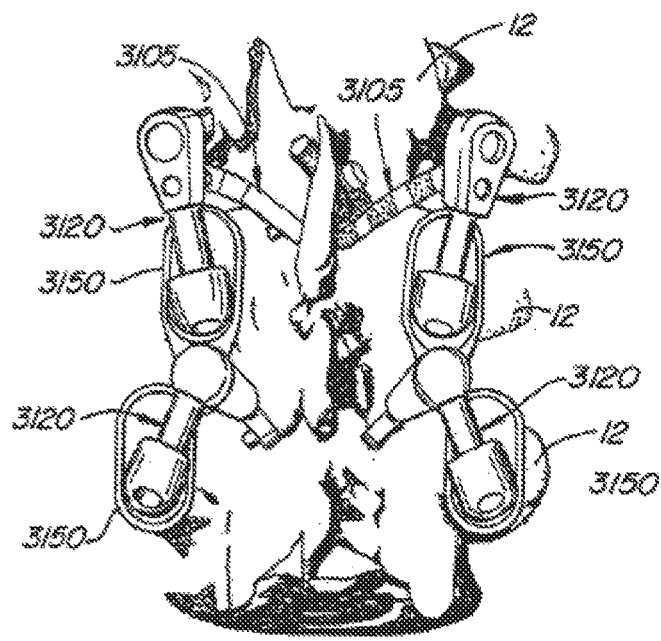
Figure 39C:
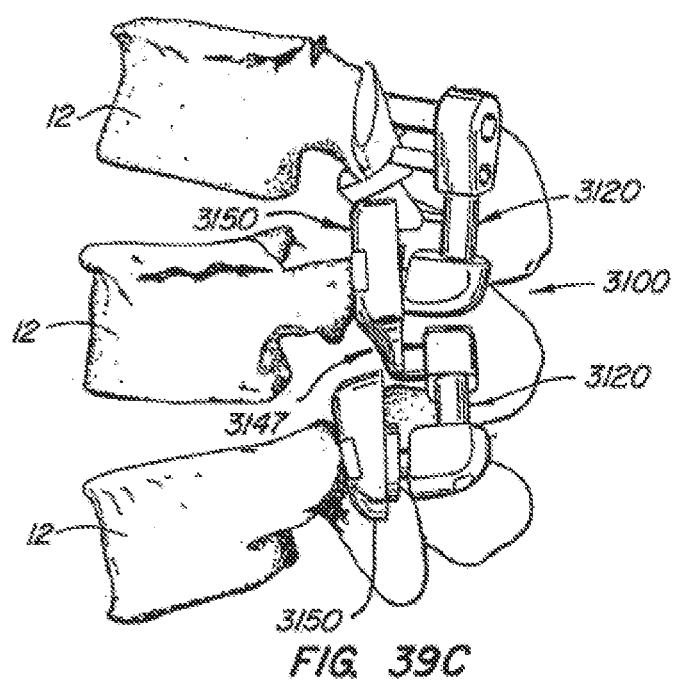
Figure 39D:
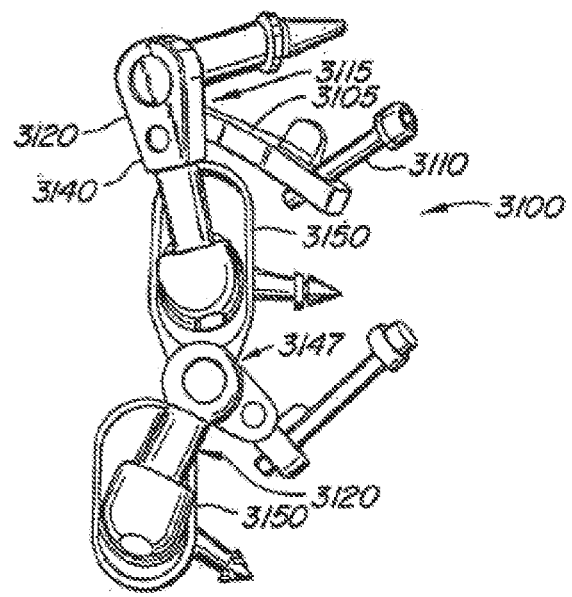
Figure 39E:
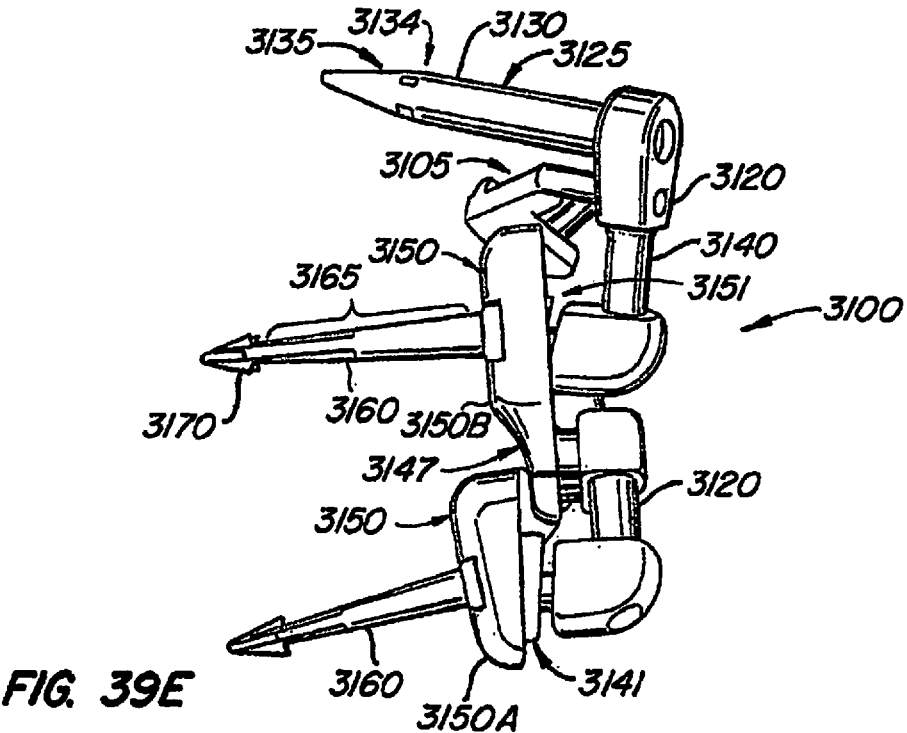
Figure 39F:
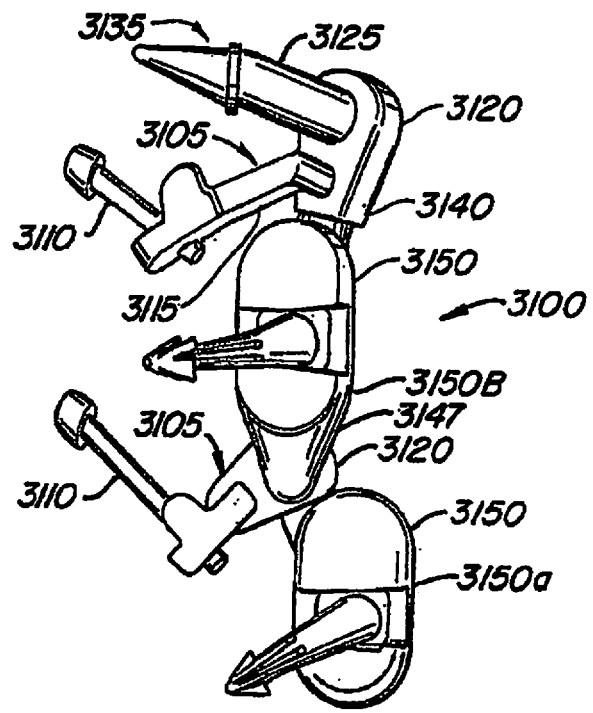
Figure 40A:
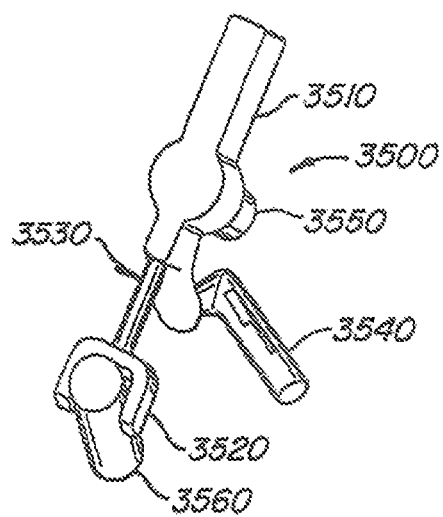
FIGS. 40A-40D depicts an embodiment of a saw capture guide.
Figure 40B:
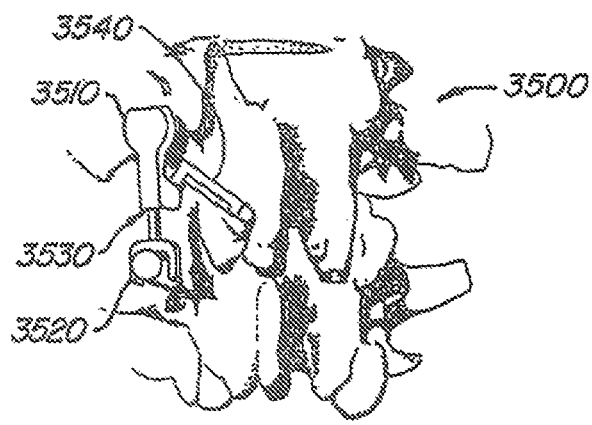
Figure 40C:
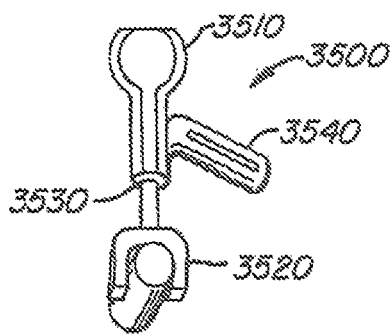
Figure 40D:
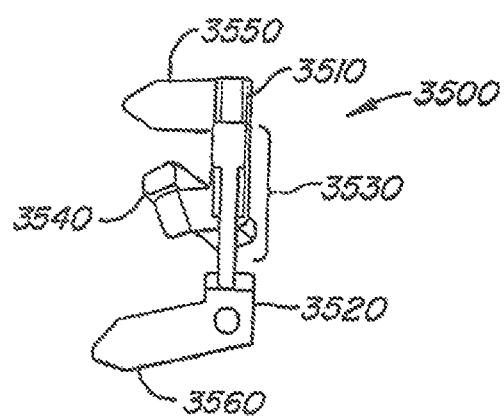

Another feature of the modular design is that the prosthesis and it components can be easily replaceable or reusable, as may be needed after an initial implantation procedure and in a subsequent implantation or "revision" procedure. As will be understood by those skilled in the art, if additional facet joints need to be replaced on adjacent spinal levels, the existing components can be entirely removed and new prostheses implanted; certain pre-existing components left in place and mated with new components; or alternatively no components removed and new components merely added on to already implanted joint prosthesis. FIGS. 39D, 39E and 39F depict various views of the joint prosthesis 3100 pictured in FIGS. 39A-39C, with the vertebral bodies removed to better illustrate the laminar fixation arms 3105, the cephalad prostheses 3120, and caudal prostheses 3150 and their components and features.

The laminar fixation arms 3105 have a first end 3110 and a second end 3115. The first end 3110 of laminar fixation arm 3105 is adapted to be implanted into a vertebral body (if desired, the first end can incorporate screw threads and/or bony ingrowth surfaces, which can facilitate uncemented fixation, or other fixation member 3108), while the second end 3111 is adapted to couple with cephalad prosthesis 3120. Laminar fixation arm 3105 (if desired) can be movably or non-moveably attached to cephalad prosthesis 3120 using a screw or other fixation member 3106, or can be press fit into cephalad prosthesis 3120. In the present invention, the laminar fixation arms 3105 are generally provided for implantation of joint replacement prosthesis 3100 (specifically cephalad prosthesis 3120) to one or more posterior elements of a vertebra, such as one or more portions of the lamina and/or the spinous process to provide added support, prevent rotation of components, etc. As best shown in FIG. 39B, the laminar fixation arm 3105 extends through or is otherwise mounted on a laminar portion of a vertebral body. Specifically, laminar fixation arm 3105 couples cephalad prosthesis 3120 to the vertebral body via laminar fixation at the base of a spinous process, with the laminar fixation arm 3105 traversing the vertebra midline as defined by the spinous process and through another lamina portion. This laminar attachment of the cephalad joint prosthesis 3120 via the laminar fixation arm 3105 desirably does not block access to the pedicle area of a vertebral body, and thus leaves this area free for attaching other prostheses or devices and provides additional support and reduces or eliminates the effects or occurrence of torsion, rotation, bending and the like of the joint prosthesis 3100 as is further detailed below. In addition, the modularity and adaptability of the laminar arm allows the physician the freedom to resect or remove a desired amount of laminar material (which can greatly vary due to the extent of the compression or stenosis to be treated, as was as the treatment goals and the preference of the physician), and secure the laminar arm to the remaining laminar material in a secure and repeatable manner. This allows the physician to remove as much laminar material as he or she feels is necessary to attain the treatment goals, without fear of having too little lamina remaining for adequate fixation of the implant.

The cephalad prosthesis 3120, as best shown in FIGS. 39D-39F, comprises a bone engaging arm or anchor 3125 and a second arm 3140 adapted to couple to the translaminar fixation arm 3105 and an articulating head 3141. The articulating head 3141 is desirably adapted to articulate with the caudal cup 3151 of the caudal prosthesis 3150.

The laminar fixation arm 3105 is desirably coupled to the cephalad prosthesis 3120 on the second arm 3140. The anchor 3125 of the cephalad prosthesis includes a cephalad stem 3130 and a distal tip 3135. The cephalad stem 3130 and the distal tip 3135 can be threaded or otherwise configured to engage bone, and may (or may not be) use with bone cement for stable and permanent attachment of this component to the vertebral body. (Alternatively, the distal tip 3135 could be formed integrally with the cephalad stem 3130, of the same or a different material as the cephalad stem 3130.) The cephalad stem 3130 can also have surface features and/or one or more spike-like projections 3134 radially disposed about the distal tip 3135. Surface features may be, for example, a textured surface or other surface such as, surface features to assist in bony in-growth while the one or more spiked projection may be provided to prevention rotation, etc., of cephalad prosthesis 3120.

Various embodiments of a caudal prostheses 3150 are also illustrated in FIGS. 39E and 39F. Each of the caudal prosthesis 3150 includes a caudal cup 3151 and a fixation element or caudal anchor 3160. The caudal cup 3151 of each prosthesis 3150 includes a surface (not shown) adapted to receive the articulating head 3141 of the cephalad prosthesis 3120. As with the cephalad anchor 3125, the caudal anchor 3160 includes a caudal stem 3165 and a distal tip 3170. Alternatively, the distal tip 3170 can be formed integrally with the caudal stem 3165, of the same or a different material as the caudal stem 3165. The caudal stem 3165 and distal tip 3170 can be threaded or otherwise configured to engage bone, but preferably without the use of cement. Additionally, the caudal stem 3165 and the distal tip 3170 may include textured or otherwise functional surface features. In some embodiments, the features on the caudal stem 3165 can be different from the features on the distal tip 3170.

As best shown in FIG. 39E, the caudal prosthesis 3150 comprises various forms. A caudal prosthesis especially useful for a single level procedure is identified as 3150A, which differs in various ways from a caudal prosthesis 3150B, which is better suited for a multiple level procedure. One difference between the caudal prosthesis 3150A and 3150B is that the multi-level prosthesis 3150B incorporates an elbow 3147, which desirably connects to the cephalad prosthesis 3120 of the next adjacent level. The elbow 3147 allows a single caudal anchor 3160 to support the entire prosthesis.

FIGS. 40A-40D depict one embodiment of a saw capture guide 3500 constructed in accordance with various teachings of the present invention. The saw capture guide 3500 comprises an upper arm 3510, a lower arm 3520, a sliding arm 3530, and a guide arm 3540. An upper stem 3550 is positioned on the upper arm 3510, and a lower stem 3560 is positioned on the lower arm 3520.

Figure 41A:
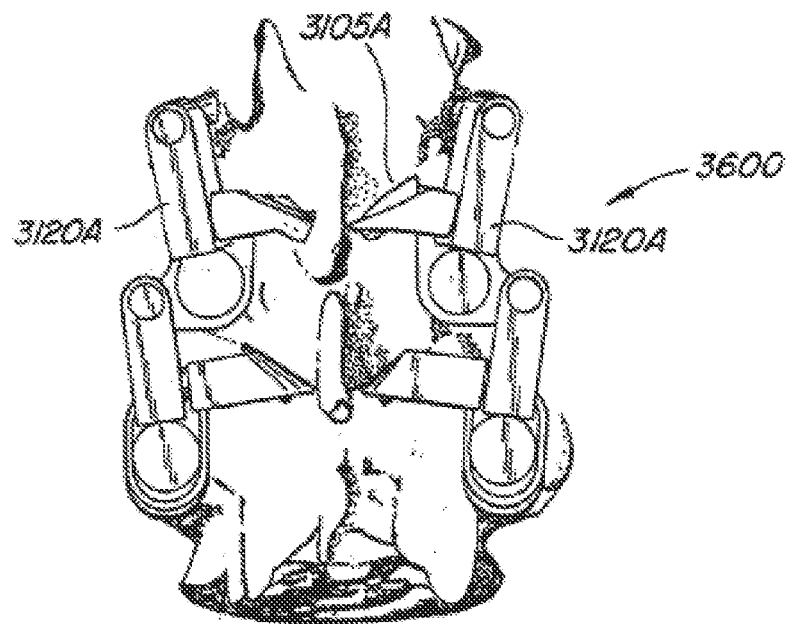
FIGS. 41A-41D depict another alternate embodiment of a facet replacement incorporating a laminar support arm.
Figure 41B:
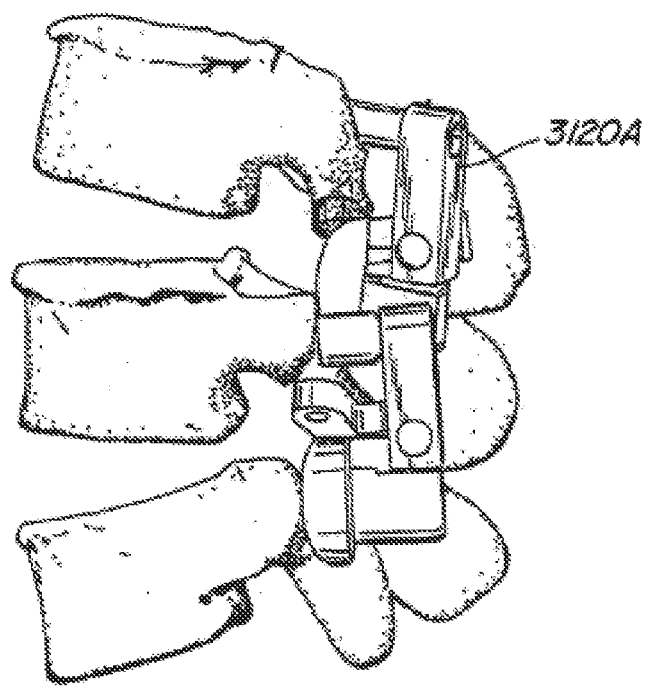
Figure 41C:
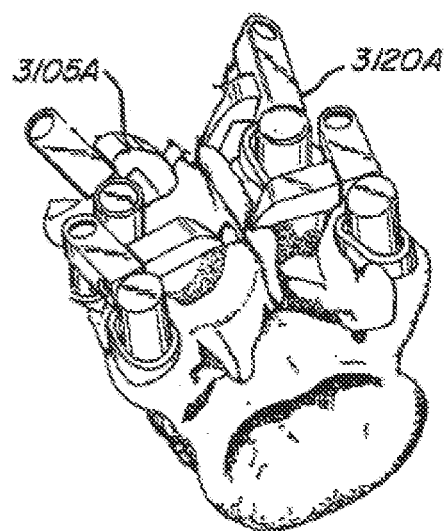
Figure 41D:
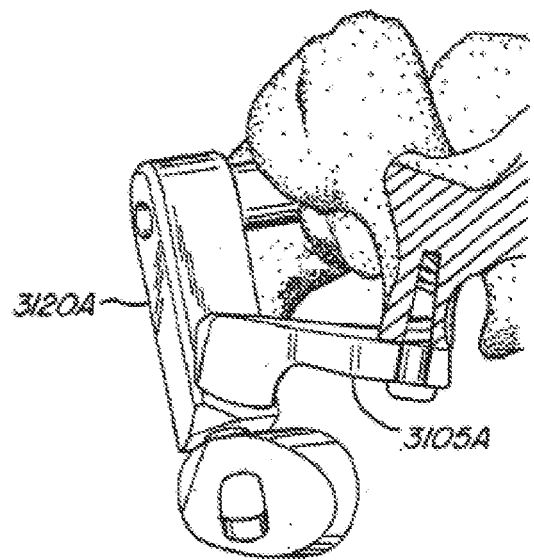

Desirably, the saw capture guide 3500 is used to align a cutting tool (not shown) to resect the lamina of the cephalad vertebral body to properly and repeatably support a laminar support arm 3105A of a facet replacement prosthesis 3600 (see FIG. 41A). To accommodate the varying anatomical alignment and distance between the cephalad and caudal vertebral bodies, the sliding arm 3530 allows the distance between the upper stem 3550 and lower stem 3560 to be varied.

In use, the upper and lower stems 3550 and 3560 are positioned into holes drilled in the cephalad and caudal pedicles (not shown) in preparation for implantation of the facet replacement prosthesis 3600 (see FIG. 41A). Once properly positioned, a surgical cutting tool (not shown) can be introduced through an opening 3570 in the guide arm 3540 to resect the lamina in a desirable and repeatable manner.

FIGS. 41A-41D depict an alternate embodiment of a facet replacement prosthesis 3600 constructed in accordance with various teachings of the present invention. Because many of the disclosed features are similar to those previously disclosed, like reference numerals will be used to describe like components In this embodiment, a laminar support arm 3105A is secured to a laminar surface (such as the laminar surface prepared using the saw capture guide 3500 of FIGS. 40A-40D) with the opposing end of the arm 3105A connecting to the cephalad arm 3120A of the prosthesis 3600. Because the laminar support arm 3105A is perpendicularly connected to the cephalad arm 3120A, the arm 3105A significantly opposes rotation of the cephalad arm 3120A.

Encapsulation

As previously noted, FIG. 12H depicts an additional embodiment of a facet joint replacement prosthesis 8000 constructed in accordance with various teachings of the present invention. In this embodiment, the anchor elements of the prosthesis are separated by one or more flexible or deformable members, which in various embodiments can act to emulate or simulate the articulating joint structures of embodiments disclosed herein. In one disclosed embodiment, one or more polymer blocks 8010 can be secured between the respective cephalad anchor 8020 and caudal anchor 8030 of each of the treated vertebral bodies 8040 and 8050. If desired, the polymer block(s) 8010 can be specifically tailored to allow certain types of motion, but disallow (or allow lesser amounts of) other types of motion. For example, the polymer blocks 8010 could allow vertical relative motion between the treated vertebrae (such as where the lumbar levels are being treated), but allow less lateral or rotational motion between the same vertebrae. Similarly, the polymer blocks 8010 could allow significant rotational relative motion, but limited vertical and lateral relative motion between the treated vertebrae (such as where the thoracic levels are being treated). A further embodiment could incorporate a single flexible/deformable member positioned between all four anchoring elements.

Figure 38:
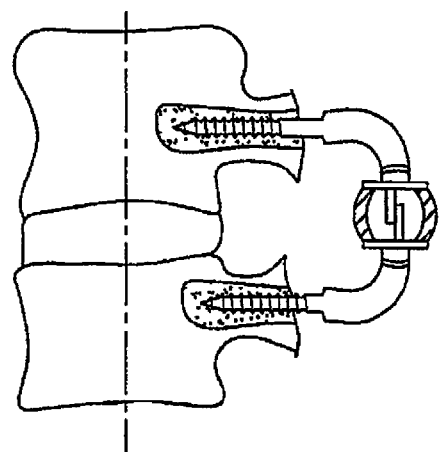
FIG. 38 illustrates an alternative embodiment of a facet joint replacement prosthesis.

Various alternative embodiments can include flexible/deformable materials of various types positioned partially or fully between the anchoring elements, and can include caudal and cephalad bearing elements that incorporate flexible/deformable materials between or comprising part or all of the bearings (See FIG. 37). Various other embodiments can include flexible/deformable materials which augment and/or compliment the metallic and/or ceramic bearing surfaces previously disclosed (see FIG. 38). In one alternative embodiment (see FIG. 12G), the flexible/deformable materials could extend around and encase the bearing surfaces, desirably isolating the bearings from the surrounding tissues while controlling the articulation of the prosthesis in some manner (which could include acting in a manner similar to a shock absorber or vibration damper). This embodiment could flex/deform in response to movement of the articulating surfaces, or it could minimally deform and simply slide along one or more of the anchoring elements during articulation of the prosthesis.

Revision

In the event that it becomes necessary or desirous to reduce, limit and/or prevent articulation of the facet joint replacement prosthesis after implantation, the various embodiments disclosed herein are particularly well-suited to revision procedures to accomplish such objectives. Articulation modification may be accomplished through combinations of one or more of the following: (1) removal of one or more implant anchors, (2) re-attachment of one or more loose anchors, (3) fixation of one or more articulating components, (4) fixation of existing anchors, (5) removal of loose/broken components and/or (6) installation of additional components.

For example, where removal of some or all of the prosthetic components is warranted or desired, the individual anchors for each component can be removed in various ways. If the individual anchor is loose within the cement mantle, it may be possible to simply pull the individual anchor out of the mantle and implantation site. Where fixation of an anchor is strong, however, removal of the anchor may necessitate coring or cutting the anchor out of the surrounding cement mantle and/or bone. In such a case, the housings of the prosthesis can be loosened, and the cephalad bearings, cross-arm and housings detached and removed from the prosthesis. The caudal cups can then be removed from their respective individual anchors by compressing the cups and anchors in the directions opposite to the taper lock, thereby freeing the cup from the anchor. With respect to the cephalad arms, the bent portion of the arm can be cut free of its individual anchor using a set of surgical cutters capable of cutting 6.5 mm diameter titanium rods. Because all of the individual anchors are circular in cross-section, a surgical core saw or hole saw may then be placed over the individual anchor and the cement mantle cut away from the surface of the anchor, with the saw advanced over the anchor until reaching the expanded distal tip of the anchor. The individual anchor can then be withdrawn from the implantation site. Other instruments capable of removing the cement mantle could include powered cutters, heat probes, ultrasonic cutters and/or laser ablators, for example.

Depending upon the nature of the loosened anchor, it may be possible to re-cement the anchor into an existing or new position. For example, an 11-gauge spinal needle may be introduced down the pedicle channel (if sufficient room in the pedicle exists), or a lateral or posterior-lateral approach to and into the vertebral body itself may be used to insert additional cement or other fixation material to further augment the existing anchoring material. Alternatively, a new anchor of the same or different size may be secured to the targeted bone.

Where some, but not all, of the articulating components have loosened and/or failed, the remaining components may be "fixed" or secured using locking caps (previously described) or other devices (such as locking rods) to immobilize the remaining articulating components to each other. Where such devices are augments with additional fusion procedures, including the use of fusion cages, such securing may be sufficient to induce an arthrodesis across the intervertebral space.

Where various components of the articulating prosthesis have failed or become damaged, and especially when the prosthesis is a modular prosthesis (as previously described), it may simply be necessary to remove the modular components from the anchoring elements, and attach fusion hardware to the anchoring elements in their place. Alternative embodiments could include additional components that induce fusion across some levels, while retaining motion across other levels. In addition, it may be necessary to alter components of the facet replacement prosthesis where a patient has had a facet replacement prosthesis implanted in a previous surgery (while retaining a natural disc), but subsequent degeneration of the disc necessitates insertion of an artificial disc replacement (which may require different facet replacement components to be installed).

In the case of a modular prosthesis (such as those embodiments disclosed in FIGS. 39A-39F and 41A-41D), revision, repair and or extension of the existing prosthesis can be accomplished by removing the broken, unwanted or unneeded modular components from the vertebral anchors, and replacing these components (if necessary) with new components to accomplish the surgical objectives. For example, various components of a single-level facet replacement prosthesis could be removed and replaced with components that allow replacement of facet structures on multiple levels. Similarly, where spinal degeneration has progressed to the point where spinal fusion becomes necessary (or continued articulation becomes untenable or unacceptable painful), the articulating components can be removed and replaced with components better suited for fusion of the affected level(s).

Spinal Unit Replacement

The various embodiments disclosed herein are well suited for implantation in conjunction with various spinal surgical procedures and spinal implants, including artificial disc replacement, nucleus replacement, annular repair and/or stenosis treatment (including decompressive laminectomy). If desired, the facet replacement prosthesis can be specifically designed to accommodate a specific treatment regimen, or a single type or design of spinal implant, or a facet replacement prosthesis could be suitable for use with more than one treatment regimen and/or spinal type or design of spinal implant.

In the case of the combination of a facet replacement prosthesis with an artificial disc (desirably creating a total joint replacement in one or more functional spinal units), one or more components of the facet replacement prosthesis can be implanted into the vertebral body, into the artificial disc, or into a combination or of both. One concern currently existing with artificial disc replacement devices is the potential or tendency for the disc replacement components to "slip" or migrate within (or partially or totally out of) the interdisc space post-surgery, especially where these components migrate towards the spinal cord, exiting nerve roots, or major spinal vasculature. Where the facet replacement prosthesis attaches to, connects to, or contacts (in some manner) one or more portions of the artificial disc prosthesis, however, the facet replacement prosthesis may advantageously reduce or eliminate the opportunity for the artificial disc prosthesis to migrate from a desired position within the disc space. Desirably, the facet replacement prosthesis is well secured into one or both of the vertebral bodies of the functional spinal unit, thereby well anchoring the artificial disc prosthesis as well. In fact, where the artificial disc prosthesis and the facet joint replacement prosthesis are each secured to each of the vertebral bodies (i.e., the facet joint replacement prosthesis secured into the pedicles and/or lamina of the vertebral bodies, and the artificial disc replacement prosthesis secured into the upper and lower endplates of the vertebral bodies), the resulting spine joint replacement construct would be extremely well anchored and unlikely to migrate or loosen. However, even where a portion of the facet replacement prosthesis is simply in contact with an artificial disc replacement device (or possibly positioned between the artificial disc replacement and the spinal cord, and not actually connected to or in immediate contact with the disc replacement), the presence of the facet replacement components could be a barrier to artificial disc components migrating towards the spinal cord.

The facet joint replacement components could connect or attach to an artificial disc replacement prosthesis in various manners, including through the interior of one or more vertebral bodies, or around the anterior, lateral or posterior walls of the vertebral body (and into the interdisc space), or some combination of both.

In the case of annular repair and/or implantation of an artificial disc nucleus, it may be desirable that the facet replacement prosthesis bear a disproportionately higher share of the spinal load, thereby shielding the repaired and/or damaged tissue during natural healing or to prevent further degeneration or unacceptable loading on the other portions of the spine.

While various of the above described embodiments have been shown and described utilizing a crossbar having two ends and pairs of cephalad and caudal prosthesis elements, it is to be appreciated that embodiments and systems of the present invention may include adaptable spinal prosthesis embodiments utilizing the inventive concepts described herein for a single cephalad element, single caudal element and a crossbar having only one end.

The invention claimed is:

1. An adaptable spinal facet joint prosthesis system, comprising:
    a pedicle fixation element having a distal end configured to engage bone;
    a laminar fixation element having a distal end configured to engage bone;
    a crossbar having a first end and a second end;
    a facet joint bearing surface having a location adaptable with respect to at least one of the pedicle fixation element and the laminar fixation element, wherein the facet joint bearing surface is disposed at the first and second ends of the crossbar, and wherein at least one of the pedicle fixation element and the laminar fixation element includes a bearing surface configured to receive the facet joint bearing surface
    wherein a portion of the pedicle fixation element and the laminar fixation element limits the movement of the crossbar, and
    a dual clamp housing having a first opening for receiving a first cephalad prosthesis and a second opening for receiving the crossbar, wherein a crossbar lock includes a single fastener that is received in the first opening and urges the dual clamp housing to clamp down on the first cephalad prosthesis and on the crossbar.

2. The system of claim 1, further comprising a facet joint bearing surface support, wherein the laminar fixation element and the pedicle fixation element extend from the facet joint bearing surface support.

3. The system of claim 1, wherein the laminar fixation element is adapted to extend through a lamina portion of a vertebral body.

4. The system of claim 1, wherein the laminar fixation element is configured to contact a resected laminar surface.

5. The system of claim 1, wherein the laminar fixation element and the pedicle fixation element are configured to resist rotation of the bearing surface.

6. The system of claim 1, wherein the bearing surface comprises a cephalad bearing surface.

7. The system of claim 1, wherein the bearing surface comprises a caudal bearing surface.

8. The system of claim 7, wherein the bearing surface comprises a cephalad bearing surface.

9. The system of claim 8, wherein the at least one of the laminar fixation element and the pedicle fixation element comprises bone growth material.

10. A system for treating spinal pathologies including an adaptable facet joint prosthesis comprising:
- a crossbar having a first end and a second end;
- a pair of cephalad prosthesis elements each having a bone engaging end and an end adapted to couple to the crossbar;
- a pair of caudal prosthesis elements each having a fixation element and a surface adapted to receive a crossbar end therein; and
- a dual clamp housing having a first opening for receiving a first cephalad prosthesis and a second opening for receiving the crossbar element, wherein a crossbar lock includes a single fastener that is received in the first opening and urges the dual clamp housing to clamp down on the first cephalad prosthesis and on the crossbar,
- wherein the pair of caudal prosthesis elements limit the movement of the crossbar.

11. The adaptable spinal facet joint prosthesis according to claim 10 wherein the distance between the crossbar first end and second end is adjustable.

12. The adaptable spinal facet joint prosthesis according to claim 10 wherein the crossbar first end and second end have a round surface to engage with the caudal prosthesis element surface adapted to receive a crossbar end.

13. The adaptable spinal facet joint prosthesis according to claim 10 wherein the bone engaging end of at least one of the pair of cephalad prosthesis elements is disengageably coupled to a portion of the at least one of the pair of cephalad prosthesis elements adapted to couple to the crossbar.

14. The adaptable spinal facet joint prosthesis according to claim 13 wherein the bone engaging end is adapted to receive one of a plurality of bone engaging ends, each one of said plurality of bone engaging ends having a different length.

15. The adaptable spinal facet joint prosthesis according to claim 10 wherein at least one of the pair of cephalad prosthesis elements or at least one of the pair of caudal prosthesis elements is configured not to rotate.

16. The adaptable spinal facet joint prosthesis according to claim 10 further comprising a crossbar mount having a crossbar engaging portion and a cephalad prosthesis element engaging portion.

17. The adaptable spinal facet joint prosthesis according to claim 16 wherein the crossbar passes through the crossbar engaging portion.

18. The adaptable spinal facet joint prosthesis according to claim 16 wherein the crossbar is attached to the crossbar engaging portion.

19. The adaptable spinal facet joint prosthesis according to claim 16 wherein when the crossbar is connected to the crossbar engaging portion, the crossbar mount may be rotated about the crossbar.

\* \* \* \* \*